US007611831B2

(12) United States Patent
Hei

(10) Patent No.: US 7,611,831 B2
(45) Date of Patent: *Nov. 3, 2009

(54) ADSORBING PATHOGEN-INACTIVATING COMPOUNDS WITH POROUS PARTICLES IMMOBILIZED IN A MATRIX

(75) Inventor: Derek J. Hei, Concord, CA (US)

(73) Assignee: Cerus Corporation, Concord, CA (US)

( * ) Notice: Subject to any disclaimer, the term of this patent is extended or adjusted under 35 U.S.C. 154(b) by 228 days.

This patent is subject to a terminal disclaimer.

(21) Appl. No.: 11/243,822

(22) Filed: Oct. 4, 2005

(65) Prior Publication Data

US 2006/0093999 A1 May 4, 2006

Related U.S. Application Data

(63) Continuation-in-part of application No. 10/011,202, filed on Dec. 7, 2001, now abandoned, which is a continuation of application No. 09/112,400, filed on Jul. 8, 1998, now abandoned, which is a continuation-in-part of application No. 09/003,113, filed on Jan. 6, 1998, now abandoned, application No. 11/243,822, which is a continuation-in-part of application No. 10/016,323, filed on Dec. 10, 2001, now Pat. No. 6,951,713, which is a continuation of application No. 09/112,068, filed on Jul. 8, 1998, now abandoned, which is a continuation-in-part of application No. 09/003,113, filed on Jan. 6, 1998, now abandoned.

(51) Int. Cl.
*A01N 1/02* (2006.01)
*A61K 35/14* (2006.01)
*C12N 7/06* (2006.01)
*C12M 1/00* (2006.01)
*C07K 1/22* (2006.01)

(52) U.S. Cl. .......................... 435/2; 424/529; 435/238; 435/283.1; 530/412; 530/413; 530/415

(58) Field of Classification Search ........................ None
See application file for complete search history.

(56) References Cited

U.S. PATENT DOCUMENTS

| 3,238,056 | A | 3/1966  | Pall et al.        |
|-----------|---|---------|--------------------|
| 3,729,457 | A | 4/1973  | Davankov           |
| 3,975,481 | A | 8/1976  | Baumgaertner       |
| 4,064,042 | A | 12/1977 | Kunin              |
| 4,110,391 | A | 8/1978  | Berzen et al.      |
| 4,157,723 | A | 6/1979  | Granzow et al.     |
| 4,160,059 | A | 7/1979  | Samejima           |
| 4,169,204 | A | 9/1979  | Hearst et al.      |
| 4,196,281 | A | 4/1980  | Hearst et al.      |
| 4,202,775 | A | 5/1980  | Abe et al.         |
| 4,252,645 | A | 2/1981  | Marconi et al.     |
| 4,309,247 | A | 1/1982  | Hou et al.         |
| 4,390,619 | A | 6/1983  | Harmening-Pittiglio|
| 4,404,285 | A | 9/1983  | Hou                |
| 4,460,530 | A | 7/1984  | Hanson et al.      |
| 4,559,145 | A | 12/1985 | Hou                |
| 4,576,715 | A | 3/1986  | Michaels et al.    |
| 4,594,202 | A | 6/1986  | Pall et al.        |
| 4,664,683 | A | 5/1987  | Degen et al.       |
| 4,684,521 | A | 8/1987  | Edelson            |
| 4,693,981 | A | 9/1987  | Wiesehahn et al.   |
| 4,727,027 | A | 2/1988  | Wiesehahn et al.   |
| 4,728,432 | A | 3/1988  | Sugiyama et al.    |
| 4,748,120 | A | 5/1988  | Wiesehahn          |
| 4,777,069 | A | 10/1988 | Cederberg et al.   |
| 4,880,843 | A | 11/1989 | Stein              |
| 4,925,880 | A | 5/1990  | Stein              |
| 4,935,141 | A | 6/1990  | Buck et al.        |
| 4,943,373 | A | 7/1990  | Onishi et al.      |
| 4,959,148 | A | 9/1990  | Clark, III         |
| 4,985,153 | A | 1/1991  | Kuroda et al.      |
| 5,019,311 | A | 5/1991  | Koslow             |
| 5,030,352 | A | 7/1991  | Varady et al.      |
| 5,037,857 | A | 8/1991  | Maroldo et al.     |
| 5,094,960 | A | 3/1992  | Bonomo             |

(Continued)

FOREIGN PATENT DOCUMENTS

AU        6339190 A1    4/1991

(Continued)

OTHER PUBLICATIONS

Rai, S. et al. (1993). "Dramatic Improvements in Viral Inactivation with Brominated Psoralens, Naphthalenes and Anthracenes," *Photochem. and Photobio.* 58(1):59-65.
(Dec. 5, 1988) 510(k) Notification Submitted to the U.S. Food & Drug Administration, Asahi Medical Co., Ltd., Tokio, Japan.
Andrade, J. D. et al. (1971). "Coated Adsorbents for Direct Blood Perfusion: Hema/activated Carbon," *Trans. Amer. Soc. Artf. Int. Organs*, vol. XVII, pp. 222-228.
Artuc et al. (1979). "Reversible Binding of 5- and 8-Methoxypsoralen to Human Serum Proteins (Albumin) and to Epidermis in vitro," *Brit. J. Derm.* 101:669-677.
Bertolini, F. et al. (1992). "Platelet Concentrates Stored in Synthetic Medium After Filtration," *Vox Sang* 67:82-86.
Bock, M. et al. (1991). "White Cell Depletion of Single-Donor Platelet Preparations by a New Adsorption Filter," *Transfusion* 31:333-334.

(Continued)

*Primary Examiner*—David M Naff
(74) *Attorney, Agent, or Firm*—Morrison & Foerster LLP

(57) ABSTRACT

Methods and devices are provided for reducing the concentration of low molecular weight compounds in a biological composition containing cells while substantially maintaining a desired biological activity of the biological composition. The device comprises highly porous adsorbent particles, and the adsorbent particles are immobilized by an inert matrix. The matrix containing the particles is contained in a housing, and the particles range in diameter from about 100 μm to about 1500 μm. The device can be used to adsorb and remove a pathogen-inactivating compounds from a biological composition such as a blood product.

56 Claims, 24 Drawing Sheets

U.S. PATENT DOCUMENTS

| | | |
|---|---|---|
| 5,100,564 A | 3/1992 | Pall et al. |
| 5,128,048 A | 7/1992 | Stewart et al. |
| 5,137,926 A | 8/1992 | Maroldo et al. |
| 5,147,722 A | 9/1992 | Koslow |
| 5,176,634 A | 1/1993 | Smith et al. |
| 5,190,657 A | 3/1993 | Heagle et al. |
| 5,209,347 A | 5/1993 | Fabisiewicz et al. |
| 5,234,608 A | 8/1993 | Duff |
| 5,269,917 A | 12/1993 | Stankowski |
| 5,279,742 A | 1/1994 | Markell et al. |
| 5,288,605 A | 2/1994 | Lin et al. |
| 5,328,758 A | 7/1994 | Markell et al. |
| 5,354,262 A | 10/1994 | Boehringer et al. |
| 5,399,719 A | 3/1995 | Wollowitz et al. |
| 5,407,581 A | 4/1995 | Onodera et al. |
| 5,418,130 A | 5/1995 | Platz et al. |
| 5,455,040 A | 10/1995 | Marchant |
| 5,456,845 A | 10/1995 | Nishimura et al. |
| 5,459,030 A | 10/1995 | Lin et al. |
| 5,468,536 A | 11/1995 | Whitcomb et al. |
| 5,482,828 A | 1/1996 | Lin et al. |
| 5,486,293 A | 1/1996 | Boschetti et al. |
| 5,486,410 A | 1/1996 | Groeger et al. |
| 5,501,795 A | 3/1996 | Pall et al. |
| 5,504,163 A | 4/1996 | Tegen et al. |
| 5,531,902 A | 7/1996 | Gallup |
| 5,543,062 A | 8/1996 | Nishimura |
| 5,556,541 A | 9/1996 | Ruschke |
| 5,559,250 A | 9/1996 | Cook et al. |
| 5,571,666 A | 11/1996 | Floyd et al. |
| 5,593,823 A | 1/1997 | Wollowitz et al. |
| 5,605,746 A | 2/1997 | Groeger et al. |
| 5,607,766 A | 3/1997 | Berger |
| 5,616,254 A | 4/1997 | Pall et al. |
| 5,639,376 A | 6/1997 | Lee et al. |
| 5,660,731 A | 8/1997 | Piechocki et al. |
| 5,662,728 A | 9/1997 | Groeger |
| 5,773,384 A | 6/1998 | Davankov et al. |
| 5,817,354 A | 10/1998 | Mozaffar et al. |
| 5,871,900 A | 2/1999 | Wollowitz et al. |
| 5,882,517 A | 3/1999 | Chen et al. |
| 5,883,256 A | 3/1999 | Schuler et al. |
| 6,228,995 B1 | 5/2001 | Lee |
| 6,270,952 B1 | 8/2001 | Cook et al. |
| 6,294,361 B1 | 9/2001 | Horowitz et al. |
| 6,319,662 B1 | 11/2001 | Foley et al. |
| 6,348,309 B1 | 2/2002 | Mohr et al. |
| 6,544,727 B1 | 4/2003 | Hei |
| 6,951,713 B2 | 10/2005 | Hei et al. |
| 2002/0045228 A1 | 4/2002 | Hei |
| 2002/0094568 A1 | 7/2002 | Hei |
| 2002/0115585 A1 | 8/2002 | Hei |
| 2002/0192632 A1 | 12/2002 | Hei et al. |
| 2004/0185544 A9 | 9/2004 | Hei |
| 2004/0185553 A9 | 9/2004 | Hei |

FOREIGN PATENT DOCUMENTS

| | | |
|---|---|---|
| CA | 2065842 | 12/1999 |
| DE | 27 21 511 A1 | 11/1977 |
| DE | 249 274 A1 | 9/1987 |
| DE | 38 19 000 A1 | 12/1989 |
| EP | 0 099 586 A2 | 3/1986 |
| EP | 0 099 586 A3 | 3/1986 |
| EP | 0 099 586 B1 | 3/1986 |
| EP | 0 230 247 A2 | 7/1987 |
| EP | 0 230 247 A3 | 7/1987 |
| EP | 0 366 946 A1 | 5/1990 |
| EP | 0 366 946 B1 | 5/1990 |
| EP | 0 776 668 A2 | 9/2003 |
| EP | 0 776 668 A3 | 9/2003 |
| EP | 0 776 668 B1 | 9/2003 |
| JP | 62-283198 A2 | 12/1987 |
| JP | 03-228769 A | 10/1991 |
| JP | 03-229610 A | 10/1991 |
| JP | 03-295558 A | 12/1991 |
| JP | 04-012755 A | 1/1992 |
| WO | WO-83/00023 A1 | 1/1983 |
| WO | WO-91/03933 A1 | 4/1991 |
| WO | WO-94/11556 A1 | 5/1994 |
| WO | WO-94/27433 A1 | 12/1994 |
| WO | WO 95/00141 A1 | 1/1995 |
| WO | WO-95/00631 A1 | 1/1995 |
| WO | WO 95/16348 A1 | 6/1995 |
| WO | WO-95/18665 A1 | 7/1995 |
| WO | WO-96/39818 A1 | 12/1996 |
| WO | WO-96/40857 A1 | 12/1996 |
| WO | WO-97/18844 A1 | 5/1997 |
| WO | WO-97/36581 A1 | 10/1997 |
| WO | WO-97/37536 A1 | 10/1997 |
| WO | WO-98/30327 A1 | 7/1998 |
| WO | WO-99/34914 A1 | 7/1999 |
| WO | WO-99/34915 A1 | 7/1999 |
| WO | WO-99/37340 A2 | 7/1999 |
| WO | WO-99/37340 A3 | 7/1999 |

OTHER PUBLICATIONS

Bogusz et al. (1978). "Isolation of Drugs from Blood and Tissues with XAD-1 Bags," *Forensic Science* 12(1):73-82.

Boomgaard, M.N. et al. (1994). "In vitro Evaluation of Platelet Concentrates, Prepared from Pooled Buffy Boast, Stored for 8 days After Filtration," *Transfusion* 34:311-316.

Brettell, T.A. et al. (1987). "Forensic Science," *Anal. Chem.* 59:162-174.

Carmen, R. (1993). "The Selection of Plastic Materials for Blood Bags," *Trans. Med. Rev.* 7(1):1-10.

Chandy, T. et al. (1992). "Polylysine-Immobilized Chitosan bBeads as Adsorbents for Bilitubin," *Artificial Organs* 16:568-576.

Chaplin, H. et al. (1986). "Frozen Storage of 11 Units of Sickle Cell Red Cells for Autologous Transfusion of a Single Patient," *Transfusion* 26(4):341-345.

Coli et al., (1992). "Phosphate Removal by Resin Hemoperfusion Efficacy and Biocompatibility of a New Exchange," *Biomat. Art Cells and Immob. Biotech.* 20:1153-1163.

Courtney, J.M. et al. (1993). "Monitoring of the Blood Response in Blood Purification," *Artificial Organs* 17:260-266.

Cruse, J.M. et al. (1995). *Illustrated Dictionary of Immunology*, CRC Press, p. 37.

Davankov, V.A. et al. (1990). "Structure and Properties of Hypercrosslinked Polystyrene-The First Representative of a New Class of Polymer Networks," *Reactive Polymers* 13:27-42.

Denti, E. et al. (Jul.-Aug. 1977). "Evaluation of Novel Sorbent Systems for Joint Hemodialysis and Hemoperfusion," *Med. Instrument.* 11(4):212-214.

Dodd et al. (1991). "Inactivation of Viruses in Platelet Suspensions that Retain Their in vitro Characteristics: Comparison of Psolaren-Ultraviolet A and Merocyanine 540 Visible Light Methods," *Transfusion* 31:483-490.

Dunlop, E.H. et al. (1978). "Physico-Chemical Aspects of the Removal of Protein-Bound Substances by Charcoal and Other Adsorbents of Potential Value in Systems of Artificial Liver Support: Part 1-Equilibrium Properties," *Med. & Biol. Eng. & Comput.* 16:343-349.

Dunlop, E.H. et al. (1978). "Physico-Chemical Aspects of The Removal of Protein-Bound Substances by Charcoal and Other Adsorbents of Potential Value in Systems of Artificial Liver Support: Part 2-kinetics of Removal," *Med. & Biol. Eng. & Comput.* 16:350-362.

Dvilansky et al. (1992). "Evaluation of a New Polyacrolein Microsphere (Acrobead) Protein A Column: An in vitro Study Using the Blood of Patients with Immune Thrombocytopenia or Malignancies," *Transfusion* 32(3):210-214.

English Translation of PCT Application PCT/DE90/00691.

Faenza et al. (1992). "Hemoperfusion with a New Anion Exchange Resin Corrects the Metabolic Alkalosis in Pyloric Stenosis: An Experimental Demonstration," *Int's J. Art. Organs* 15:677-680.

Fini, M. et al. (1995). "In vitro Evaluation of Heparin Adsorption During Haemoperfusion with Dowex 1×2 Anion Exchange Resin," *Art Cells Blood Subs. and Immob. Biotech.* 23(1):101-108.

Goodrich, R.P. et al. (Jun. 30, 1994). "Selective Inactivation of Viruses in the Presence of Human Platelets: UV Sensitization with Psoralen Derivatives," *Proc. Natl. Acad. Sci. USA*, 91:5552-5556.

Hanson, C.V. et al. (1992). "Photochemical Inactivation of Viruses with Psoralens: An Overview," *Blood Cells* 18:7-25.

Harmening, D.M. et al. (Nov./Dec. 1979). "The Use of Ion-Exchange Resins as a Blood Preservation System," *Transfusion* 19(6):675-681.

Heddle, N.M. (1995). "Febrile Nonhemolytic Transfusion Reactions to Platelets," *Hematology* 2:478-483.

Hei, D.J. et al. (1994). "Removal of Cytokines From HAS-Containing Solutions by Adsorption Onto Silica," *Biotech. Bioeng.* 44:1023-1030.

Heinmets, et al. (1955). "Inactivation of Viruses in Plasma by Photosensitized Oxidation," Joint Report with the Naval Medical Research Institute, *Walter Reed Army Institute of Research*, 53-55. pp. 1-16.

Hilfenhaus, J. et al. (1987). "A Strategy for Testing Established Human Plasma Protein Manufacturing Procedures for Their Ability to Inactivate or Eliminate Human Immunodeficiency Virus," *J. Biol. Std.* 15:251-263.

Horowitz, B. et al. (1985). "Inactivation of Viruses in Labile Blood Derivatives," *Transfusion* 25:516-522.

Hughes, R. et al. (1979). "Albumin-Coated Amberlie XAD-7 Resin for Hemoperfusion in Acute Liver Failure Part II: in vivo Evaluation," *Artificial Organs* 3(1):23-26.

Hyllner, M. et al. (Mar. 1997). "Complement Activation During Storage of Whole Blood, Red Cells, Plasma, and Buffy Coat," *Transfusion* 37:264-268.

Ibrahim, G. et al. (1975). "Application of Amerlite XAD-2 Resin for General Toxicological Analysis," *J. Chrom.* 108:107-116.

Ishihara, K. et al. (1994). "Selective Adhesion of Platelets on a Polyion Complex Composed of Phospholipid Polymers Containing Sulfonate Groups and Quartenary Ammonium Groups," *J. Biomed. Mat. Res.* 28:1347-1355.

Joustra-lkjkhuis, A.M. (1994). "Effect of Filtration on Subsequently Stored Platelet Concentrates," *Vos Sang* 67:22-27.

Kambic, H. et al. (1983). "Historical Perspective Therapeutic Applications and New Frontiers," in *Plasmapherisis*, Second ed., Intern. Center for Artific. Organs and Transplantation: Cleveland OH, pp. 75-78.

Kao, K.J. et al. (1995). "White Cell Reduction in Platelet Concentrates and Packed Red Cells by Filtration: A Multicenter Clinical Trial," *Transfusion* 35:13-19.

Kiremitci et al. (1985). "Properties of New Sorbents Containing Activated Carbon-PHEMA-PEG," *Int'l J. of Art Org.* 8(4):201-208.

Klein, H.G. ed. (1997). *Standards for Blood Banks and Transfusion Services* 18th edition, Bethesda, M.D.: Amer. Assoc. of Bld. Bnk, pp. 14-17.

Kril et al. (1990). "Influence of Hydrophobicity on the Ion Exchange Selectivity Coefficients for Aromatic Amines," *J. Pharm. Sci.* 79:440-443.

Lee, C. J. et al. (1990) "Preparation of Spherical Encapsulation of Activated Carbons and Their Adsorption Capacity of Typical Uremic Toxins," *J. Biomed. Mat. Res.* 24:243-258.

Lin et al. (1989). "Use of 8-Methoxypsolaren and Long-Wavelength Ultraviolet Radiation for Decontamination of Platelet Concentrates," *Blood* 74:517-525.

Lunn, G. et al. (1994). "Removal of Biological Stains from Aqueous Solution Using a Flow-Through Decontamination Procedure," *Biotech. Histochem* 69(1):45-54.

Malchesky, P. et al. (1977). "Membranes Containing Sorbents for Blood Detoxification," *Trans. Am. Soc. Artif. Intern. Organ*, pp. 659-664.

Malchesky, P. et al. (1978). "Sorbent Membranes: Device Designs, Evaluations and Potential Applications," *Artificial Organs* 2(4):367-371.

Margolis-Nunno et al. (1995). "Elimination of Potential Mutagenicity in Platelet Concentrates That Are Virally Inactivated with Psoralens and Ultraviolet a Light," *Transfusion* 35:855-862.

Matsuda, K. et al. (1989). "Experimental Study on the Adsorption of Excess Heparin with Anion Exchange Resin Fiber," *Artificial Organs* 13:504-507.

Matthews, J.L. et al. (1988). "Photodynamic Therapy of Viral Contaminants with Potential for Blood Banking Applications," *Transfusion* 28:81-83.

Miletic et al. (1993). "Complement Activation in Stored Platelet Concentrates," *Transfusion* 33:150-154.

Morel et al. (1992). "Photochemical Inactivation of Viruses and Bacteriophage in plasma and Plasma Fractions," *Blood Cells* 18:27-42.

Moroff et al. (1992). "Factors Influencing Virus Inactivation and Retention of Platelet Properties Following Treatment with Aminomethyltrimethylpsoralen and Ultraviolet a Light," *Blood Cell* 18:43-56.

Moroff et al. (1982). "Factors Influencing Changes in pH During Storage of Platelet Concentrates at 20-24° C.," *Vox Sang* 42:33-45.

Murphy, S. et al. (1994). "In vitro Assessment of the Quality of Stored Platelet Concentrates," *Transfusion Med. Rev.* VII(1):29-36.

Murugavel, S. (1992). "In vitro Studies of the Efficacy of Reversed Phase Silica Gel as a Sorbent for Hemo- and Plasmaperfusion," *Clin. Tox.* 30:69-82.

Nathan et al. (1992). "A Novel Agarose Acrobeads Protein A Column For Selective Immunoadsorbance of Whole Blood: Performance, Specificity and Safety," *Biomat. Art. Cells & Immob. Biotech* 20:23-30.

Nolan, A.P. et al. (1979). "Endotoxin Binding by Charged and Uncharged Resins (38895)," *Proc. Soc. Exp. Biol. & Med.* 149:766-770.

Pardue, K.J. et al. (1992). "Literature Applications for Amberlite®/duolite® Anion Exchange Resins," Literature Survey, 1987-1991, p. 1-b 48, Supelco, Inc.

Pegues et al. (1979). "The Removal of 13C Labeled Endotoxin by Activated Charcoal," *Int'l J. Art. Organs* 2:153-158.

Purolite Technical Bulletin (1995) entitled "Hypersol-Macronet™ Sorbent Resins," The Purolyte Co., (PA), pp. 1-11.

Rodriguez, F. (1989). *Principles of Polymer Systems*, Hemisphere Publishing Corp., 3rd Edition, pp. 449-453.

Rosenhaum, J. et al. (1976). "Resin Hemoperfusion for Acute Drug Intoxication," *Arch. Intern. Med.* 136:263-266.

Schmidt et al. (1993). "Ion-exchange Preconcentration and Group Separation of Ionic and Neutral Organic Compounds," *J. Chromatog.* 640:145-149.

Sergeyev, V.P. et al. (1989). "Comparative Evaluation of the Structure and Properties of Certain Granulated and Fibrous Activated Carboniferous Sorbents," *Biomart. Art. Cells. Art. Org.* 17:353-361.

Shimakaki, K. (1993). "Changes of Pore and Adsorption Capacity of Polyacrylonitrile-based Activated Carbon Fiber (PAN-ACF) in Activation," *Nippon Kagaku Kaishi* 1:54-61.

Shimizu, T. et al. (1993). "Filtration Through a Polyester White Cell-Reduction Filter of Plasma-Poor Platelet Concentrates Prepared with an Acetate-Containing Additive Solution," *Transfusion* 33:730-734.

Shimizu, T. et al. (1994). "Adsorption of Anaphylatoxins and Platelet-Specific Proteins by Filtration of Platelet Concentrates with a Polyester Leukocyte Reduction Filter," *Vox Sang* 66:161-165.

Sintov, A. et al. (1995). "Cross-linked Chondroitin Sulphate: Characterization for Drug Delivery Purposes," *Biomaterials* 16(6):473-478.

Snezhkova et al. (1992). "DNA-Coated Carbon Adsorbents Experimental Assessment and Results of Severe Psoriasis Treatment," *Biomart. Art. Cells. & Immob. Biotech.* 20:1201-1221.

Sun et al. (1990). "Chemically Modified Polymeric Resins for High-Performance Liquid Chromatography," *J. Chrom.* 522:95-105.

Sweeney, J.D. et al. (1995). "White Cell-Reduced Platelet Concentrates Prepared by In-Line Filtration of Platelet-Rich Plasma," *Transfusion* 35:131-136.

Tang, J., et al. (1990). "Free and Glycosidically Bound Volatile Compounds in Fresh Celery (*Apium graveolens* L.)," *J. Agric. Food Chem.* 38:1937-1940.

Tijissen, J. et al. (1979). "A Hamoperfusion Column Based on Activated Carbon Granules Coated with an Ultrathin Membrane of Cellulose Acetate," *Artificial Organs* 3(1):11-14.

Tishler et al. (1984). "Sorbent Therapy of the Porphyrias III. Comparative Efficacy of Experimental Plasma Perfusion with Several Commercial Hemoperfusion Cartridges," *Meth. & Find. Exptl. Clin. Pharmacol.* 6(7):389-393.

Ton, H.Y. et al. (1979). "Albumin-coated Amberlite XAD-7 Resin for Hemoperfusion in Acute Liver Failure—Part I: Adsorption Studies," *Artificial Organs* 3:20-22.

Tsyurupa, M.P. et al. (1995). "Sorption of Organic Compounds From Aqueous Media by Hypercrosslinked Polystyrene Sorbents 'styrosorb'," *Reactive Polymers* 25:69-78.

Valeri Capt. C.R. et al. (1981). "Freeze-Preserved Baboon Red Blood Cells: Effects of Biochemical Modification and Perfusion in vitro," *Am. J. Vet. Res.* 42:1590-1594.

Valerio, F. et al. (1979). "Adsorption Properties of U.I.C.C. Rhodesian Chrysotile and Crocidolite in Aqueous Solution—Effects of Cation Depletion," *AIHA Journal* (40):, pp. 781-788.

van Marwijk, M. et al. (1990). "Filtration: A Method to Prepare White Cell-Poor Platelet Concentrates With Optimal Preservation of Platelet Viability," *Transfusion* 30:34-38.

Verhoeven, M. et al. (1989). "A First Screening for Hemocompatibility of a Universal Support for Selective and Specific Hemoperfusion," *Int'l J. Artificial Organsi* 12:63-67.

Wadenvik, H. et al. (1991). "Leukocyte Removal Filtration of Platelet Concentrates. A Study of Platelet Loss Using Inlabeled Platelets and Dynamic Gamma Camera Scintigraphy," *Eur. J. Haematol.* 47:192-196.

Webb, D. (Apr. 7-20, 1993). "Charcoal Haemoperfusion in Drug Intoxication," British J. of Hosp. Med. 49(7):493-496.

Yoshioka, T. et al. (1983). "Studies of Polystyrene-Based Ion Exchange Fiber. I. The Preparation and Fundamental Characteristics of Polystyrene-Based Ion Exchange Fiber," *The Chem. Soc. of Japan* 56(12):3726-3729.

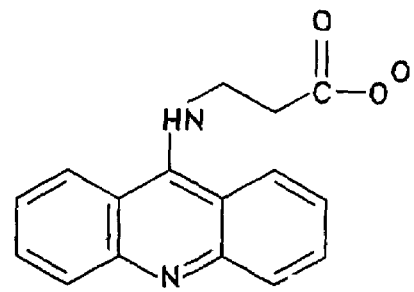
5-[(β-carboxyethyl)amino]acridine
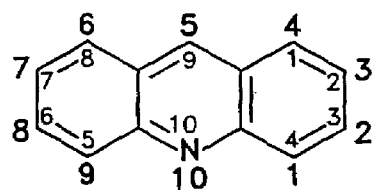
Acridine
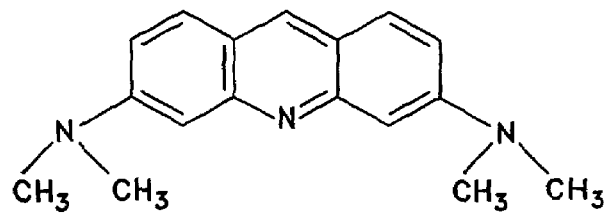
Acridine Orange
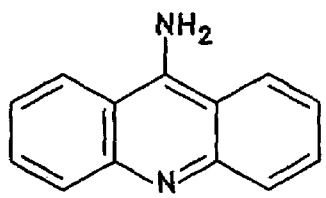
9-Amino Acridine
Fig. 12

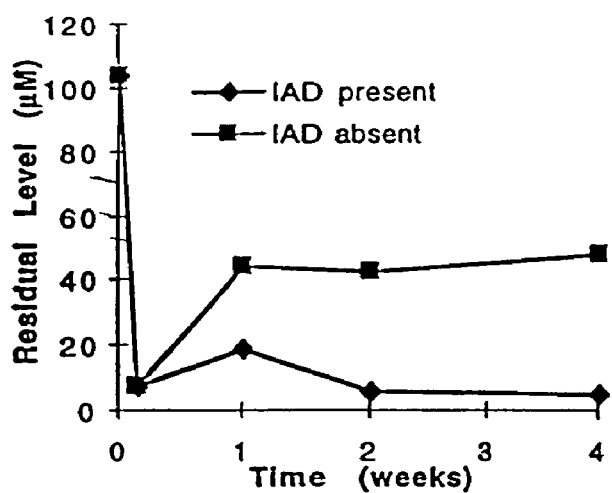
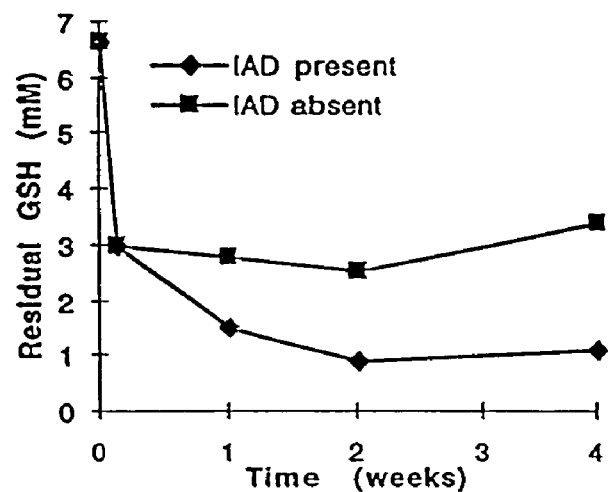
Figure 18

ADSORBING PATHOGEN-INACTIVATING COMPOUNDS WITH POROUS PARTICLES IMMOBILIZED IN A MATRIX

CROSS-REFERENCE TO RELATED APPLICATIONS

This application is a continuation-in-part of application Ser. No. 10/011,202, filed Dec. 7, 2001, now abandoned, which is a continuation of application Ser. No. 09/112,400 filed Jul. 8, 1998 now abandoned, which is a continuation-in-part of application Ser. No. 09/003,113, filed Jan. 6, 1998 now abandoned. This application is also continuation-in-part of application Ser. No. 10/016,323, filed Dec. 10, 2001, now U.S. Pat. No. 6,951,713 which is a continuation of application Ser. No. 09/112,068, filed Jul. 8, 1998, now abandoned, which is a continuation-in-part of application Ser. No. 09/003,113, filed Jan. 6, 1998, now abandoned. All of the applications disclosed above are incorporated by reference in their entirety.

TECHNICAL FIELD

The present invention relates to methods and devices for the reduction of compounds in biological compositions. The compounds have a molecular weight ranging from about 100 g/mol to about 30,000 g/mol.

BACKGROUND ART

An extensive body of research exists regarding the removal of substances from blood products. The bulk of this research is directed at white cell reduction. See, e.g., M. N. Boomgaard et al., *Transfusion* 34:311 (1994); F. Bertolini et al., *Vox Sang* 62:82 (1992); and A. M. Joustra-Dijkhuis et al., *Vox Sang* 67:22 (1994). Filtration of platelets is the most common method used in white cell reduction of platelet concentrates. See, e.g., M. Böck et al., *Transfusion* 31:333 (1991) (Sepacell PL-5A, Asahi, Tokyo, Japan); J. D. Sweeney et al., *Transfusion* 35:131 (1995) (Leukotrap P L, Miles Inc., Covina, Calif.); and M. van Marwijk et al., *Transfusion* 30:34 (1990) (Cellselect, NPBI, Emmer-Compascuum, The Netherlands; Immugard Ig-500, Terumo, Tokyo, Japan). These current filtration mechanisms, however are not amenable for the removal of relatively low molecular weight compounds including for example psoralens, psoralen photoproducts and other compounds commonly used in treating biological fluids.

The process of adsorption has been used to isolate selective blood components onto phospholipid polymers. For example, several copolymers with various electrical charges have been evaluated for their interactions with blood components, including platelet adhesion and protein adsorption. K. Ishihara et al., *J. Biomed. Mat. Res.* 28:1347 (1994). Such polymers, however, are not designed for the adsorption of low molecular weight compounds.

Various dialysis means are able to remove low molecular weight compounds from plasma and whole blood. For example, dialysis can successfully remove low molecular weight toxins and pharmaceutical compounds. Thus, dialysis might be used to remove, for example, psoralens and psoralen photoproducts from blood products. Unfortunately, current dialysis procedures involve very complicated and expensive devices. As such, the use of dialysis machines would not be practical for the decontamination of a large volume of blood products.

The use of polystyrene divinylbenzene, silica gel, and acrylester polymers for the adsorption of methylene blue has previously been described. For example, PCT Publication No. WO 91/03933 describes batch studies with free adsorbent resin (e.g., Amberlites (Rohm and Haas (Frankfurt, Germany) and Bio Beads (Bio-Rad Laboratories (Munich, Germany)). Without very careful removal of the adsorbent resins after exposure to the blood product, however, these methods create the risk of transfusion of the resin particles.

In addition, devices and processes for the removal of leukocytes and viral inactivation agents (e.g., psoralens, hypericin, and dyes such as methylene blue, toluidine blue, and crystal violet) have also been disclosed. Specifically, PCT Publication No. WO 95/18665 describes a filter comprising a laid textile web which includes a mechanically stable polymeric substrate. The web itself comprises interlocked textile fibers forming a matrix with spaces and fibrillated particles disposed within the spaces. However, this device causes a significant decrease in the Factor XI activity, which may render the treated product unsuitable for its intended use.

Simpler, safer and more economical means for reducing the concentration of low molecular weight compounds in a biological composition containing cells while substantially maintaining the biological activity of the treated biological composition containing cells are therefore needed.

DISCLOSURE OF THE INVENTION

The present invention provides devices for reducing the concentration of compounds in biological compositions containing cells. The devices include an adsorption medium comprised of particles immobilized by an inert matrix and are of a batch configuration. Typically, the compounds reduced in biological compositions using the device have molecular weights ranging from about 100 g/mol to about 30,000 g/mol. The biological composition containing cells includes, for example, cells suspended in a biological medium, such as plasma or tissue culture media. The biological activity of the biological composition is substantially maintained after contact with such devices.

Exemplary compounds include pathogen inactivating compounds, dyes, thiols, plasticizers and activated complement. Devices are provided that comprise a three dimensional network of adsorbent particles immobilized by an inert matrix. This immobilization reduces the risk of leakage of loose adsorbent particles into the blood product. Furthermore, immobilization of the adsorbent particles by an inert matrix simplifies manufacturing by reducing problems associated with handling loose adsorbent particles. Immobilization of the adsorbent particles may also enhance the ability of the adsorbent particles to adsorb compounds in biological compositions containing cells without mechanical damage to the cells.

The present invention provides a device for reducing the concentration of low molecular weight compounds in a biological composition containing cells such that the cells are suitable for their intended use.

In one embodiment, the device comprises an inert matrix containing highly adsorbent particles having a diameter ranging from about 100 µm to about 1500 µm. The cells in the biological composition treated with the device substantially maintain their desired biological activity. The device is for use in a batch process.

In another embodiment, the device further comprises a container that is compatible with the biological composition.

In another embodiment, the adsorbent particles have a surface area greater than about 750 m$^2$/g.

In another embodiment, the adsorbent particles have a surface area between about 1000 m²/g and 3000 m²/g.

In another embodiment, the adsorbent particles are polyaromatic adsorbent particles.

In another embodiment, the polyaromatic adsorbent particles possess superior wetting properties.

In another embodiment, the polyaromatic adsorbent particles comprise a hypercrosslinked polystyrene network.

In another embodiment, the adsorbent particles are activated carbon particles.

In another embodiment, the activated carbon particles are derived from a synthetic source.

In another embodiment, the low molecular weight compound is a quencher.

In another embodiment, the activated carbon particles are roughly spherical and are of a diameter ranging from about 300 μm to about 900 μm.

In another embodiment, the inert matrix is a synthetic polymer fiber.

In another embodiment, the synthetic polymeric fiber comprises a polymer core with a high melting temperature surrounded by a sheath with a lower melting temperature.

In another embodiment, the inert matrix is a particulate network.

In another embodiment, the particulate network comprises polyethylene particles.

In another embodiment, the adsorbent particles are immobilized in the matrix.

In another embodiment, the low molecular weight compound is a nucleic acid targeting agent or a photosensitizer.

In another embodiment, the low molecular weight compound is an acridine derivative, a psoralen derivative or a dye.

In another embodiment, the low molecular weight compound is a biological response modifier.

In another embodiment, the biological response modifier is activated complement.

In another embodiment, the low molecular weight compound is a quencher.

In another embodiment, the low molecular weight compound is a polyamine derivative.

In another embodiment, the desired biological activity maintained by the cells is suitability for infusion.

In another embodiment, the biological composition comprises platelets.

In another embodiment, treatment of the biological composition with a device over a period of about 5 days results in less than about a 10% loss in platelet count.

In another embodiment, the device comprises an inert matrix containing highly adsorbent particles having a diameter ranging from about 100 μm to about 1500 μm. The cells in the biological composition treated with the device substantially maintain their desired biological activity. The device is for use in a batch process. The biological composition comprises platelets. Treatment of the biological composition with the device over a period of about 5 days results in less than about a 10% loss in platelet count. The device further comprises a container that is compatible with the biological composition, and wherein the inert matrix is a synthetic polymer fiber comprising a polymer core with a high melting point surrounded by a sheath with a lower melting temperature, and wherein the adsorbent particles are polyaromatic adsorbents comprising a hypercrosslinked polystyrene network, and wherein the surface area of the particles is greater than about 750 m²/g, and wherein the adsorbent particles are immobilized in the matrix. An example of desired biological activity maintained by the cells includes, without limitation, suitability for infusion. Examples of low molecular weight compounds reduced by the device include, without limitation, an acridine derivative, a psoralen derivative, a dye and a biological response modifier such as activated complement. A device of this embodiment, as an example, may be used to treat the biological composition at a temperature of 22° C. for between about 0.5 hour and about 7 days.

In another embodiment, the biological composition comprises red blood cells.

In another embodiment, treatment of the biological composition with the device over a period of up to 35 days results in less than about 1% hemolysis.

In another embodiment, the device comprises an inert matrix containing highly adsorbent particles. The cells in the biological composition treated with the device substantially maintain their desired biological activity. The device is for use in a batch process. The biological composition comprises red blood cells. Treatment of the biological composition with the device over a period of up to 35 days results in less than about 1% hemolysis. The device further comprises a container that is compatible with the biological composition, and wherein the inert matrix is a synthetic polymer fiber comprising a polymer core with a high melting point surrounded by a sheath with a lower melting temperature, and wherein the adsorbent particles are activated carbon particles derived from a synthetic source, and wherein the diameter of the particles ranges from about 300 μm to about 900 μm, and wherein the surface area of the particles is greater than about 750 m²/g, and wherein the adsorbent particles are immobilized in the matrix. An example of desired biological activity maintained by the cells includes, without limitation, suitability for infusion. Examples of low molecular weight compounds reduced by the device include, without limitation, an acridine derivative, a psoralen derivative, a dye, a biological response modifier such as activated complement, and a quencher such as glutathione.

The present invention also provides a method for reducing the concentration of a low molecular weight compound in a biological composition containing cells, wherein the cells in the biological composition treated with a device substantially maintain their desired biological activity after treatment for between 0.5 hour and 5 weeks.

In one embodiment, the device comprises an inert matrix containing highly adsorbent particles having a diameter ranging from about 100 μm to about 1500 μm. The cells in the biological composition treated with the device substantially maintain their desired biological activity. The device is for use in a batch process.

In another embodiment, the device comprises an inert matrix containing highly adsorbent particles having a diameter ranging from about 100 μm to about 1500 μm. The cells in the biological composition treated with the device substantially maintain their desired biological activity. The device is for use in a batch process. The biological composition comprises platelets. Treatment of the biological composition with the device over a period of about 5 days results in less than about a 10% loss in platelet count. The device further comprises a container that is compatible with the biological composition, and wherein the inert matrix is a synthetic polymer fiber comprising a polymer core with a high melting point surrounded by a sheath with a lower melting temperature, and wherein the adsorbent particles are polyaromatic adsorbents comprising a hypercrosslinked polystyrene network, and wherein the surface area of the particles is greater than about 750 m²/g, and wherein the adsorbent particles are immobilized in the matrix.

In another embodiment, the device comprises an inert matrix containing highly adsorbent particles. The cells in the biological composition treated with the device substantially maintain their desired biological activity. The device is for use in a batch process. The biological composition comprises red blood cells. Treatment of the biological composition with the device over a period of up to 35 days results in less than about 1% hemolysis. The device further comprises a container that is compatible with the biological composition, and wherein the inert matrix is a synthetic polymer fiber comprising a polymer core with a high melting point surrounded by a sheath with a lower melting temperature, and wherein the adsorbent particles are activated carbon particles derived from a synthetic source, and wherein the diameter of the particles ranges from about 300 µm to about 900 µm, and wherein the surface area of the particles is greater than about 750 $m^2$/g, and wherein the adsorbent particles are immobilized in the matrix.

In another embodiment, the cells in the biological composition treated with the device substantially maintain their desired biological activity after being treated with the device for between about 1.0 hour and 5 weeks.

In another embodiment, the low molecular weight compound is an acridine derivative, a psoralen derivative or a dye.

In another embodiment, the low molecular weight compound is a biological response modifier.

In another embodiment, the biological response modifier is activated complement.

In another embodiment, the biological composition is treated with the device at a temperature of about 22° C. for between about 0.5 and about 36 hours.

In another embodiment, the biological composition is treated with the device at a temperature of about 22° C. for between about 0.5 and about 24 hours.

In another embodiment, the biological composition is treated with the device at a temperature of about 22° C. for between about 0.5 and about 12 hours.

In another embodiment, the biological composition is treated with the device at a temperature of about 22° C. for between about 0.5 and about 24 hours and is subsequently treated with the device at a temperature of about 4° C. for up to 5 weeks.

The present invention also provides a composition containing cells, wherein the biological composition is suitable for infusion. The biological composition is produced by treating a biological composition containing cells with a device for a period between about 0.5 hour and 5 weeks.

In one embodiment, the device comprises an inert matrix containing highly adsorbent particles having a diameter ranging from about 100 µm to about 1500 µm. The cells in the biological composition treated with the device substantially maintain their desired biological activity. The device is for use in a batch process.

In another embodiment, the device comprises an inert matrix containing highly adsorbent particles having a diameter ranging from about 100 µm to about 1500 µm. The cells in the biological composition treated with the device substantially maintain their desired biological activity. The device is for use in a batch process. The biological composition comprises platelets. Treatment of the biological composition with the device over a period of about 5 days results in less than about a 10% loss in platelet count. The device further comprises a container that is compatible with the biological composition, and wherein the inert matrix is a synthetic polymer fiber comprising a polymer core with a high melting point surrounded by a sheath with a lower melting temperature, and wherein the adsorbent particles are polyaromatic adsorbents comprising a hypercrosslinked polystyrene network, and wherein the surface area of the particles is greater than about 750 $m^2$/g, and wherein the adsorbent particles are immobilized in the matrix.

In another embodiment, the device comprises an inert matrix containing highly adsorbent particles. The cells in the biological composition treated with the device substantially maintain their desired biological activity. The device is for use in a batch process. The biological composition comprises red blood cells.

Treatment of the biological composition with the device over a period of up to 35 days results in less than about 1% hemolysis. The device further comprises a container that is compatible with the biological composition, and wherein the inert matrix is a synthetic polymer fiber comprising a polymer core with a high melting point surrounded by a sheath with a lower melting temperature, and wherein the adsorbent particles are activated carbon particles derived from a synthetic source, and wherein the diameter of the particles ranges from about 300 µm to about 900 µm, and wherein the surface area of the particles is greater than about 750 $m^2$/g, and wherein the adsorbent particles are immobilized in the matrix.

The present invention also provides a device for reducing the concentration of small organic compounds in a blood product while substantially maintaining a desired biological activity of the blood product.

In one embodiment, the device comprises highly porous adsorbent particles, wherein the adsorbent particles are immobilized by an inert matrix.

The adsorbent particles may be immobilized within a sintered matrix formed from polymeric particulate material.

Also disclosed is a pathogen-inactivating compound adsorption system configured to remove the pathogen-inactivating compound in a flow process. The diameter of adsorbent particles of this system ranges from about 1 micron to about 200 micron, and the adsorbent particles are immobilized within a sintered matrix formed from polymeric particulate material. The system further comprises a particle retention medium downstream of the adsorption medium, wherein the particle retention medium retains particles shed from the adsorption medium.

BRIEF DESCRIPTION OF THE DRAWINGS

FIG. 12 depicts the chemical structures of acridine, acridine orange, 9-amino acridine, and 5-[(β-carboxyethyl)amino]acridine.

FIG. 18 is a graph showing a comparison of the levels of 5-[(β-carboxyethyl)amino]acridine and GSH in the supernatant of 300 mL PRBC units with continued or terminated exposure after 24 hours to a fiberized Pica G277 IAD (500 g/m$^2$) over 4 weeks of storage at 4° C.

BEST MODE FOR CARRYING OUT THE INVENTION

Figure 1:
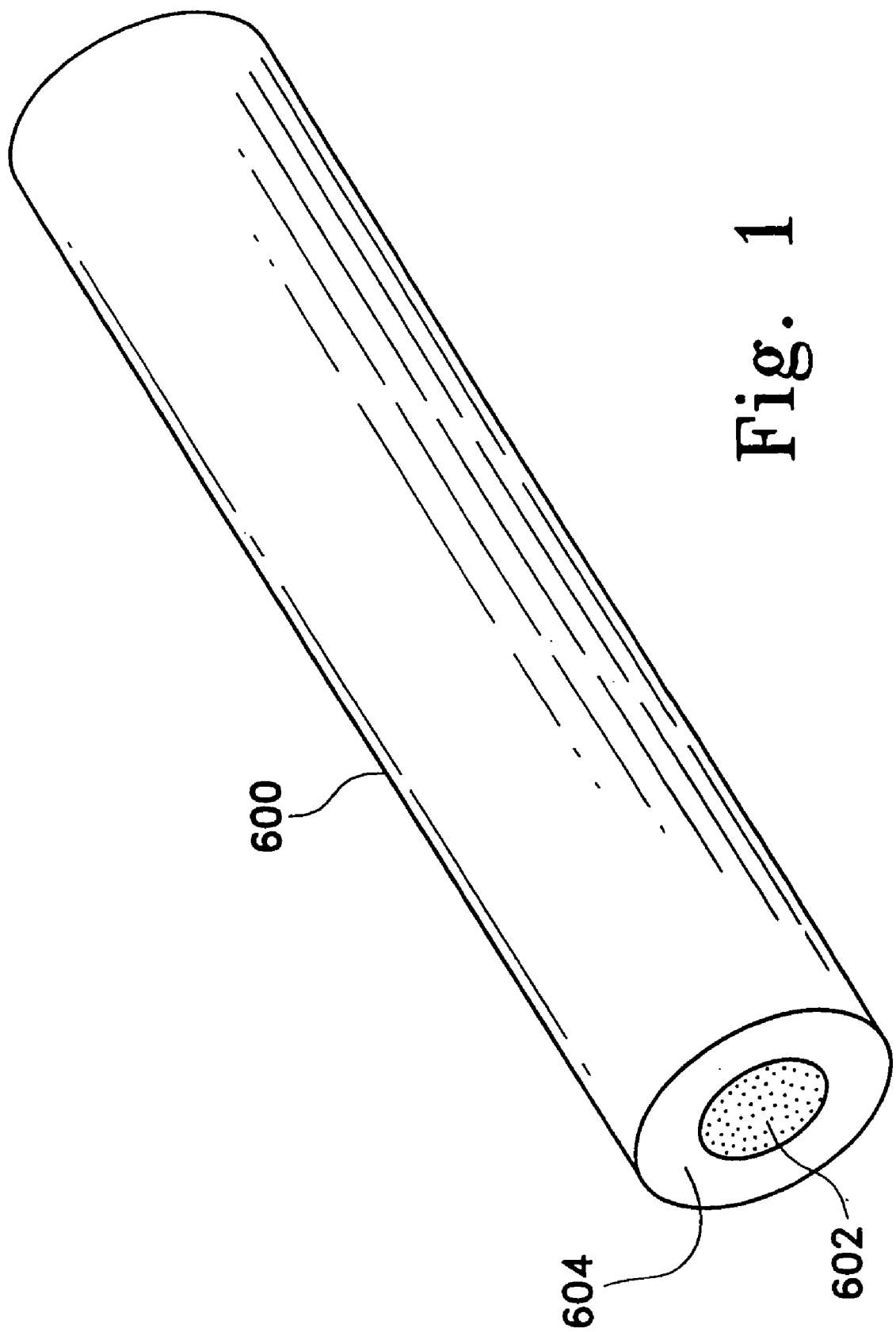
FIG. 1 diagrammatically depicts a perspective view of one embodiment of a fiber, indicating its inner core and outer sheath, that forms the fiber networks of the immobilized adsorbent media.

The present invention provides devices for reducing the concentration of compounds in biological compositions containing cells. The devices include an adsorption medium comprised of particles immobilized by an inert matrix and are of a batch configuration. Typically, the compounds reduced in biological compositions using the device have molecular weights ranging from about 100 g/mol to about 30,000 g/mol. The biological composition containing cells includes, for example, cells suspended in a biological medium, such as plasma or tissue culture media. The biological activity of the biological composition is substantially maintained after contact with such devices.

Exemplary compounds include pathogen inactivating compounds, dyes, thiols, plasticizers and activated complement. Devices are provided that comprise a three dimensional network of adsorbent particles immobilized by an inert matrix. This immobilization reduces the risk of leakage of loose adsorbent particles into the blood product. Furthermore, immobilization of the adsorbent particles by an inert matrix simplifies manufacturing by reducing problems associated with handling loose adsorbent particles. Immobilization of the adsorbent particles may also enhance the ability of the adsorbent particles to adsorb compounds in biological compositions containing cells without mechanical damage to the cells.

Definitions

The term "acridine derivatives" refer to a chemical compound containing the tricyclic structure of acridine (dibenzo[b,e]pyridine; 10-azanthracene). The compounds have an affinity for (and can bind) to nucleic acids non-covalently through intercalation. The term "aminoacridine" refers to those acridine compounds with one or more nitrogen-containing functional groups. Examples of aminoacridines include 9-amino acridine and acridine orange (depicted in FIG. 12).

The term "adsorbent particle" broadly refers to any natural or synthetic particulate material which is capable of interacting with molecules in a liquid thus allowing the molecule to be removed from the liquid. Examples of naturally occurring adsorbents include but are not limited to activated carbon, silica, diatomaceous earth, and cellulose. Examples of synthetic adsorbents include but are not limited to polystyrene, polyacrylics, and carbonaceous adsorbents.

Adsorbent particles are often porous, often possess high surface areas, and may be modified with a variety of functional groups (e.g. ionic, hydrophobic, acidic, basic) which can affect how the adsorbent interacts with molecules.

The term "aromatic," "aromatic compounds," and the like refer broadly to compounds with rings of atoms having delocalized electrons. The monocyclic compound benzene ($C_6H_6$) is a common aromatic compound. However, electron delocalization can occur over more than one adjacent ring (e.g., naphthalene (two rings) and anthracene (three rings)). Different classes of aromatic compounds include, but are not limited to, aromatic halides (aryl halides), aromatic heterocyclic compounds, aromatic hydrocarbons (arenes), and aromatic nitro compounds (aryl nitro compounds).

The term "biocompatible coating" refers broadly to the covering of a surface (e.g., the surface of a polystyrene bead) with a hydrophilic polymer that when in contact with a blood product does not result in an injurious, toxic, or immunological response and renders the surface more biocompatible by decreasing cell adhesion, decreasing protein adsorption or improving cell function. Suitable coatings are biocompatible if they have minimal, if any, effect on the biological material to be exposed to them. By "minimal" effect it is meant that no significant biological difference is seen compared to the control. In preferred embodiments, biocompatible coatings improve the surface hemocompatibility of polymeric structures. For example, poly(2-hydroxyethyl methacrylate) (pHEMA) is frequently used for the coating of materials used in medical devices (e.g., blood filters).

The term "biocompatible housing" refers broadly to containers, bags, vessels, receptacles, and the like that are suitable for containing a biological material, such as, for example, compositions containing platelets or red blood cells. Suitable containers are biocompatible if they have minimal, if any, effect on the biological material to be contained therein. By "minimal" effect it is meant that no significant difference is seen in blood product function compared to the control as described herein, for red blood cells, platelets and plasma. Thus, blood products may be stored in biocompatible housings prior to transfusion to a recipient. In a preferred embodiment, biocompatible housings are blood bags, including a platelet storage container or red blood cell storage container.

The term "container that is compatible with the biological composition" refers to a container that is suitable for holding a biological composition containing cells, such as, for example, cell culture compositions, as well as compositions containing platelets or red blood cells. Such containers have a minimal effect on a biological composition containing cells. Examples of such containers include, without limitation, cell culture plates, cell culture bottles and blood bags.

The term "biological fluids" include media from cell cultures, synthetic media for the storage of cells, human or non-human whole blood, plasma, platelets, red blood cells, leukocytes, serum, lymph, saliva, milk, urine, or products derived from or containing any of the above, alone or in mixture, with or without a chemical additive solution. Preferably, the fluid is blood or a blood product with or without a chemical additive solution, more preferably plasma, platelets and red blood cells, most preferably apheresis plasma, red blood cells and platelets.

The term "blood bag" refers to a form of blood product container.

The term "blood product" refers to the fluid and/or associated cellular elements and the like (such as erythrocytes, leukocytes, platelets, etc.) that pass through the body's circulatory system; blood products include, but are not limited to, blood cells, platelet mixtures, serum, and plasma. The term "platelet mixture" refers to one type of blood product wherein the cellular element is primarily or only platelets. A platelet concentrate (PC) is one type of platelet mixture where the platelets are associated with a smaller than normal portion of plasma. In blood products, synthetic media may make up that volume normally occupied by plasma; for example, a platelet concentrate may entail platelets suspended in 35% plasma/65% synthetic media. Frequently, the synthetic media comprises phosphate.

The term "blood separation means" refers broadly to a device, machine, or the like that is able to separate blood into blood products (e.g., platelets and plasma). An apheresis system is one type of blood separation means. Apheresis systems generally comprise a blood separation device, an intricate network of tubing and filters, collection bags, an anticoagulant, and a computerized means of controlling all of the components.

The term "crosslinked" refers broadly to linear molecules that are attached to each other to form a two- or three-dimensional network. For example, divinylbenzene (DVB) serves as the crosslinking agent in the formation of styrene-divinylbenzene copolymers. The term also encompasses "hypercrosslinking" in which hypercrosslinked networks are produced by crosslinking linear polystyrene chains either in solution or in a swollen state with bifunctional agents. A variety of bifunctional agents can be used for cross-linking (for example, see Davankov and Tsyurupa, Reactive Polymers 13:24-42 (1990); Tsyurupa et al., Reactive Polymers 25:69-78 (1995).

The term "cyclic compounds" refers to compounds having one (i.e., a monocyclic compounds) or more than one (i.e., polycyclic compounds) ring of atoms. The term is not limited to compounds with rings containing a particular number of atoms. While most cyclic compounds contain rings with five or six atoms, rings with other numbers of atoms (e.g., three or four atoms) are also contemplated by the present invention. The identity of the atoms in the rings is not limited, though the atoms are usually predominantly carbon atoms. Generally speaking, the rings of polycyclic compounds are adjacent to one another; however, the term "polycyclic" compound includes those compounds containing multiple rings that are not adjacent to each other.

The term "dye" refers broadly to compounds that impart color. Dyes generally comprise chromophore and auxochrome groups attached to one or more cyclic compounds. The color is due to the chromophore, while the dying affinities are due to the auxochrome. Dyes have been grouped into many categories, including the azin dyes (e.g., neutral red, safranin, and azocarmine B); the azo dyes; the azocarmine dyes; the dephenymethane dyes; the fluorescein dyes; the ketonimine dyes; the rosanilin dyes; the triphenylmethane dyes; the phthalocyanines; and, hypericin. It is contemplated that the methods and devices of the present invention may be practiced in conjunction with any dye that is a cyclic compound.

The term "fiberized resin" generally refers to immobilization of adsorbent material, including for example, resins entrapped in or attached to a fiber network. In one embodiment, the fiber network is comprised of polymer fibers. In another embodiment, the fibers consist of a polymer core (e.g., polyethylene terephthalate [PET]) with a high melting point surrounded by a polymer sheath (e.g., nylon or modified PET) with a relatively low melting temperature. Fiberized resin may be produced by heating the fiber network, under conditions that do not adversely affect the adsorbent capacity of the resin to a significant degree (temperature sufficient to melt the sheath but not the core). Where the resin comprises beads, heating is performed such that the adsorbent beads become attached to the outer polymer sheath to create "fiberized beads". By producing fiberized resin containing a known amount of adsorbent beads per defined area, samples of fiberized resin for use in the removal of cyclic compounds (e.g., psoralens, and, in particular, aminopsoralens) and other products can be obtained by cutting a defined area of the fiberized resin, rather than weighing the adsorbent beads.

The term "filter" refers broadly to devices, materials, and the like that are able to allow certain components of a mixture to pass through while retaining other components. For example, a filter may comprise a mesh with pores sized to allow a blood product (e.g. red blood cell composition) to pass through, while retaining other components such as resin particles. The term "filter" is not limited to the means by which certain components are retained.

The term "heterocyclic compounds" refers broadly to cyclic compounds wherein one or more of the rings contains more than one type of atom. In general, carbon represents the predominant atom, while the other atoms include, for example, nitrogen, sulfur, and oxygen. Examples of heterocyclic compounds include furan, pyrrole, thiophene, and pyridine.

The phrase "high temperature activation process" refers to a high temperature process that typically results in changes in surface area, porosity and surface chemistry of the treated material due to pyrolysis and/or oxidation of the starting material.

The term "Immobilized Adsorbent Device (IAD)" refers to immobilized adsorbent material entrapped in or attached to an inert matrix. Where the inert matrix is a fiber network the term IAD can be used interchangeably with the term fiberized resin. For example, fiberized Ambersorb 572 and Ambersorb LAD (AQF) refer to the same material.

The term "inert matrix" refers to any synthetic or naturally occurring fiber or polymeric material which can be used to immobilize adsorbent particles without substantially affecting the desired biological activity of the blood product. The matrix may contribute to the reduction in concentration of small organic compounds although typically it does not contribute substantially to the adsorption or removal process. In addition, the inert matrix may interact with cellular or protein components resulting in cell removal (e.g. leukodepletion) or removal of protein or other molecules.

The term "isolating" refers to separating a substance out of a mixture containing more than one component. For example, platelets may be separated from whole blood. The product that is isolated does not necessarily refer to the complete separation of that product from other components.

The term "macropores" generally means that the diameter of the pores is greater than about 500 Å. The term micropores refers to pores with diameters less than about 20 Å. The term mesopores refers to pores with diameters greater than about 20 Å. and less than about 500 Å.

The term "macroporous" is used to describe a porous structure having a substantial number of pores with diameters greater than about 500 Å.

The term "macroreticular" is a relative term that means that the structure has a high physical porosity (i.e., a large number of pores are present) a porous adsorbent structure possessing both macropores and micropores.

The term "mesh enclosure," "mesh pouch" and the like refer to an enclosure, pouch, bag or the like manufactured to contain multiple openings. For example, the present invention contemplates a pouch, containing the immobilized adsorbent particle, with openings of a size that allow a blood product to contact the immobilized adsorbent particle, but retain the immobilized adsorbent particle within the pouch.

The term "partition" refers to any type of device or element that can separate or divide a whole into sections or parts. For example, the present invention contemplates the use of a partition to divide a blood bag, adapted to contain a blood product, into two parts. The blood product occupies one part of the bag prior to and during treatment, while the adsorbent resin occupies the other part. In one embodiment, after treatment of the blood product, the partition is removed (e.g., the integrity of the partition is altered), thereby allowing the treated blood product to come in contact with the adsorbent resin. The partition may either be positioned in the bag's interior or on its exterior. When used with the term "partition," the term "removed" means that the isolation of the two parts of the blood bag no longer exists; it does not necessarily mean that the partition is no longer associated with the bag in some way.

The term "photoproduct" refers to products that result from the photochemical reaction that a psoralen or other dyes (e.g., methylene blue, phthalocyanine) undergo upon exposure to ultraviolet radiation.

The term "polyaromatic compounds" refers to polymeric compounds containing aromatic groups in the backbone, such as polyethylene terphalate, or as pendant groups, such as polystyrene, or both.

The term "polystyrene network" refers broadly to polymers containing styrene ($C_6H_5CH=CH_2$) monomers; the polymers may be linear, consisting of a single covalent alkane chain with phenyl substituents, or cross-linked, generally with m- or p-phenylene residues or other bifunctional or hypercrosslinked structure, to form a two-dimensional polymer backbone or 3D network.

The term "psoralen removal means" refers to a substance or device that is able to remove greater than about 80% of the psoralen from, e.g., a blood product; preferably, greater than about 90%; most preferably greater than about 99%. A psoralen removal means may also remove other components of the blood product, such as psoralen photoproducts.

The phrase "reducing the concentration" refers to the removal of some portion of low molecular weight compounds from a biological composition. While reduction in concentration is preferably on the order of greater than about 70%, more preferably on the order of about 90%, and most preferably on the order of about 99%.

The phrase "removing substantially all of said portion of a compound (e.g. a psoralen, psoralen derivative, isopsoralen, acridine, acridine derivative, dye, plasticizer or activated complement) free in solution" refers preferably to the removal of more than about 80% of the compound free in solution, more preferably to the removal of more than about 85%, even more preferably of more than about 90%, and most preferably to the removal of more than about 99%.

The term "resin" refers to a solid support (such as particles or beads etc.) capable of interacting and adsorbing to various small organic compounds, including psoralens, in a solution or fluid (e.g., a blood product), thereby decreasing the concentration of those elements in solution. The removal process is not limited to any particular mechanism. For example, a psoralen may be removed by hydrophobic or ionic interaction. The term "adsorbent resin" refers broadly to both natural organic substances and synthetic substances and to mixtures thereof.

The term "agitation means" refers to any method by which a biological composition can be mixed. Examples of agitation means include, without limitation, the following mechanical agitators: reciprocating, orbital, 3-D rotator and rotator type agitators.

The term "shaker device" refers to any type of device capable of thoroughly mixing a blood product like a platelet concentrate. The device may have a timing mechanism to allow mixing to be restricted to a particular duration.

The term "sintered medium" refers to a structure which is formed by applying heat and pressure to a porous resin, including for example a particulate thermoplastic polymer. Porous resins can be prepared by mixing particulate of relatively low melting polymers and heating them so the plastic particles partially fuse but still allow a path for fluids to penetrate the porous mass. Sintered adsorbent media can be prepared similarly by incorporating carbon or other high or non-melting adsorbent particle with that of the low melting powder and heating. Methods of producing porous plastic materials are described in U.S. Pat. Nos. 3,975,481, 4,110, 391, 4,460,530, 4,880,843 and 4,925,880, incorporated by reference herein. The process causes fusing of the low melting particles resulting in the formation of a porous solid structure. The sintered medium can be formed into a variety of shapes by placing the polymer particles in a forming tool during the sintering process. Adsorbent particles can be introduced into the sintered medium by mixing adsorbent particles with the thermoplastic polymer particles before subjecting to the sintering process.

The term "stabilizing agent" refers to a compound or composition capable of maintaining the adsorption capacity of certain adsorbents (e.g., Amberlites) under drying conditions. Generally speaking, acceptable stabilizing agents should be soluble in water and ethanol (or other wetting agents), nonvolatile relative to water and ethanol, and safe for transfusion in small amounts. Examples of stabilizing agents include, but are not limited to, glycerol and low molecular weight PEGs. A "wetting agent" is distinguishable from a "stabilizing agent" in that the former is believed to reopen adsorbent pores of those resins that are not hypercrosslinked (e.g., Amberlite XAD-4, Amberlite XAD-16). Wetting agents generally will not prevent pores from collapsing under drying conditions, whereas stabilizing agents will. A general discussion of wetting and wetting agents is set forth in U.S. Pat. No. 5,501,795 to Pall et al., hereby incorporated by reference.

The phrase "substantially maintaining a desired biological activity of the biological composition" refers to substantially maintaining properties (e.g., cellular integrity) of the biological composition. In some embodiments, the cellular integrity is reflective of the potential performance of the composition in a therapeutic setting. For example, where red blood cells are concerned, in vivo activity is not destroyed or significantly lowered if ATP levels, extracellular potassium leakage, % hemolysis are substantially maintained in red blood cells treated by the methods described herein. For example, the change in ATP level of the treated red blood cells should be less than about 10%. The hemolysis level in the treated red blood cells following storage should be less than about 1%, preferably less than about 0.8%. The change in extracellular potassium leakage of the treated red blood cells should be less than about 15%. Where platelets are concerned, in vivo activity is not destroyed or significantly lowered if, for example, platelet yield, pH, aggregation response, shape change, GMP-140, morphology or hypotonic shock response are substantially maintained in platelets treated by the methods described herein. For example, platelet loss in a biological composition after storage is preferably less than 15%; more preferably 15% after 5 days storage; even more preferably 10% after 5 days storage. It is further contemplated that the phrase substantially maintained for each of the properties associated with a described blood products may also include values acceptable to those of ordinary skill in the art as described in the literature, including for example in Klein H. G., ed. Standards for Blood Banks and Transfusion Services, 17$^{th}$ Ed., Bethesda, Md.: American Association of Blood Banks, 1996, incorporated by reference herein.

The term "equivalent thereto" when used in reference to a device of the present invention refers to a device that functions equivalently with respect to the maintenance of biological activity of a biological composition. For example, an "equivalent" device or matrix containing adsorbent particles is one that similarly maintains cell viability or a suitable coagulation factor level.

The term "low molecular weight compound" refers to an organic or biological molecule having a molecular weight ranging from about 100 g/mol to about 30,000 g/mol. Low molecular weight compounds include, without limitation, the following compounds: small organic compounds such as psoralens, acridines or dyes; quenchers, such as glutathione; plastic extractables, such as plasticizers; biological modifiers, such as activated complement, that possess a molecular weight between about 100 g/mol and about 30,000 g/mol; and, polyamine derivatives.

The term "biological composition that is suitable for infusion" refers to a biological composition that maintains its essential biological properties (e.g. platelet morphology) while having sufficiently low levels of any undesired compounds (e.g. inactivation compounds, response modifiers) such that infusion provides intended function without detrimental side effects.

The term "control," as used in phrases such as "relative to control," refers to an experiment performed to study the relative effects of different conditions. For example, where a biological composition is treated with a device, "untreated control" would refer to the biological composition treated under the same conditions except for the absence of treatment with the device, or treated with an alternative form of a device (e.g., immobilized particles vs. non-immobilized particles).

The term "4'-(4-amino-2-oxa)butyl-4,5',8-trimethyl psoralen" is alternatively referred to as "S-59."

The term "N-(9-acridinyl)-β-alanine" is alternatively referred to as "5-[(β-carboxyethyl)amino]acridine." It is further alternatively referred to as "S-300."

The term "XUS-43493" is alternatively referred to as "Optipore 493."

Adsorbent Particles

Provided are adsorbent particles which are useful in a device for reducing the concentration of compounds in a biological composition containing cells while substantially maintaining a desired biological activity of the biological composition. Typically, the compounds that are reduced in the biological composition have molecular weights ranging from about 100 g/mol to about 30,000 g/mol.

The adsorbent particles can be of any regular or irregular shape that lends itself to incorporation into the inert matrix but are preferably roughly spherical. The particles are greater than about 100 μm in diameter and less than about 1500 μm in diameter; preferably, the particles are between about 200 μm and about 1300 μm in diameter; more preferably, the particles are between about 300 μm and about 900 μm in diameter.

A high surface area is characteristic of the particles. Preferably, the particles have a surface area between about 750 m$^2$/g and about 3000 m$^2$/g. More preferably, the particles have a surface area between about 1000 m$^2$/g and about 3000 m$^2$/g.

Adsorbent particles suitable for use in the device of the present invention can be any suitable material, with the limitation that the material does not substantially adversely affect the biological activity of a biological composition upon contact. The adsorbent particle can be, for example, made of materials such as activated carbon, hydrophobic resins or ion exchange resins.

In one preferred embodiment the adsorbent particles are activated carbons derived either from natural or synthetic sources. Preferably the activated carbons are derived from synthetic sources. Nonlimiting examples of activated carbons include; Picatiff Medicinal®, which is available from PICA USA Inc. (Columbus, Ohio), Norit® ROX 0.8, which is available from Norit Americas, Inc. (Atlanta, Ga.), Ambersorb® 572, which is available from Rohm & Haas (Philadelphia, Pa.), and G-277®, which is available from PICA (Columbus, Ohio).

In another preferred embodiment, the particles can be hydrophobic resins. Nonlimiting examples of hydrophobic resins include the following polyaromatic adsorbents: Amberlite® adsorbents (e.g., Amberlite® XAD-2, XAD-4, and XAD-16), available from Rohm and Haas (Philadelphia, Pa.); Amberchrom® adsorbents available from Toso Haas (TosoHass, Montgomeryville, Pa.); Diaion®//Sepabeads® Adsorbents (e.g., Diaion® HP20), available from Mitsubishi Chemical America, Inc. (White Plains, N.Y.); Hypersol-Macronet® Sorbent Resins (e.g., Hypersol-Macronet® Sorbent Resins MN-200, MN-150 and MN-400) available from Purolite (Bala Cynwyd, Pa.); and Dowex® Adsorbents (e.g., Dowex® XUS-40323, XUS-43493, and XUS-40285), available from Dow Chemical Company (Midland, Mich.).

Preferred particles are-hydrophobic resins which are polyaromatic adsorbents comprising a hypercrosslinked polystyrene network, such as Dowex® XUS-43493 (known commercially as Optipore® L493 or V493) and Purolite MN-200.

Hypercrosslinked polystyrene networks, such as Dowex® XUS-43493 and Purolite MN-200 are non-ionic macroporous and macroreticular resins. The non-ionic macroreticular and macroporous Dowex® XUS-43493 has a high affinity for psoralens, including for example, 4'-(4-amino-2-oxa)butyl-4,5',8-trimethyl psoralen, and it possesses superior wetting properties. The phrase "superior wetting properties" means that dry (i.e. essentially anhydrous) adsorbent does not need to be wet with a wetting agent (e.g., ethanol) prior to being contacted with the blood product in order for the adsorbent to effectively reduce the concentration of small organic compounds from the blood product.

Hypercrosslinked polystyrene networks, such as Dowex® XUS-43493 and Purolite MN-200 are preferably in the form of spherical particles with a diameter range of about 200 µm to about 1300 µm. Adsorbent particles, including for example, Dowex® XUS-43493, preferably have extremely high internal surface areas and relatively small pores (e.g. average diameter 46 Å). The internal surface area of the particle can be from about 300 to about 1100 $m^2/g$; preferably about 900 to about 1100 $m^2/g$; most preferably about 1100 $m^2/g$. The majority of the pores of the particle can be greater than 25 Å and less than 800 Å; preferably from about 25 Å to about 150 Å; most preferably from about 25 Å to about 50 Å. While it is not intended that the present invention be limited to the mechanism by which reduction of small organic compounds takes place, hydrophobic interaction is believed to be the primary mechanism of adsorption. Its porous nature confers selectively on the adsorption process by allowing small molecules to access a greater proportion of the surface area relative to large molecules (i.e., large proteins) and cells. Purolite® has many similar characteristics to Dowex® XUS-43493, such as high affinity for psoralens and superior wetting properties, and is also a preferred adsorbent particle.

Polystyrene particles can be classified, based on their mechanism of synthesis and physical and functional characteristics, as i) conventional networks and ii) hypercrosslinked networks. Preferred adsorbents have a high surface area, have pores that do not collapse upon drying, do not require wetting for biological compositions comprising red blood cells or platelets, and have extremely low levels of small particles and foreign particles (e.g. dust, fibers, non-adsorbent particles, and unidentified particles). In addition, preferred adsorbents have low levels of extractable residual monomer, crosslinkers and other organic extractables.

The conventional networks are primarily styrene-divinylbenzene copolymers in which divinylbenzene (DVB) serves as the crosslinking agent (i.e., the agent that links linear polystyrene chains together). These polymeric networks include the "gel-type" polymers. The gel-type polymers are homogeneous, non-porous styrene-DVB copolymers obtained by copolymerization of monomers. The macroporous adsorbents represent a second class of conventional networks. They are obtained by copolymerization of monomers in the presence of diluents that precipitate the growing polystyrene chains. The polystyrene network formed by this procedure possess a relatively large internal surface area (up to hundreds of square meters per gram of polymer); Amberlite® XAD-4 is produced by such a procedure.

In contrast to the conventional networks described above, the preferred adsorbents of the present invention (e.g., Dowex® XUS-43493) are hypercrosslinked networks. These networks are produced by crosslinking linear polystyrene chains either in solution or in a swollen state with bifunctional agents; the preferred bifunctional agents produce conformationally-restricted crosslinking bridges, that are believed to prevent the pores from collapsing when the adsorbent is in an essentially anhydrous (i.e., "dry") state.

The hypercrosslinked networks are believed to possess three primary characteristics that distinguish them from the conventional networks. First, there is a low density of polymer chains because of the bridges that hold the polystyrene chains apart. As a result, the adsorbents generally have a relatively large porous surface area and pore diameter. Second, the networks are able to swell; that is, the volume of the polymer phase increases when it contacts organic molecules.

Finally, the hypercrosslinked polymers are "strained" when in the dry state; that is, the rigidity of the network in the dry state prevents chain-to-chain attractions.

However, the strains relax when the adsorbent is wetted, which increases the network's ability to swell in liquid media. Davankov and Tsyurupa, *Reactive Polymers* 13:27-42 (1990); Tsyurupa et al., *Reactive Polymers* 25:69-78 (1995), hereby incorporated by reference..

Several cross-linking agents have been successfully employed to produce the bridges between polystyrene chains, including p-xylene dichloride (XDC), monochlorodimethyl ether (MCDE), 1,4-bis-chloromethyldiphenyl (CMDP), 4,4'-bis-(chloromethyl)biphenyl (CMB), dimethylformal (DMF), p,p'-bis-chloromethyl-1,4-diphenylbutane (DPB), and tris-(chloromethyl)-mesitylene (CMM). The bridges are formed between polystyrene chains by reacting one of these cross-linking agents with the styrene phenyl rings by means of a Friedel-Crafts reaction. Thus, the resulting bridges link styrene phenol rings present on two different polystyrene chains. See, e.g., U.S. Pat. No. 3,729,457, hereby incorporated by reference.

The bridges are especially important because they generally eliminate the need for a "wetting" agent. That is, the bridges prevent the pores from collapsing when the adsorbent is in an essentially anhydrous (i.e., "dry") state, and thus they do not have to be "reopened" with a wetting agent prior to the adsorbent being contacted with a blood product. In order to prevent the pores from collapsing, conformationally-restricted bridges should be formed. Some bifunctional agents like DPB do not result in generally limited conformation; for example, DPB contains four successive methylene units that are susceptible to conformation rearrangements. Thus, DPB is not a preferred bifunctional agent for use with the present invention.

Some of the structurally-related characteristics of the above-described adsorbent particles are summarized in Table A.

TABLE A

| Resin | Chemical Nature | Mean Surface Area (m²/g) | Mean Pore Diam. (Å) | Mesh Size (μm) |
|---|---|---|---|---|
| Amberlite® Adsorbents - Rohm and Haas | | | | |
| XAD-2 | polyaromatic | 300 | 90 | 20-60 |
| XAD-4 | polyaromatic | 725 | 40 | 20-60 |
| XAD-7 | polymethacrylate | 450 | 90 | 20-60 |
| XAD-16 | polyaromatic | 800 | 100 | 20-60 |
| XAD-1180 | polyaromatic | 600 | 300 | 20-60 |
| XAD-2000 | polyaromatic | 580 | 42 | 20-60 |
| XAD-2010 | polyaromatic | 660 | 280 | 20-60 |
| Amberchrom® Adsorbents - Toso Haas | | | | |
| CG-71m | polymethacrylate | 450-550 | 200-300 | 50-100 |
| CG-71c | polymethacrylate | 450-550 | 200-300 | 80-160 |
| CG-161m | polyaromatic | 800-950 | 110-175 | 50-100 |
| CG-161c | polyaromatic | 800-950 | 110-175 | 80-160 |
| Diaion®//Sepabeads® Adsorbents - Mitsubishi Chemical | | | | |
| HP20 | polyaromatic | 500 | 300-600 | 20-60 |
| SP206 | brominated styrenic | 550 | 200-800 | 20-60 |
| SP207 | brominated styrenic | 650 | 100-300 | 20-60 |
| SP850 | polyaromatic | 1000 | 50-100 | 20-60 |
| HP2MG | polymethacrylate | 500 | 200-800 | 25-50 |
| HP20SS | polyaromatic | 500 | 300-600 | 75-150 |
| SP20MS | polyaromatic | 500 | 300-600 | 50-100 |
| Dowex® Adsorbents - Dow Chemical Company | | | | |
| XUS-40285 | functionalized | 800 | 25 | 20-50 |
| XUS-40323 | polyaromatic | 650 | 100 | 16-50 |
| XUS-43493 | polyaromatic | 1100 | 46 | 20-50 |

Processing the Adsorbent Particles

The adsorbent particles may be further processed to remove fine particles, salts, potential extractables, and endotoxin. The removal of these extractable components is typically performed by treatment with either organic solvents, steam, or supercritical fluids. Preferably the particles are sterilized.

Several companies currently sell "cleaned" (i.e., processed) versions of commercially available adsorbent particles. In addition to processing the adsorbent particles (e.g. resins), these companies test the adsorbents, and the final adsorbent is certified sterile (USP XXI), pyrogen-free (LAL), and free of detectable extractables (DVB and total organics).

Thermal processing (e.g., steam) is an effective method for processing adsorbent particles. F. Rodriguez, *Principles Of Polymer Systems*, (Hemisphere Publishing Corp.), pp. 449-53 (3rd. Ed., 1989). Supelco, Inc. (Bellefonte, Pa.) uses a non-solvent, thermal proprietary process to clean the Dowex® XUS-43493 and Amberlite adsorbents. The main advantage of using steam is that it does not add any potential extractables to the adsorbent. One big disadvantage, however, is that this process can strip water from the pores of the resin beads; effective performance of some adsorbents requires that the beads be re-wet prior to contacting the blood product.

One advantage of the cleaned/processed adsorbent is an extremely low level of particles with diameters less than 30 μm. Preliminary testing on adsorbents (Dowex® XUS-43493 and Amberlite® XAD-16) processed by Supelco was performed to determine particle counts. The results of these tests indicated that foreign particles (e.g., dust, fibers, non-adsorbent particles, and unidentified particles) were absent and that fine particles (<30 μm) were essentially absent.

The Use of Wetting Agents and Stabilizing Agents with Adsorbent Resins

Methods may be used for preventing drying and loss of adsorption capacity of particles, such as Amberlite® which lose some of their adsorption capacity under certain conditions (e.g., drying).

In one method, particles, materials or devices may be manufactured in a wet state which is sealed and not capable of drying. This method is associated with several important drawbacks. The shelf-life of the products could be reduced since levels of extractables from the materials could increase over time. Sterilization may be limited to a steam process because γ-irradiation of wet polymers is typically not performed. Manufacturing a device that requires that a component be maintained in a wet state is, in general, more difficult than manufacturing a dry device; for example, bioburden and endotoxin may become of concern if there is a long lag time between device assembly and terminal sterilization.

A second method for preventing loss of adsorption capacity involves the use of an adsorbent which is not adversely affected by drying. As previously set forth, macroreticular adsorbents possessing highly crosslinked porous structures (e.g., Dowex® XUS-43493 and Purolite® MN-200) generally do not require a wetting agent because the crosslinks prevent the pores from collapsing. Unlike Amberlite® XAD-16, these macroreticular adsorbents retain a very high proportion of their initial activity when they are dried.

In a third method, loss of adsorption capacity upon drying may be prevented by hydrating Amberlite® XAD-16 and related adsorbents (e.g., Amberlite® XAD-4) in the presence of a non-volatile wetting agent. For example, when using Amberlite® XAD-16 as the adsorbent, the adsorbent beads may partially dry prior to use during handling, sterilization, and storage. When the water content of these adsorbents drops below a critical level, a rapid loss in adsorption capacity occurs (probably due to "collapse" of the pores); thus, for optimum effectiveness, the pores have to be "reopened" with a wetting agent prior to use.

Stabilizing agents are effective in maintaining adsorption capacity near its maximum when certain adsorbent resins are subjected to drying conditions. It is believed that the use of stabilizing agents serves to prevent the adsorbent pores from collapsing.

An acceptable stabilizing agent should be soluble in water and ethanol, nonvolatile relative to ethanol and water, and safe for transfusion in small amounts. Glycerol and low molecular weight polyethylene glycol (e.g., PEG-200 and PEG-400) are examples of stabilizing agents possessing these characteristics. Glycerol has a positive hemocompatibility history. It is frequently added to blood as a cryo-preservative agent in the frozen storage of red blood cell preparations. See, e.g., Chaplin et al., Transfusion 26:341-45 (1986); Valeri et al., Am. J. Vet. Res. 42(9)1590-94 (1981). Solutions containing up to 1% glycerol are routinely transfused, and glycerol solutions are commercially available (e.g., Glyerolite 57 Solution, Fenwal Laboratories, Deerfield, Ill.). Adsorbent beads like Amberlite® XAD-16 may be stabilized in ethanol and glycerol.

Low molecular weight polyethylene glycols, commonly used as pharmaceutical bases, may also be used as stabilizing agents. PEGs are liquid and solid polymers of the general chemical formula $H(OCH_2CH_2)_nOH$, where n is greater than or equal to 4. PEG formulations are usually followed by a number that corresponds to its average molecular weight; for example, PEG-200 has a molecular weight of 200 and a molecular weight range of 190-210. PEGs are commercially available in a number of formulations (e.g., Carbowax, Poly-G, and Solbase).

Inert Matrices for Particle Immobilization

The adsorbent particles are immobilized by an inert matrix. The inert matrix can be made of a synthetic or natural polymer. For example, the inert matrix can be a synthetic or natural polymer fiber, for example, a fiber network. The inert matrix can be sintered polymers. The inert matrix, as with the other components of the device, preferably is biocompatible and does not substantially adversely affect the biological activity of a material upon contact.

Most preferably, the synthetic fibers are polyester fibers (Air Quality Filtration (AQF), a division of Hoechst Celanese (Charlotte, N.C.)). Other preferred examples of synthetic fibers are polyethylene or polyamide fibers. Other exemplary synthetic fibers include polyolefin, polyvinyl alcohol and polysulfone fibers.

In a preferred embodiment, the synthetic polymer fiber includes a first polymer core with a high melting point surrounded by a sheath with a lower melting temperature. The polymer core can be a polyester(polyethylene terephthalate). The sheath can be a nylon, or a modified polyester. Fibers are commercially available from Unitika (Osaka, Japan) and Hoechst Trevira GmbH & Co. (Augsberg, Germany).

Exemplary natural polymer fibers include cellulose fibers derived from a variety of sources, such as jute, kozu, kraft and manila hemp. Networks of synthetic or natural polymer fibers have been used to make filters as described in U.S. Pat. Nos. 4,559,145 and 5,639,376, which are herein incorporated by reference.

Synthetic polymers suitable for the construction of sintered particles are high density polyethylene, ultra high molecular weight polyethylene, polypropylene, polyvinyl fluoride, polytetrafluoroethylene, nylon 6. More preferably the sintered particles are polyolefins, such as polyethylene.

Polymeric fibers such as those described above may be adsorbent resins without the attachment of adsorbent particles. Such fibers may be formed into a fiber network or may be immobilized on a fiber network of a less adsorbent fiber. Such fibers are contemplated by the present invention; such fibers preferably contain a large, porous, adsorptive surface area or other adsorptive means to facilitate reduction in the concentration of low molecular weight compounds.

Immobilization of Particles

In one embodiment, the adsorbent particles are immobilized by an inert matrix to produce an adsorption medium for reducing the concentration of small organic compounds in a material. The inert matrix can be a three dimensional network including a synthetic or natural polymer fiber network with adsorbent particles immobilized therein.

Preferably, the adsorption medium comprises small porous adsorbent particles with highly porous structures and very high internal surface areas, as described above, immobilized by the inert matrix. Preferably, when a biological material is brought into contact with the adsorption medium, the adsorption medium does not substantially adversely affect the biological activity or other properties of the material.

Figure 2:
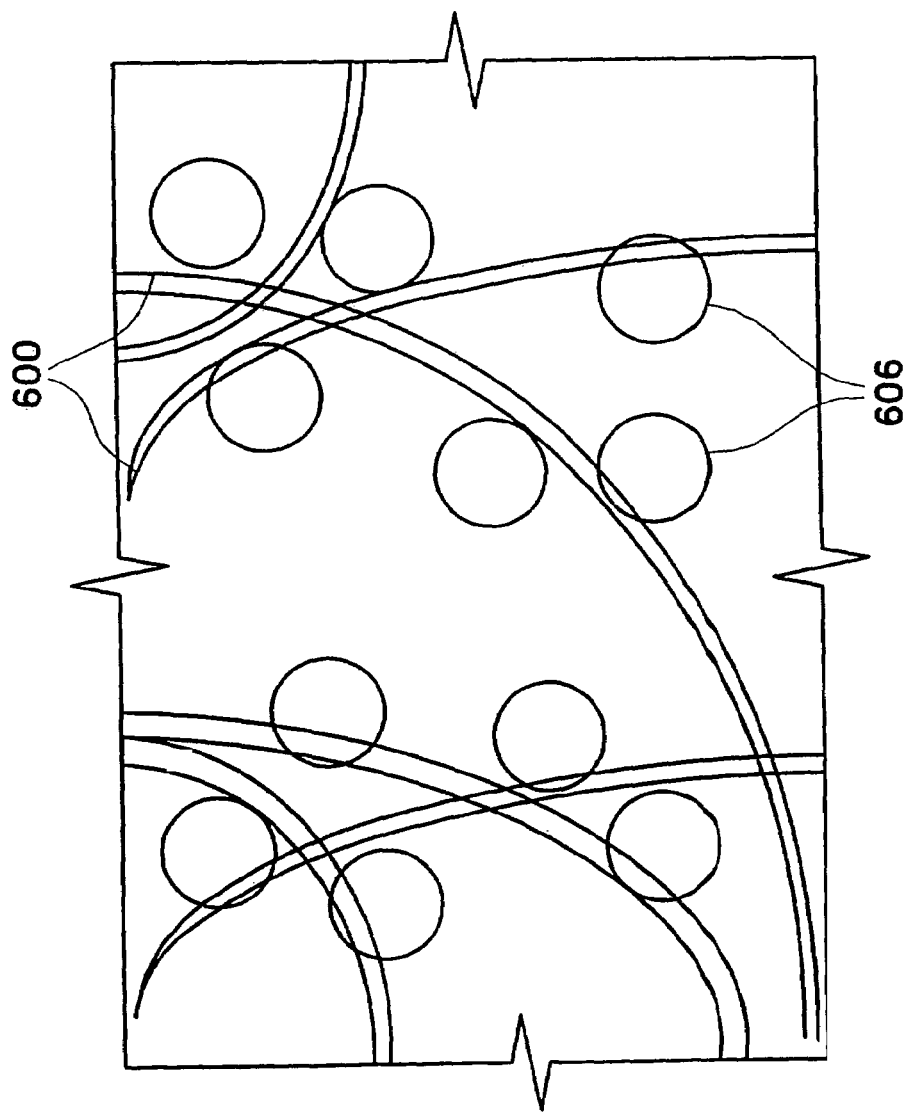
FIG. 2 schematically represents a portion of one embodiment of the immobilized adsorbent media of the present invention.
Figure 3:
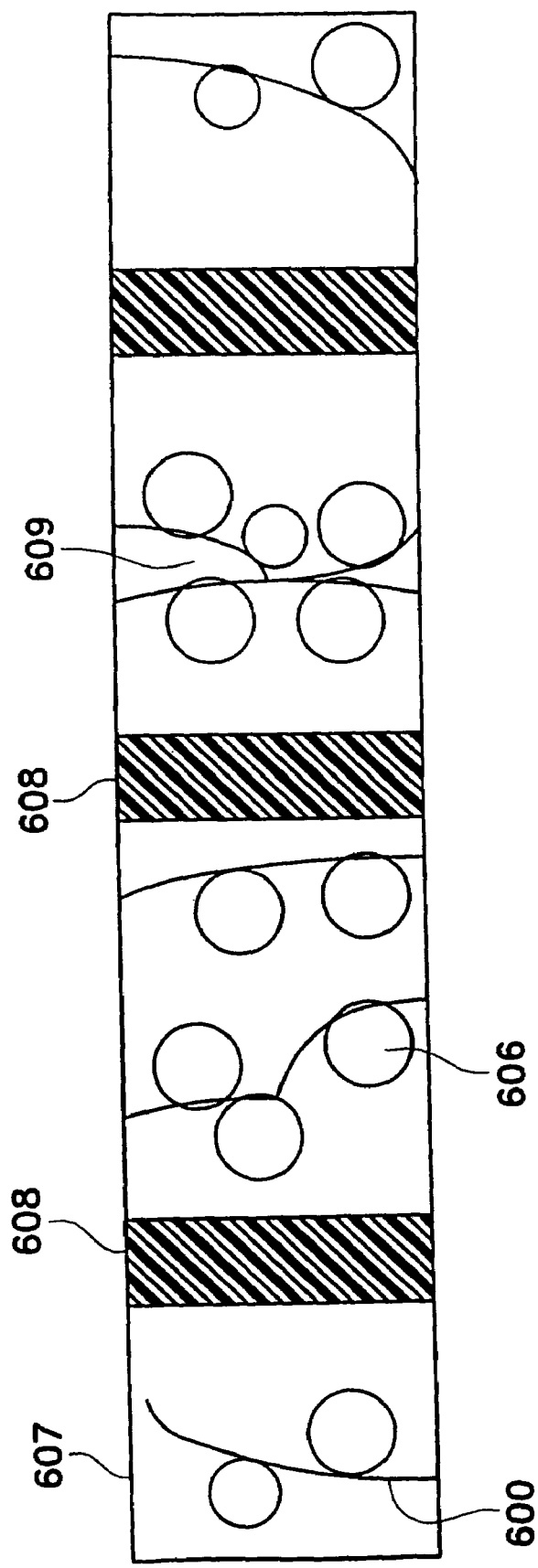
FIG. 3 diagrammatically represents a cross-sectional view of one embodiment of immobilized adsorbent media in which the adsorbent beads are secured to fibers that make up the fiberized resin.
Figure 4:
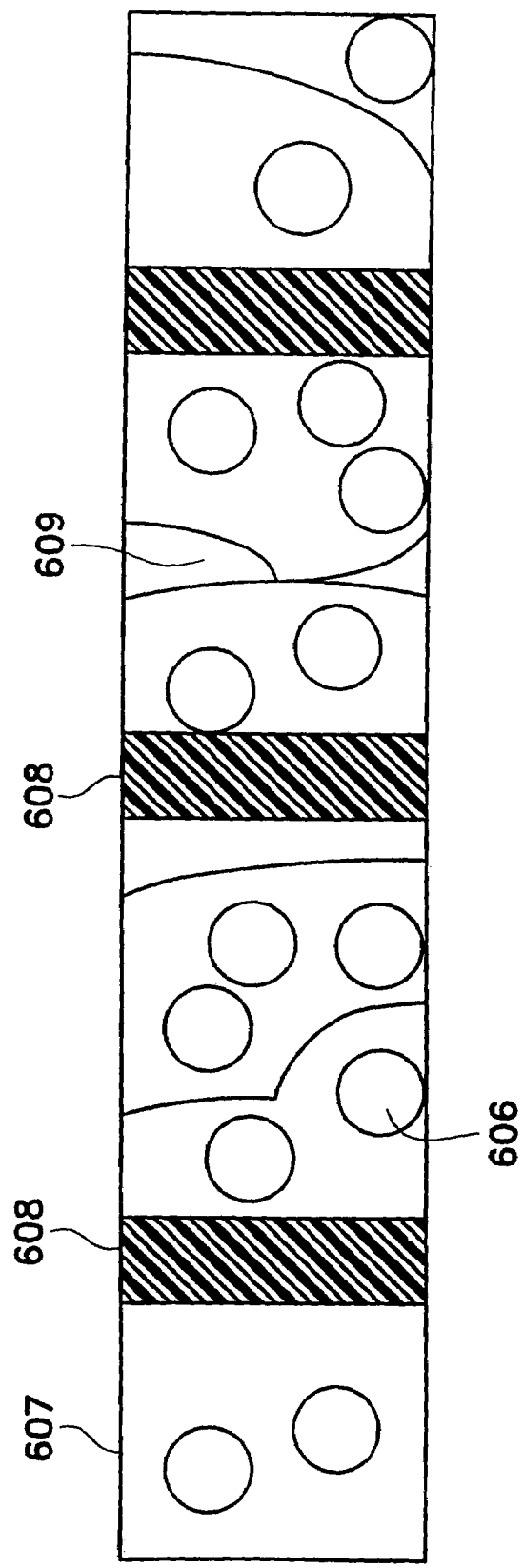
FIG. 4 diagrammatically represents a cross-sectional view of one embodiment of immobilized adsorbent media in which the adsorbent beads are immobilized within the fibers of the immobilized adsorbent media and the heat seals that encompass samples of fiberized resin.

Technology for immobilization of adsorbent beads on a fiber network to construct air filters has been described in U.S. Pat. Nos. 5,486,410 and 5,605,746, incorporated by reference herein. As depicted in FIG. 1, the polymer fibers 600 of the fiber network consist of a polymer core 602 (e.g., polyethylene terephthalates (PET)) with a high melting point surrounded by a polymer sheath 604 (e.g., nylon) with a relatively low melting temperature. See U.S. Pat. No.5,190,657 to Heagle et al., hereby incorporated by reference. The fiberized resin is prepared by first evenly distributing the adsorbent beads in the fiber network. Next, the network is rapidly heated (e.g., 180° C.×1 min.) causing the polymer sheath of the fibers 600 to melt and bond to the adsorbent beads 606 and other fibers, forming a cross-linked fiber network, represented in FIG. 2. As depicted in FIG. 3 and FIG. 4 (not to scale), generally speaking, the fiber networks contain three layers; two outer layers 607 that are densely packed with fibers 600 and a less dense inner layer 609 that contains the adsorbent beads 606 and fewer fibers 600. In a preferred embodiment, the edges of the fiberized resin may be sealed with polyurethane or other polymers. Alternatively, as depicted in FIG. 3 and FIG. 4, heat seals 608 may be made in the resulting fiberized resin at predetermined intervals; for example, heat seals can be made in the fiberized resin in a pattern of squares. Thereafter, the fiberized resin can be cut through the heat seals to form samples of resin containing a desired mass (e.g., preferably less than 5.0 g and more preferably less than 3.0 g) of adsorbent beads and of a size suitable for placement within a blood product container. The heat seals serve to prevent the cut fiberized resin from fraying and help to immobilize the adsorbent beads. However, the use of such heat seals is not required in order to practice the present invention. In an alternative embodiment, depicted in FIG. 4, the adsorbent beads 606 are not secured to the fibers themselves, but rather are immobilized between the denser outer layers 607 of fibers and with the heat seals 608; this embodiment may also result in samples of fiberized media containing a defined amount of adsorbent after being cut through the heat seals.

The present invention also contemplates the use of an adhesive (e.g., a bonding agent) to secure the adsorbent resin to the fibers. Moreover, while it is preferable that the adsorbent beads be chemically attached to the fiber network, the beads may also be physically trapped within the fiber network; this might be accomplished, for example, by surrounding the beads with enough fibers so as to hold the beads in position.

Other ways that the adsorbent particles may be immobilized in a fiber network are also contemplated. The particles can be immobilized using a dry-laid process, as described in U.S. Pat. Nos. 5,605,746 and 5,486,410 (AQF patents), which are herein incorporated by reference. The particles can be immobilized using a wet-laid process, as described in U.S. Pat. Nos. 4,559,145 and 4,309,247, which are herein incorporated by reference. The particles can be immobilized using a melt-blown process, as described in U.S. Pat. No. 5,616,254, which is herein incorporated by reference. Where a wet-laid process is used to construct a matrix from natural polymer fibers, the inert matrix preferably includes a binding agent to bond the adsorbent particles to the fibers. Nonlimiting examples of binding agents include melamine, polyamines and polyamides. The matrix typically contains 1% or less of such binding agents.

Where the inert matrix is constructed from particles of synthetic polymers which are sintered with adsorbent particles, it is important that the adsorbent particle have a higher melting temperature than the matrix.

In a preferred embodiment, the adsorbent particles are immobilized in a fiber matrix that is formed by thermal bonding of a biocomponent fiber network. An alternative embodiment involves immobilizing adsorbent particles in non-biocomponent fibers and using a wet strength resin system, adhesives or additional fusible fibers to form bonds between the fibers and adsorbent particles. Nonlimiting examples of useful fibers include polyester, nylon and polyolefin. (Suppliers of fibers for the nonwovens industry have been listed in "A Guide to Fibers for Nonwovens," *Nonwovens Industry*, June 1998, 66-87.) Examples of wet strength resin systems include melamine/formaldehyde, epichlorohydrin-based resins, polyamines and polyamides. The use of heat fusible fibers for immobilizing particles in fiber matrices has been disclosed. See, e.g., U.S. Pat. No. 4,160,059.

Preferably, the resulting adsorption medium comprises known amounts of adsorbent per area. The adsorbent per area is from about 100 $g/m^2$ to about 500 $g/m^2$, preferably from about 250 $g/m^2$ to about 350 $g/m^2$. Thus, the appropriate amount of adsorbent contemplated for a specific purpose can be measured simply by cutting a predetermined area of the fiberized resin (i.e., there is no weighing of the fiberized resin).

The adsorption medium preferably is biocompatible (i.e., not producing a toxic, injurious, or immunologic response); has a minimal impact on the properties of the material such as blood product (e.g., platelets and clotting factors); and is not associated with toxic extractables. The immobilized adsorbent particles of the adsorption medium preferably have high mechanical stability (i.e., no fine particle generation). The adsorption medium for a batch device contains about 25-85% adsorbent by weight, preferably about 50-80% adsorbent at a loading of about 100-500 $g/m^2$, more preferably about 50-80% adsorbent at a loading of about 250-350 $g/m^2$.

Coating the Adsorbent Particles

The surface hemocompatibility of the particles, matrices or adsorption medium can be improved by coating their surfaces with a hydrophilic polymer. Exemplary hydrophilic polymers include poly(2-hydroxyethyl methacrylate) (pHEMA), which may be obtained from, e.g., Scientific Polymer Products, Inc. (Ontario, N.Y.) and cellulose-based polymers, e.g., ethyl cellulose, which may be obtained from Dow Chemical (Midland, Mich.). See, e.g., Andrade et al., *Trans. Amer. Soc. Artif. Int. Organs* XVII:222-28 (1971). Other examples of coatings include polyethylene glycol and polyethylene oxide, also available from Scientific Polymer Products, Inc.. The polymer coating can increase hemocompatibility and reduce the risk of small particle generation due to mechanical breakdown.

The adsorbent surface may also be modified with immobilized heparin. In addition, strong anion exchange polystyrene divinylbenzene adsorbents may be modified via heparin adsorption. Heparin, a polyanion, will adsorb very strongly to the surfaces of adsorbents which have strong anion exchange characteristics. A variety of quaternary amine-modified polystyrene divinyl benzene adsorbents are commercially available.

The coating can be applied in a number of different methods, including radio frequency glow discharge polymerization, as described in U.S. Pat. No. 5,455,040, which is hereby incorporated by reference and the Wurster coating process (performed by International Processing Corp. (Winchester, Ky.).

In one embodiment, the Wurster coating process can be applied by suspending the adsorbent particles (generally via air pressure) in a chamber such that the hydrophilic polymer, such as pHEMA, can be sprayed evenly onto all surfaces of the adsorbent particle. As illustrated in Example 3, Dowex® XUS-43493 sprayed evenly with pHEMA demonstrated an increase in platelet yield as well as a dramatic effect on platelet shape change with increasing amounts of coating. It was found that the Wurster coating process selectively coated the outside surface of the adsorbent surface, leaving the inside porous surface nearly unaffected.

In a preferred embodiment, the coating can be applied by soaking the immobilized adsorption medium in the hydrophilic polymer (see Example 3). This process is simpler and less expensive than spraying the adsorbent particles with the hydrophilic polymer.

The process is not limited to a process that applies the coating of the adsorption medium at any particular time. For example, in one embodiment, the pHEMA coating is applied after production of the adsorption medium, but prior to heat sealing the adsorption medium. In another embodiment, the adsorption medium is first heat sealed, and then the pHEMA coating is applied. In addition to coating the adsorption medium, the rinsing process associated with pHEMA application serves to remove loose particles and fibers.

As the amount of coating is increased, it becomes more difficult for some small organic compounds to cross the coating to reach the particle surface, resulting in a decrease in adsorption kinetics. Thus, as the amount of coating is increased, an increased mass of adsorbent must generally be used to achieve the same removal kinetics as coated adsorbent. In one embodiment, the optimum level of pHEMA coating is the minimum coating at which a protective effect on platelet yield and in vitro platelet function is observed (0.1-0.5%).

The coatings may be sensitive to sterilization. For example, gamma sterilization may result in cross-linking and/or scission of the coating. Therefore, the type (E-beam vs. gamma irradiation) and dose of sterilization may influence the properties of the coated adsorbent. Generally, E-beam sterilization is preferred.

Devices

Figure 16:
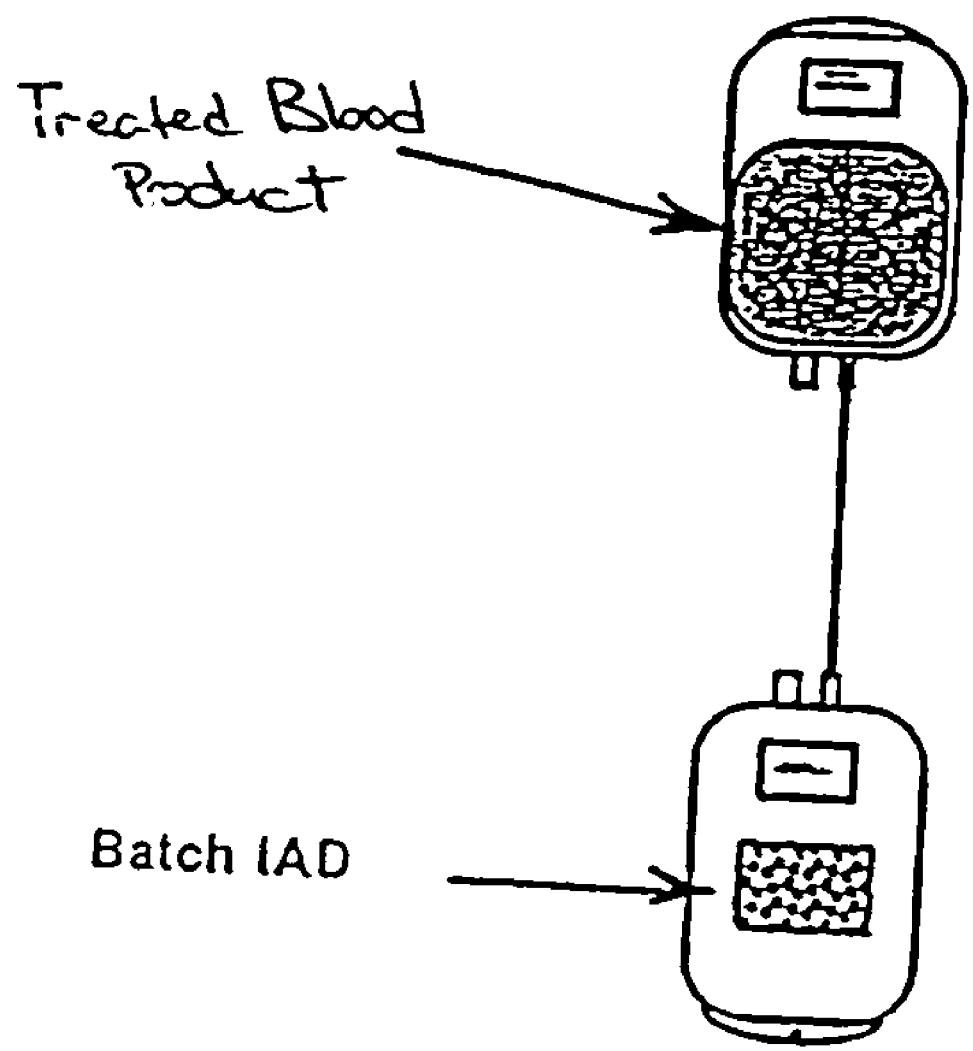
FIG. 16 is an illustration of a batch configuration for the immobilized adsorption device (IAD).

Devices are provided for reduction of compounds from biological compositions containing cells. The device is a batch device. An example of a batch device is shown in FIG. 16. Batch devices are known in the literature and are described, for example, in PCT publication WO 96/40857, incorporated by reference herein.

Batch devices of the invention may comprise a container, such as a blood bag, including the adsorbent medium containing immobilized particles. In one embodiment a blood product is added to a blood bag containing the adsorbent medium and the bag is agitated for a specified period of time.

For example, in one embodiment, an adsorption medium, e.g., immobilized Dowex® XUS-43493, is placed inside a blood product container (e.g., a PL 146 Plastic container (BaxterHealthcare Corp. (Deerfield, Ill.)) kept on either a platelet shaker (Helmer Laboratories (Novesvill, Ind.)) or rotator (Helmer Laboratories (Novesvill, Ind.)) for about 24 hours at room temperature and stored under various temperature conditions. The size of the blood product container can be from about 600 to about 1200 mL. The storage temperature can be from about 4° C. to about 22° C.

Methods can be used to reduce the presence of adsorbent particles that may come loose from the adsorbent medium.

The present invention contemplates a batch device including the immobilized adsorbent medium retained in a container such as a mesh bag/pouch. The mesh/pouch can be constructed of a woven, non-woven or membranous enclosure. In one embodiment, the woven mesh pouch can be constructed of medical-grade polyester or nylon. The preferred embodiment is polyester. Commercially-available membranes include, but are not limited to, Supor® 200, 800, 1200 hydrophilic polyethylene sulfonate (PES) membranes (Gelman Sciences (Ann Arbor, Mich.)); Durapore® hydrophilic modified polyvinylidene difluoride (PVDF) (Mantee America Corp. (San Diego, Calif.)) and hydrophilic modified polysulfone membranes with integrated hydrophobic vents, e.g. Gemini membranes, (Millipore (Marlborough, Mass.)); and membranes comprising polycarbonate with a polyvinylidene coating (Poretics (Livermore, Calif.)). The containers can be sterilized after addition of the adsorption medium.

Preferred Embodiment for Biological Compositions Containing Cells

The present invention provides devices for reducing the concentration of low molecular weight compounds in biological compositions containing cells. The devices comprise an adsorption medium, which is comprised of particles immobilized by an inert matrix.

Biological response modifiers like the anaphalatoxin C3a and the terminal membrane attack complex SC5b-9 have been shown to be produced by the processing, (e.g., leukofiltration, pheresis, recovery of shed blood, etc.) and storage of whole blood and its components. These biological response modifiers have been implicated in adverse events in surgery and transfusion.

In some embodiments, the device of the present invention reduces or controls the concentration of activated complement in biological compositions containing cells. The concentration of activated complement in the composition is reduced or controlled when it is treated with the device, as opposed to a composition that has not been treated with the device. In one embodiment, the adsorption device comprises fiberized Ambersorb IAD, for example, as produced by AQF. In this embodiment, exposure of biological compositions containing cells to the device results in a reduction in the C3a complement fragment and SC5b-9 terminal component complex over control. In one embodiment, exposure to the device for 5 days results in at least about a 10% reduction of C3a complement fragment over control. In another embodiment, exposure to the device for 5 days results in at least about a 30% reduction of C3a complement fragment over control. In another embodiment, exposure to the device for 5 days results in at least about a 50% reduction of C3a complement fragment over control.

In one embodiment, the invention provides a device for reducing the concentration of compounds in a biological composition comprising platelets. The biological activity of the platelets is substantially maintained after treatment with the device. The adsorption medium of this embodiment comprises adsorbent particles immobilized by an inert matrix. Preferred particles are highly porous and have a surface area greater than about 750 $m^2/g$.

Particularly preferred particles for this embodiment are polyaromatic adsorbents comprising a hypercrosslinked polystyrene network, such as Dowex® XUS-43493 or Purolite MN-200. The preferred inert matrix includes a synthetic or natural polymer fiber. In a preferred embodiment the inert matrix includes a synthetic polymer fiber which includes a first polymer core with a high melting point surrounded by a sheath with a lower melting temperature. The polymer core can be a polyethylene terphthalate core. The sheath can be a nylon sheath or a modified polyester sheath. Staple fibers are commercially available from Unitika (Osaka, Japan) and Hoechst Trevira.

Exemplary compounds that are reduced or controlled by the devices, materials and methods of this embodiment are psoralens, psoralen derivatives, isopsoralens, psoralen photoproducts, acridines, acridine derivatives, methylene blue, plastic extractables, biological response modifiers, quenchers and polyamine derivatives.

Biological compositions comprising platelets are typically used within 3 days of donation but may be stored for up to 7 days at room temperature, therefore, it would be advantageous to allow the platelet compositions to remain in contact with the adsorption medium for the entire storage period. Preferably, the procedure would result in an acceptable platelet yield (e.g., less than 10% loss). One method contemplated by the present invention allows extended storage by improving the hemocompatibility of the adsorbent surface.

The use of an adsorption medium comprising adsorbent particles immobilized by an inert matrix permits the concentration of low molecular weight compounds to be reduced without a substantial loss in platelet count. The phrase "without a substantial loss" refers to a platelet preparation that is suitable for its intended purpose, for example, is suitable for infusion into humans, and may refer to, for example, a loss of platelet count or function of less than about 10%, preferably less than about 5% over a period of time, more preferably at least 5 days. Furthermore, the time that the platelets may be contacted with the adsorption medium without substantial loss in platelet count is greater than the amount of time that the platelets can be contacted with the adsorbent particles alone. The immobilization of the particles unexpectedly permits both a longer contact time and a reduction in loss of platelet count. The platelets typically cannot be contacted with non-immobilized adsorbent particles for more than about 20 hours without a significant loss of platelet count e.g. about 20% loss. In contrast, platelets may be contacted with the adsorption medium comprising adsorbent particles immobilized by an inert matrix for more than 20 hours, e.g. about 1 to 7 days without a substantial loss in platelet count.

Additionally in vitro platelet function (e.g., shape change, GMP-140, pH) is improved for platelets stored in the presence of the adsorption medium in comparison to the storage of the platelets without the adsorption medium over time. Platelets stored in the presence of the adsorption medium can have a pH from greater than about 6 to less than about 7.5.

In another embodiment, the invention provides a device for reducing the concentration of low molecular weight compounds (e.g., small organic compounds) in a biological composition comprising red blood cells while substantially maintaining the biological activity of the red blood cells. Typically, the compounds removed by the device have a molecular weight ranging from about 100 g/mol to about 30,000 g/mol. The adsorption medium comprises adsorbent particles immobilized by an inert matrix. Preferred particles for this embodiment are highly porous and have a surface area greater than about 750 $m^2/g$.

Preferably, a device used for red blood cell compositions is a device that substantially maintains the biological activity of the red blood cells after reduction of the concentration of low molecular weight compounds. In one embodiment, the red blood cell device does not substantially adversely affect the biological activity of a fluid upon contact. The device embodiment comprises an adsorption medium containing particles immobilized by an inert matrix and optionally a particle retention device.

In one embodiment the particles used in devices for red blood cell compositions are activated charcoal. Preferably the activated carbons are derived from synthetic sources. Non-limiting examples of activated carbons include Picactif Medicinal, which is available from Pica U.S.A. (Columbus, Ohio); Norit ROX 0.8, which is available from Norit Americas Inc. (Atlanta, Ga.); and G-277, which is available from Pica U.S.A. (Columbus, Ohio).

In one embodiment, the adsorbent is preferably an activated carbon derived from a synthetic source, such as Ambersorb 572. The Ambersorbs are synthetic activated carbonaceous (i.e. rich in carbon) adsorbents that are manufactured by Rohm & Haas (Philadelphia, Pa.). Ambersorbs are generally large spherical (300-900 µm) particles that are more durable than typical activated carbons. The Ambersorbs are synthetically manufactured by treating highly sulfonated porous polystyrene beads with a proprietary high temperature activation process. These adsorbents do not require pre-swelling to achieve optimal adsorption activity.

In another embodiment, the particles used in devices for use with compositions containing red blood cells ("red blood cell devices") can be hydrophobic resins. Nonlimiting examples of hydrophobic resins include the following polyaromatic adsorbents: Amberlite® adsorbents (e.g., Amberlite® XAD-2, XAD-4, and XAD-16), available from Rohm and Haas (Philadelphia, Pa.); Amberchrom® adsorbents available from Toso Haas (Toso Haas, Montgomeryville, Pa.); and Diaion®//Sepabeads® Adsorbents (e.g., Diaion® HP20), available from Mitsubishi Chemical America, Inc. (White Plains, N.Y.). In a particularly preferred embodiment the particles are Hypersol-Macronete Sorbent Resins (e.g., Hypersol-Macronet® Sorbent Resins MN-200, MN-150 and MN-400) available from Purolite (Bala Cynwyd, Pa.) or Dowex® Adsorbents (e.g., Dowex® XUS-43493, and XUS-40285), available from Dow Chemical Company (Midland, Mich.).

The preferred inert matrix of a red blood cell device includes a synthetic or natural polymer fiber. In a preferred embodiment the inert matrix includes a synthetic polymer fiber which includes a first polymer core with a high melting point surrounded by a sheath with a lower melting temperature. The polymer core can be a polyethylene terephthalate or polyester core. The sheath can be a nylon sheath or a modified polyester sheath. Fibers are commercially available from Unitika (Osaka, Japan) and Hoechst Trevira (Augsberg, Germany).

In some embodiments, the adsorption medium of a red blood cell device is in an enclosure. In one embodiment, the device comprises an adsorption medium, and a housing. In another embodiment, the device comprising an adsorption medium and a housing may also include a particle retention medium. In one embodiment, the housing comprises a blood bag of a volume between about 600 ml and about 1 L. In another embodiment, the housing comprises a blood bag of a volume between about 800 ml and about 1 L. The particle retention medium may comprise a polyester woven, polyester non-woven, or synthetic membranous enclosure.

It is preferable that the device contact the red blood composition at about 4° C. or about 22° C. (room temperature), in the presence of agitation, over a time period of 1 to 35 days. In one embodiment, the red blood composition is contacted with the device at about 22° C. for no more than about 36 hours. In another embodiment, the red blood cell composition is contacted with the device at about 22° C. for no more than about 24 hours. In another embodiment, the red blood composition is contacted with the device at about 22° C. for no more than about 12 hours. In another embodiment, the red blood composition is contacted with the device at about 22° C. for no more than 6 hours.

In some embodiments, the temperature is changed after the red blood composition is brought into contact with the device. In one embodiment, the device is contacted with the red blood composition at about 22° C. for a time ranging from about 0.5 to about 24 hours and then stored at about 4° C. for up to about 5 weeks. In another embodiment, the device is contacted with the red blood composition at about 22° C. for a time ranging from about 0.5 to about 12 hours and then stored at about 4° C. for up to about 5 weeks. In another embodiment, the device is contacted with the red blood composition at about 22° C. for a time ranging from about 0.5 to about 6 hours and then stored at about 4° C. for up to about 5 weeks.

The use of an adsorption medium comprising adsorbent particles immobilized by an inert matrix permits the treatment of the red blood cell composition without a substantial loss in red blood cell function. The phrase "without a substantial loss" refers to a product that would be allowable for transfusion, or its intended purpose, and in some instances may refer to less than about 1% hemolysis; preferably less than about 0.8% hemolysis, greater than about 80% recovery of red blood cells; preferably greater than 90% recovery of red blood cells, less than about 10% difference from no-device control red blood cells in change in ATP concentration, and less than about 15% difference from no-device control red blood cells in change in extracellular potassium concentration. At 35 days, the change in hemolysis is at least 10% lower for the LAD compared to the non-immobilized particles, preferably, 20% lower and more preferably 50%. Most preferably, the change is hemolysis is at least 90% lower for the IAD compared to the non-immobilized particles.

Red blood cell function can be assayed using standard kits. In particular, hemolysis may be determined by measuring the absorbance at 540 nm of a red blood cell supernatant sample in Drabkin's reagent ((Sigma Chemical Company), St. Louis, Mo.). Potassium leakage can be assayed using a Na+/K+ analyzer. (Ciba-Corning Diagnostics, Medfield, Mass.). Quantitative enzymatic determination of ATP in total Red Blood Cell samples is possible using a standard kit (Sigma Diagnostics, St. Louis, Mo.) and measuring absorbance at 340 nm compared to a water background.

Where the biological composition to be treated is a red blood cell containing composition, the device can reduce the concentration of low molecular weight compounds in a red blood cell sample. Preferably the device can reduce the concentration of both acridine derivatives and thiols in a red blood cell sample. More preferably, the device can reduce the concentration of both 5-[(β-carbethyoxyethyl)amino]-acridine and glutathione in a red blood cell sample.

Standard HPLC assays can be used to determine concentrations of 5-[(β-carboxyethyl)amino]acridine and glutathione in red blood cells contacted with the device. Assay mobile phases are 10 mM $H_3PO_4$ in HPLC water and 10 mM $H_3PO_4$ in acetonitrile. Zorbax SB-CN and YMC ODSAM-303 columns are available from MacMod Analytical, Inc. (Chadds Ford, Pa.) and YMC, Inc. (Wilmingtion, N.C.).

Where a device is brought into contact with a biological composition containing cells in the presence of agitation, the agitation can be constant or intermittent. The agitation is provided through any suitable means which maintains the functionality of the cells, including mechanical agitators of the following types: reciprocating, orbital, 3-D rotator and rotator type agitators. In one embodiment, the agitation is provided by an orbital agitator and is constant. In another embodiment, the agitation is provided by an orbital agitator and is intermittent. In another embodiment, the agitation is provided by a reciprocating agitator.

Applications

The present invention contemplates reducing the concentration of low molecular weight compounds from biological compositions containing cells. Such compounds include, for example, pathogen-inactivating agents such as photoactivation products, aminoacridines, organic dyes and phenothiazines. Exemplary pathogen inactivating agents include furocoumarins, such as psoralens and acridines. Following treatment of a blood product with a pathogen inactivating compound as described for example in U.S. Pat. Nos. 5,459,030 and 5,559,250, incorporated by reference herein, the concentration of pathogen inactivating compounds in the blood product can be reduced by contacting the treated blood product with a device of the invention.

In one embodiment the present invention contemplates a method of inactivating pathogens in solution, wherein the method comprises: a) providing, in any order: i) a cyclic compound, ii) a solution suspected of being contaminated with said pathogens, and iii) fiberized resin; b) treating said solution with said cyclic compound so as to create a treated solution product wherein said pathogens are inactivated; and c) contacting said treated solution product with said fiberized resin, and further comprising a device for reducing the concentration of small organic compounds in a blood product while substantially maintaining a desired biological activity of the blood product, the device comprising highly porous adsorbent particles, wherein the adsorbent particles are immobilized by an inert matrix.

In addition to the pathogen inactivating compound, reactive degradation products thereof can be reduced from the material such as a blood product, for example prior to transfusion.

The materials and devices disclosed herein can be used in apheresis methods. Whole blood can be separated into two or more specific components (e.g., red blood cells, plasma and platelets). The term "apheresis" refers broadly to procedures in which blood is removed from a donor and separated into various components, the component(s) of interest being collected and retained and the other components being returned to the donor. The donor receives replacement fluids during the reinfusion process to help compensate for the volume and pressure loss caused by component removal. Apherersis systems are described in PCT publication WO96/40857, hereby incorporated by reference.

Low Molecular Weight Compounds

A device of the present invention reduces the concentration of a low molecular weight compound in a composition containing cells. The term "low molecular weight compound" refers to an organic or biological molecule having a molecular weight ranging from about 100 g/mol to about 30,000 g/mol. Low molecular weight compounds include, without limitation, the following compounds: small organic compounds such as psoralens, acridines or dyes; quenchers, such as glutathione; plastic extractables, such as plasticizers; biological modifiers, such as activated complement, that possess a molecular weight between about 100 g/mol and about 30,000 g/mol; and, polyamine derivatives.

Small Organic Compounds

A diverse set of small organic compounds can be adsorbed by the device of the present invention. The molecules can be cyclic or acyclic. In one embodiment the compounds are preferably, cyclic compounds such as psoralens, acridines or dyes. In another embodiment the compounds are thiols.

Nonlimiting examples of cyclic compounds include actinomycins, anthracyclinones, mitomyacin, anthramycin, and organic dyes and photoreactive compounds such as benzodipyrones, fluorenes, fluorenones, furocoumarins, porphyrins, protoporphyrins, purpurins, phthalocyanines, hypericin, Monostral Fast Blue, Norphillin A, phenanthridines, phenazathionium salts, phenazines, phenothiazines, phenylazides, quinolines and thiaxanthenones. Preferably the compounds are furocoumarins or organic dyes. More preferably the compounds are furocoumarins.

Nonlimiting examples of furocoumarins, include psoralens and psoralen derivatives. Specifically contemplated are 4'-aminomethyl-4,5',8-trimethylpsoralen, 8-methoxypsoralen, halogenated psoralens, isopsoralens and psoralens linked to quaternary amines, sugars, or other nucleic acid binding groups. Also contemplated are the following psoralens: 5'-bromomethyl-4,4',8-trimethylpsoralen, 4'-bromomethyl-4,5',8-trimethylpsoralen, 4'-(4-amino-2-aza)butyl-4,5', 8-trimethylpsoralen, 4'-(4-amino-2-oxa)butyl-4,5',8-trimethylpsoralen, 4'-(2-aminoethyl)-4,5',8-trimethylpsoralen, 4'-(5-amino-2-oxa)pentyl-4,5',8-trimethylpsoralen, 4'-(5-amino-2-aza)pentyl-4,5',8-trimethylpsoralen, 4'-(6-amino-2-aza)hexyl-4,5',8-trimethylpsoralen, 4'-(7-amino-2,5-oxa)heptyl-4,5',8-trimethylpsoralen, 4'-(12-amino-8-aza-2,5-dioxa)dodecyl-4,5',8-trimethylpsoralen, 4'-(13-amino-2-aza-6,11-dioxa)tridecyl-4,5',8-trimethylpsoralen, 4'-(7-amino-2-aza)heptyl-4,5',8-trimethylpsoralen, 4'-(7-amino-2-aza-5-oxa)heptyl-4,5',8-trimethylpsoralen, 4'-(9-amino-2,6-diaza)nonyl-4,5',8-trimethylpsoralen, 4'-(8-amino-5-aza-2-oxa)octyl-4,5',8-trimethylpsoralen, 4'-(9-amino-5-aza-2-oxa)nonyl-4,5',8-trimethylpsoralen, 4'-(14-amino-2,6,11-triaza)tetradecyl-4,5',8-trimethylpsoralen, 5'-(4-amino-2-aza)butyl-4,4',8-trimethylpsoralen, 5'-(6-amino-2-aza)hexyl-4,4',8-trimethylpsoralen and 5'-(4-amino-2-oxa)butyl-4,4',8-trimethylpsoralen. Preferably, the psoralen is 4'-(4-amino-2-oxa)butyl-4,5',8-trimethylpsoralen.

Acridines

Nonlimiting examples of acridines include acridine orange, acriflavine, quinacrine, N1,N1-bis(2-hydroxyethyl)-N4-(6-chloro-2-methoxy-9-acridinyl)-1,4-pentanediamine, 9-(3-hydroxypropyl)aminoacridine, N-(9-acridinyl)glycine, S-(9-acridinyl)-glutathione. In a preferred embodiment the acridine is N-(9-acridinyl)-β-alanine, alternatively, named 5-[(β-carboxyethyl)amino]acridine.

Dyes

Nonlimiting examples of dyes include phenothiazines such as methylene blue, neutral red, toluidine blue, crystal violet and azure A, phenothiazones such as methylene violet Bernthsen, phthalocyanines such as aluminum 1,8,15,22-tetraphenoxy-29H,31H-phthalocyanine chloride and silica analogues, and hypericin. Preferably, the dye is methylene blue or toluidine blue. More preferably, the dye is methylene blue.

The term "thiazine dyes" includes dyes that contain a sulfur atom in one or more rings. The most common thiazine dye is methylene blue [3,7-Bis(dimethylamino)-phenothiazin-5-ium chloride). Other thiazine dyes include, but are not limited to, azure A, azure C and thionine, as described e.g. in U.S. Pat. No. 5,571,666 to Schinazi.

The term "xanthene dyes" refers to dyes that are derivatives of the compound xanthene. The xanthene dyes may be placed into one of three major categories: i) fluorenes or amino xanthenes, ii) the rhodols or aminohydroxyxanthenes, and iii) the fluorones or hydroxyxantheses. Examples of xanthene dyes contemplated for use with the present invention include rose bengal and eosin Y; these dyes may be commercially obtained from a number of sources (e.g., Sigma Chemical Co., St. Louis, Mich.), and as described e.g. in U.S. Pat. No. 5,571,666 to Schinazi, hereby incorporated by reference.

Quenchers

The concentration of a variety of compounds may be reduced. Other exemplary compounds include quenching compounds. Methods for quenching undesired side reactions of pathogen inactivating compounds that include a functional group which is, or which is capable of forming, an electrophilic group, are described in the co-owned U.S. Patent Application, "Methods for Quenching Pathogen Inactivators in Biological Systems", 60/070,597, filed Jan. 6, 1998, the disclosure of which is incorporated herein. In this method, a material, such as a blood product, is treated with the pathogen inactivating compound and a quencher, wherein the quencher comprises a nucleophilic functional group that is capable of covalently reacting with the electrophilic group. In one embodiment, the pathogen inactivating compound includes a nucleic acid binding ligand and a functional group, such as a mustard group, which is capable of reacting in situ to form the electrophilic group. Examples of quenchers include, but are not limited to, compounds including nucleophilic groups. Exemplary nucleophilic groups include thiol, thioacid, dithoic acid, thiocarbamate, dithiocarbamate, amine, phosphate, and thiophosphate groups. The quencher may be, or contain, a nitrogen heterocycle such as pyridine. The quencher can be a phosphate containing compound such as glucose-6-phosphate. The quencher also can be a thiol containing compound, including, but not limited to, glutathione, cysteine, N-acetylcysteine, mercaptoethanol, dimercaprol, mercaptan, mercaptoethanesulfonic acid and salts thereof, e.g., MESNA, homocysteine, aminoethane thiol, dimethylaminoethane thiol, dithiothreitol, and other thiol containing compounds. Exemplary aromatic thiol compounds include 2-mercaptobenzimidazolesulfonic acid, 2-mercapto-nicotinic acid, napthalenethiol, quinoline thiol, 4-nitro-thiophenol, and thiophenol. Other quenchers include nitrobenzylpyridine and inorganic nucleophiles such as selenide salts or organoselenides, thiosulfate, sulfite, sulfide, thiophosphate, pyrophosphate, hydrosulfide, and dithionitrite. The quencher can be a peptide compound containing a nucleophilic group. For example, the quencher may be a cysteine containing compound, for example, a dipeptide, such as GlyCys, or a tripeptide, such as glutathione.

Compounds that may be removed by the device of the present invention may include thiols such as methyl thioglycolate, thiolactic acid, thiophenol, 2-mercaptopyridine, 3-mercapto-2-butanol, 2-mercaptobenzothiazole, thiosalicylic acid and thioctic acid.

Plastic Extractables

The concentration of a group of low molecular weight compounds that are extractables from plastic storage containers and tubing used to handle biological compositions may also be reduced in a biological composition using a device of the present invention. Examples of extractables include, but are not limited to, plasticizers, residual monomer, low molecular weight oligomers, antioxidants and lubricants. See, e.g., R. Carmen, *Transfusion Medicine Reviews* 7(1):1-10 (1993). The sterilization of plastic components by steam, gamma irradiation or electron beam can produce oxidative reactions and/or polymer scission, resulting in the formation of additional extractable species.

Plasticizers are commonly used to enhance properties of plastics such as processability and gas permeability. The most common plasticizer found in blood storage containers is di(2-ethylhexyl) phthalate (DEHP), which is used in PVC formulations. DEHP has been identified as a potential carcinogen. Alternative plasticizers have been developed, including, without limitation, the following compounds: tri (2-ethylhexyl) trimellitate (TEHTM), acetyl-tri-n-hexyl citrate (ATHC), butyryl-tri-n-hexyl-citrate (BTHC), and di-n-decyl phthalate.

A device of the present invention may be used to reduce or control the concentration of plastic extractables in a biological composition in a variety of settings. Such settings include, but are not limited to, the following: blood treatment; blood storage; and, extracorporeal applications such as hemodialysis and extracorporeal membrane oxygenation.

Biological Response Modifiers (BRMs)

The concentration of a group of low molecular weight compounds broadly referred to as biological response modifiers (BRMs) may also be reduced or controlled in a biological composition using a device of the present invention. BRMs are defined as "a wide spectrum of molecules that alter the immune response." *Illustrated Dictionary of Immunology*, J. M. Cruse and R. E. Lewis. General groups of BRMs include, without limitation, the following types of compounds: small molecules such as histamine and serotonin; lipids such as thromboxanes, prostaglandins, leukotrienes and arachidonic acid; small peptides such as bradykinin; larger polypeptides that contain further groups, including activated complement fragments (C3a, C5a); cytokines such as IL-1, IL-6 and IL-8; and chemokines such as RANTES and MIP.

The accumulation of BRMs in a blood product during storage can adversely affect the desired biological activity of a biological composition. Complement activation, for example, has been demonstrated to occur during storage of platelets under standard blood bank conditions. Complement activation has been associated with a loss of platelet function and viability termed "platelet storage lesion." See, e.g., V. D. Mietic and O. Popovic, *Transfusion* 33(2):150-154 (1993). The accumulation of BRMs in a stored blood products can also, for example, adversely affect a patient that receives the blood product: the accumulation of BRMs in platelet concentrates during storage has been associated with non-hemolytic febrile transfusion reactions in patients receiving platelets. See, e.g., N. M. Heddle, *Current Opinions in Hematology* 2(6):478-483 (1995).

Polyamine Derivatives

The concentration of a group of low molecular weight compounds known as polyamine derivatives may also, for example, be reduced in a biological composition using a device of the present invention. Polyamine derivatives are compounds that contain multiple nitrogen atoms in a carbon backbone.

Polyethylene Glycols

Other exemplary compounds include activated polyethylene glycols (aPEG), which may be used for the modification of the surface of cells or materials in order to provide immunomasking properties or pacification toward protein binding, respectively. The device may be used for the reduction of either the excess activated polyethylene glycol or the unreactive derivative of the PEG resulting from the reaction of the activated PEG with water or small nucleophiles such as phosphate, phosphate esters or thiols, such as glutathione. Other compounds that may be removed include impurities in the activated PEG preparation, which may affect the function of the blood products or make them unsuitable for transfusion (eg. toxic compounds). Finally, small molecules (leaving groups) such as N-Hydroxy succinimide which are released during the reaction of the aPEG with cell surface nucleophiles may also be reduced.

Examples of compounds that may be removed by the device of the present invention include linear or branched polyethylene glycols attached to activating moeities which may include cyanuryl chloride, succinimidyl esters, oxycarbonyl imidazole derivatives, nitrophenyl carbonate derivatives, glycidyl ether derivatives, and aldehydes.

It is to be understood that the invention is not to be limited to the exact details of operation or exact compounds, composition, methods, or procedures shown and described, as modifications and equivalents will be apparent to one skilled in the art. From the above, it should be clear that the methods and devices can be incorporated with apheresis systems and other devices and procedures currently used to process blood products for transfusion.

EXAMPLES

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); μL(microliters); cm (centimeters); mm (millimeters); μm (micrometers); nm (nanometers); min. (minutes); s and sec. (seconds); J (Joules, also watt second); ° C. (degrees Centigrade); TLC (Thin Layer Chromatography); HPLC (high pressure liquid chromatography); pHEMA and p(HEMA) (poly[2-hydroxyethyl methacrylate]); PC(s) (platelet concentrate(s)); PT (prothrombin time); aPTT (activated partial thromboplastin time); TT (thrombin time); HSR (hypotonic shock response); FDA (United States Food and Drug Administration); GMP (good manufacturing practices); DMF (Drug Masterfiles); SPE (Solid Phase Extraction); Aldrich (Milwaukee, Wis.); Asahi (Asahi Medical Co., Ltd., Tokyo, Japan); Baker (J.T. Baker, Inc., Phillipsburg, N.J.); Barnstead (Barnstead/Thermolyne Corp., Dubuque, Iowa); Becton Dickinson (Becton Dickinson Microbiology Systems; Cockeysville, Md.); Bio-Rad (Bio-Rad Laboratories, Hercules, Calif.); Cerus (Cerus Corporation; Concord, Calif.); Chrono-Log (Chrono-Log Corp.; Havertown, Pa.); Ciba-Corning (Ciba-Corning Diagnostics Corp.; Oberlin, Ohio); Consolidated Plastics (Consolidated Plastics Co., Twinsburg, Ohio); Dow (Dow Chemical Co.; Midland, Mich.); Eppendorf (Eppendorf North America Inc., Madison, Wis.); Gelman (Gelman Sciences, Ann Arbor, Mich.); Grace Davison (W.R. Grace & Co., Baltimore, Md.); Helmer (Helmer Labs, Noblesville, Ind.); Hoechst Celanese (Hoechst Celanese Corp., Charlotte, N.C.); International Processing Corp. (Winchester, Ky.); Millipore (Milford, Mass.); NIS (Nicolet, a Thermo Spectra Co., San Diego, Calif.); Poretics (Livermore, Calif.); Purolite (Bala Cynwyd, Pa.); Rohm and Haas (Chauny, France); Quidel (San Diego, Calif.); Saati (Stamford, Conn.); Scientific Polymer Products (Ontario, N.Y.); Sigma (Sigma Chemical Company, St. Louis, Mo.); Spectrum (Spectrum Chemical Mfg. Corp., Gardenia, Calif.); Sterigenics (Corona, Calif.); Tetko, Inc. (Depew, N.Y.); Toso-Haas (TosoHass, Montgomeryville, Pa.); Wallac (Wallac Inc., Gaithersburg, Md.); West Vaco (Luke, W.V.); YMC (YMC Inc., Wilmington, N.C.); DVB (divinyl benzene); LAL (Limulus Amoebocyte Lystate); USP (United States Pharmacopeia); EAA (ethyl-acetoacetate); EtOH (ethanol); HOAc (acetic acid); W (watts); mW (milliwatts); NMR (Nuclear Magnetic Resonance; spectra obtained at room temperature on a Varian Gemini 200 MHz Fourier Transform Spectrometer); ft$^3$/min (cubic feet per minute); m.p. (melting point); g/min and gpm (gallons per minute); UV (ultraviolet light); THF (tetrahydrofuran); DMEM (Dulbecco's Modified Eagles Medium); FBS (fetal bovine serum); LB (Luria Broth); EDTA (ethelene diamine tetracidic acid); Phorbol Myristate Acetate (PMA); phosphate buffered saline (PBS); AAMI (Association for the Advancement of Medical Instruments); ISO (International Standards Organization); EU (endotoxin units); LVI (large volume injectables); GC (gas chromatography); M (mega-); kGy (1000 Gray=0.1 MRad); MΩ (Mohm); PAS III (platelet additive solution III); dH$_2$O (distilled water); IAD (immobilization adsorption device); SCD (sterile connection [connect] device).

One of the examples below refers to HEPES buffer. This buffer contains 8.0 g of 137 mM NaCl, 0.2 g of 2.7 mM KCl, 0.203 g of 1 mM MgCl$_2$(6H$_2$O), 1.0 g of 5.6 mM glucose, 1.0 g of 1 mg/ml Bovine Serum Albumin (BSA) (available from Sigma, St. Louis, Mo.), and 4.8 g of 20 mM HEPES (available from Sigma, St. Louis, Mo.).

Example 1

Fiberized Resin with Amberlite® XAD-16

This example compares both the kinetics of removal of aminopsoralens from platelets and platelet function and morphology utilizing fiberized resin and devices containing non-immobilized adsorbent beads. More specifically, fiberized resin comprising immobilized Amberlite® XAD-16 was compared with devices containing free (i.e., not immobilized) Amberlite® XAD-16 HP and Dowex® XUS-43493.

Preparation of Fiberized Resin and Adsorbent Beads

Immobilized adsorbent media containing Amberlite® XAD-16 in a cleaned and hydrated state (Rohm and Haas) was obtained from AQF. The fibers of Hoechst Celanese's fiber network consisted of a polyethylene terephthalate core and a nylon sheath, the sheath having a lower melting temperature than the core. The fiberized resin was prepared by first evenly distributing the adsorbent beads in the fiber network. Next, the fiber network was rapidly heated causing the polymer sheath of the fibers to melt and bond to the adsorbent beads and other fibers, forming a cross-linked fiber network. The fiberized resin formed contained the Amberlite® XAD-16 at a loading of 130 g/m$^2$ (i.e., each square meter of fiber contained 130 g of adsorbent beads).

The fiberized resin was cut into squares (14 cm×14 cm), and the resulting sections contained approximately 2.5 g of dry Amberlite® XAD-16. The Amberlite® XAD-16 beads were then pre-wet by soaking the fiberized resin in 30% ethanol for approximately 10 minutes. The residual ethanol was then removed by rinsing twice in saline for 10 minutes. Alternative methods of wetting the Amberlite® XAD-16 and other adsorbents are also effective and are contemplated by the present invention. It should be noted that fiberized resin containing other types of beads (e.g., bridged or hyper-crosslinked resins like Dowex® XUS-43493) do not require a wetting step for effective psoralen removal.

Amberlite® XAD-16 HP (High Purity) beads were also obtained directly from Rohm and Haas in a cleaned and hydrated state. No pre-wetting was required for the loose (i.e., not immobilized) Amberlite® XAD-16 HP beads prior to incorporation into a mesh pouch; however, the mass of adsorbent was corrected to account for the water content of the beads (2.5 g dry=6.8 g with 62.8% moisture). The Dowex® XUS-43493 beads were obtained from Dow, and the dry beads did not require wetting nor did the mass of the beads require correction for water. Polyester mesh pouches (7 cm×7 cm square; 30 μm openings) were then filled with 2.5 g (dry weight) of either the loose Amberlite® XAD-16 HP or Dowex® XUS-43493 beads.

The fiberized resin and adsorbent-containing pouches were sterilized by autoclaving on "wet" cycle for 45 minutes at 121° C. Thereafter, the fiberized resin and the adsorbent-containing pouches were inserted into separate, sterile, 1-liter PL 2410 Plastic containers (Baxter). Following insertion, the PL 2410 Plastic containers were heat sealed in a laminar flow hood, using sterile scissors, hemostats, and an impulse sealer.

Contacting Fiberized Resin And Adsorbent Beads With Psoralen-Containing Platelet Concentrate (PC)

Pools of platelet concentrate were prepared by combining 2-3 units of single donor apheresis platelets in 35% autologous plasma/65% Platelet Additive Solution (i.e., synthetic media). To this solution was added the aminopsoralen 4'-(4-amino-2-oxa)butyl-4,5',8-trimethyl psoralen (S-59) in an amount to achieve a final concentration of 150 μM 4'-(4- amino-2-oxa)butyl-4,5',8-trimethyl psoralen. The resulting PC solution was divided into 300 mL units, and the units were then placed in PL 2410 Plastic containers (Baxter) and illuminated with 3 J/cm$^2$ of UVA. Following illumination, the treated PCs were transferred into the PL 2410 Plastic containers containing either fiberized resin with immobilized Amberlite® XAD-16, loose Amberlite® XAD-16 HP or loose Dowex® XUS-43493, or into an empty PL 2410 Plastic container as a control. The PL 2410 Plastic containers (Baxter) were then placed on a Helmer platelet incubator at 22° C. and agitated at approximately 70 cycles/minute.

Samples of each PC were removed at 1-hour intervals during the first 8 hours of storage for analysis by HPLC of residual 4'-(4-amino-2-oxa)butyl-4,5',8-trimethyl psoralen. Each sample of PC was diluted 5-fold with sample diluent (final concentration=35% methanol, 25 mM $KH_2PO_4$, pH=3.5) containing trimethylpsoralen (TMP) as the internal standard. Proteins and other macromolecules were precipitated by incubating the samples at 4° C. for 30 minutes. The samples were then centrifuged and the supernatant was filtered (0.2µ meter) and analyzed on a C-18 reversed phase column (YMC ODS-AM 4.6 mm×250 mm) by running a linear gradient from 65% solvent A (25 mM $KH_2PO_4$, pH=3.5), 35% B (methanol) to 80% B in 20 minutes.

Platelet yield during a 5-day storage period with the fiberized resin or one of the loose beads was monitored daily by counting platelets on a Baker System 9118 CP (Baker Instrument Co.; Allentown, Pa.). Blood gases and pH were evaluated using a Ciba-Corning 238 pH/Blood Gas Analyzer. In vitro platelet function following 5 days of contact with the fiberized resin or the device containing free adsorbents was evaluated using assays for morphology, shape change, hypotonic shock response, aggregation, and GMP-140 (p-selectin) expression. Shape change, aggregation, and hypotonic shock response were evaluated using a Lumi-Aggregometer (Chrono-Log), while GMP-140 was determined by flow cytometry using a Becton-Dickinson FACScan Fluorescence Analyzer (Becton Dickinson).

Psoralen Removal and Platelet Yield and Function

Figure 5:
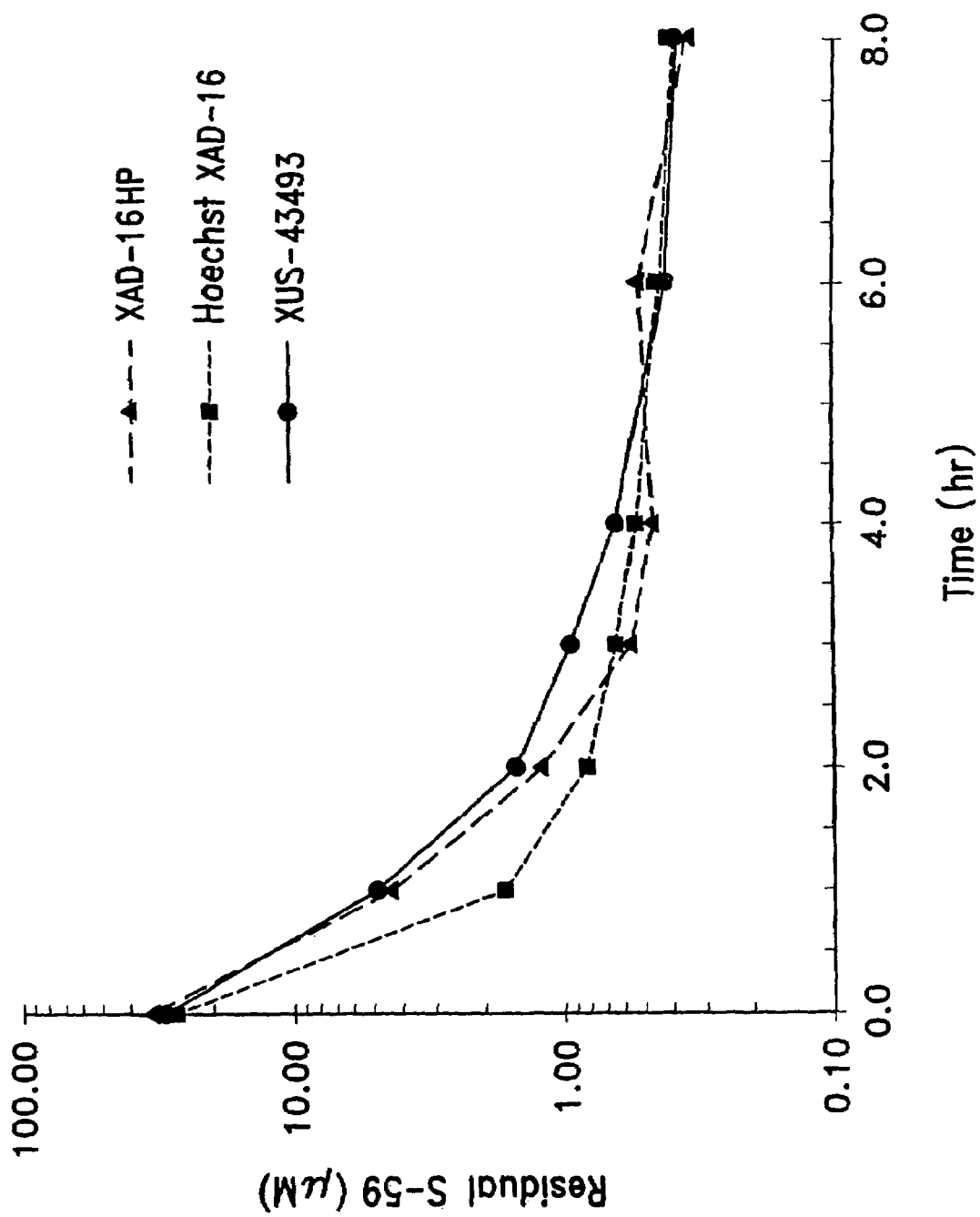
FIG. 5 is a graph showing a comparison of adsorption kinetics for removal of aminopsoralens from platelets with Dowex® XUS-43493 and Amberlite® XAD-16 HP loose adsorbent beads and immobilized adsorbent media containing Amberlite® XAD-16.

FIG. 5 compares the adsorption kinetics for removal of 4'-(4-amino-2-oxa)butyl-4,5',8-trimethyl psoralen from platelets in 35% plasma/65% synthetic media (PAS III) with XUS-43493, XAD-16 HP, and fiberized resin containing XAD-16. Specifically, the data indicated by the circles connected by the solid line represents the device containing the non-immobilized adsorbent XUS-43493 (2.5 g beads; <5% moisture); the data indicated by the triangles connected by the dashed line represents the device containing non-immobilized XAD-16 HP (6.8 g beads; 62.8% moisture); and the data indicated by the squares connected by the dashed line represents the fiberized resin (Hoechst fibers with XAD-16 beads wet in 30% ethanol; 14 cm×14 cm). As the data in FIG. 5 indicate, the kinetics of 4'-(4-amino-2-oxa)butyl-4,5',8-trimethyl psoralen adsorption are very comparable for both the device containing non-immobilized adsorbents and device containing the fiberized resin. Thus, the fiberization process does not appear to have a significant impact on the removal kinetics.

In addition, platelet yield and function of the fiberized resin compared to the loose beads were studied. Specifically, the experiments of this study used i) 6.8 g XAD-16 HP (62.8% moisture); ii) 14 cm×14 cm fiberized XAD-16 (130 g resin/cm$^2$) wet in 30% ethanol; and iii) 2.5 g XUS-43493 (<5% moisture). Duplicate platelet units were prepared for the XAD-16 HP and the fiberized resin samples, but only a single platelet unit was prepared for the XUS-43493 sample. The results are set forth in Table 1.

As indicated in Table 1, the day-5 pH and $pO_2$ values were slightly elevated relative to the day 5 control for samples containing non-immobilized beads (XAD-16 HP and XUS-43493). The experiment with the fiberized resin had pH and $pO_2$ values which were more comparable to the control. Platelet counts indicated a 9-22% platelet loss following 5 days of contact in the control with the fiberized media and the device containing non-immobilized adsorbents. As set forth in Table 1, the fiberized resin gave better yields (9% loss on day 5) and performed better in all in vitro assays when compared to device containing non-immobilized XAD-16 or XUS-43493 adsorbent particles.

TABLE 1

| Sample | pH | $pO_2$ | $pCO_2$ | Platelet Count ($10^{11}$/300 mL) | Shape change | Aggreg | Hypotonic shock response | Morph | GMP-140 (%) |
|---|---|---|---|---|---|---|---|---|---|
| Control Day 0 | 6.98 | 56 | 31 | 4.40 ± 0.18 | | | | | |
| Control Day 5 | 6.89 | 80 | 27 | 4.21 ± 0.16 | 0.58 ± 0.03 | 83 ± 3 | 0.24 ± 0.02 | 297 | 60.6 |
| XAD-16 HP | 6.98 | 110 | 22 | 3.65 ± 0.09 (−13.3%) | 0.38 ± 0.09 | 70 ± 6 | 0.29 ± 0.09 | 278 | 53.8 |
| IAD XAD-16 | 6.90 | 72 | 28 | 3.82 ± 0.15 (−9.3%) | 0.56 ± 0.12 | 80 ± 4 | 0.27 ± 0.04 | 292 | 55.8 |
| XUS-43493 | 6.98 | 115 | 20 | 3.27 ± 0.05 (−22.3%) | 0.37 ± 0.28 | 51 ± 2 | 0.64 ± 0.10 | 271 | 67.0 |

Though an understanding of the mechanism underlying the higher pH and $pO_2$ values observed for the device containing non-immobilized XUS-43493 and XAD-16 HP is not required in order to practice the present invention, the higher values are believed to be caused by a slight decrease in the metabolism of the platelets in the presence of the device containing non-immobilized adsorbent. By comparison, the fiberized media consistently gave day-5 pH and $pO_2$ values which were more comparable to the control than the XUS-43493 or XAD-16 beads.

The day-5 platelet yields were also better for the fiberized media relative to the XUS-43493 and XAD-16 HP adsorbent beads. The 22-28% loss which was observed for the XUS-43493 media was observed on several occasions. However, it should be noted that the current preferred embodiment for a device containing non-immobilized adsorbent with XUS-43493 involves transfer of the platelets from this device after 8 hours of exposure; this procedure results in <5% loss in platelets.

The data presented in Table 1 indicates that the fiberized media gives a higher platelet yield relative to devices containing non-immobilized adsorbents. Surprisingly, the fiberized media also results in better day-5 platelet function as indicated by pH/pO$_2$, shape change, aggregation, morphology and GMP-140. While an understanding of the rationale for the enhanced performance of the fiberized media is not required to practice the present invention, several hypotheses can be proposed. First, the fibers which are attached to the surface of the adsorbent beads may hinder interaction between platelets and the surface of the beads. Second, immobilizing the beads may prevent the beads from interacting and eliminate mechanical effects that are detrimental to platelets. Third, immobilizing the beads may enhance fluid shear at the bead surface, thereby decreasing interaction between platelets and the surface of the beads; by comparison, non-immobilized beads are free to flow with the fluid resulting in low flow of fluid relative to the surface of the bead.

Platelet Loss

When reviewing the above data, it appears that there is some variability in platelet loss from one study to the next. However, the platelet loss expressed as a percentage of the day-5 control count is smaller for studies where the initial platelet count is higher. A study was performed in order to confirm whether the number of platelets that are lost is constant for a given area of material available for platelet adhesion. For this study, two platelet units were pooled and the pool was divided into two samples. One sample was diluted in half with 35% autologous plasma/65% synthetic media (PAS) so that the platelet count was half of the other unit. The platelet mixtures were treated with 4'-(4-amino-2-oxa)butyl-4,5',8-trimethyl psoralen+UVA and were contacted with a device containing non-immobilized adsorbent (2.5 g XUS-43493) for 5 days under the previously discussed standard platelet storage conditions.

The total number of platelets that was lost was virtually identical for the two units, while the losses calculated as a percent differed greatly. Thus, the results indicate that total platelet loss appears to be essentially constant after a period of time; that is, while the percentage of platelet loss varies with the initial platelet count, the total number of platelets lost will be approximately constant when equilibrium is reached. Based on the results set forth in this example, the fiberized resin does not have a negative effect on in vitro platelet function.

Example 2

Fiberized Resin with Activated Charcoal

This example compares the kinetics of removal of 4'-(4-amino-2-oxa)butyl-4,5',8-trimethyl psoralen from platelets and platelet function and morphology for fiberized resin comprising Amberlite® XAD-16 and for fiberized resin comprising immobilized activated charcoal.

Preparation of Fiberized Resin

Hoechst Celanese prepared fiberized resin containing Amberlite® XAD-16 HP (Rohm and Haas). The fiberized resin containing the Amberlite® XAD-16 was prepared as described in the preceding example, including the 30% ethanol wetting step. Hoechst Celanese also prepared fiberized resin containing immobilized activated charcoal (WestVaco) at a loading of 375 g/m$^2$ (AQF-375-B) and 500 g/m$^2$ (AQF-500-B). #In a preferred embodiment, the adsorbent particles is a synthetic activated carbon, including for example, Ambersorb and A-Supra. Synthetic activated carbons are preferred due to their ability to eliminate the amount of particulate material shed from the immobilized adsorption medium this fiberized resin was prepared in a method analogous to that for the fiberized resin containing Amberlite® XAD-16. The composition of the fibers for each fiberized resin was the same.

The fiberized resin was cut into squares (14 cm×14 cm); the resulting sections contained approximately 2.5 g of dry Amberlite® XAD-16. Next, the fiberized resin was sterilized by autoclaving on "wet" cycle for 45 minutes at 121° C. Thereafter, the fiberized resin were inserted into separate sterile, 1-liter PL 2410 Plastic containers (Baxter), and the containers were heat sealed in a laminar flow hood, using sterile scissors, hemostats, and an impulse sealer.

Contacting Fiberized Resin with
Psoralen-Containing PC

Pools of platelet concentrate were prepared by combining 2-3 units of single donor apheresis platelets in 35% autologous plasma/65% synthetic media (PAS III). 4'-(4-amino-2-oxa)butyl-4,5',8-trimethyl psoralen was added in an amount to achieve a final concentration of 150 μM 4'-(4-amino-2-oxa)butyl-4,5',8-trimethyl psoralen. The resulting PC solution was divided into 300 mL units, and the units were placed in PL 2410 Plastic containers (Baxter) and illuminated with 3 J/cm$^2$ of UVA. Following illumination, the treated PCs were transferred into the PL 2410 Plastic containers containing fiberized resin with either XAD-16, AQF-375-B, AQF-500-B or into an empty PL 2410 Plastic container as a control. The PL 2410 Plastic containers were then placed on a Helmer platelet incubator at 22° C. and agitated at approximately 70 cycles/minute.

As performed in the preceding example, samples of each PC were removed at 1-hour, intervals during the first 8 hours of storage for analysis of residual 4'-(4-amino-2-oxa)butyl-4, 5',8-trimethyl psoralen by HPLC. Each sample of PC was diluted 5-fold with sample diluent (final concentration=35% methanol, 25 mM KH$_2$PO$_4$, pH=3.5) containing trimethylpsoralen (TMP) as the internal standard. Proteins and other macromolecules were precipitated by incubating the samples at 4° C. for 30 minutes. The samples were then centrifuged and the supernatant was filtered (0.2 μmeter) and analyzed on a C-18 reversed phase column (YMC ODS-AM 4.6 mm×250 mm) by running a linear gradient from 65% solvent A (25 mM KH$_2$PO$_4$, pH=3.5), 35% B (methanol) to 80% in 20 minutes.

Platelet yield during a 5-day storage period with the fiberized resin or the device containing non-immobilized adsorbent was monitored daily by counting platelets on a Baker System 9118 CP. Blood gases and pH were evaluated using a Ciba-Corning 238 pH/Blood Gas Analyzer. In vitro platelet function following 5 days of contact with the fiberized resin or the device containing non-immobilized adsorbent was evaluated using assays for morphology, shape change, hypotonic shock response, aggregation, and GMP-140 (p-selectin) expression. Shape change, aggregation, and hypotonic shock response were evaluated using a Chrono-Log Lumi-Aggregometer, while GMP-140 was determined by flow cytometry using a Becton-Dickinson FACScan Fluorescence Analyzer.

Psoralen Removal and Platelet Yield and Function

Figure 6:
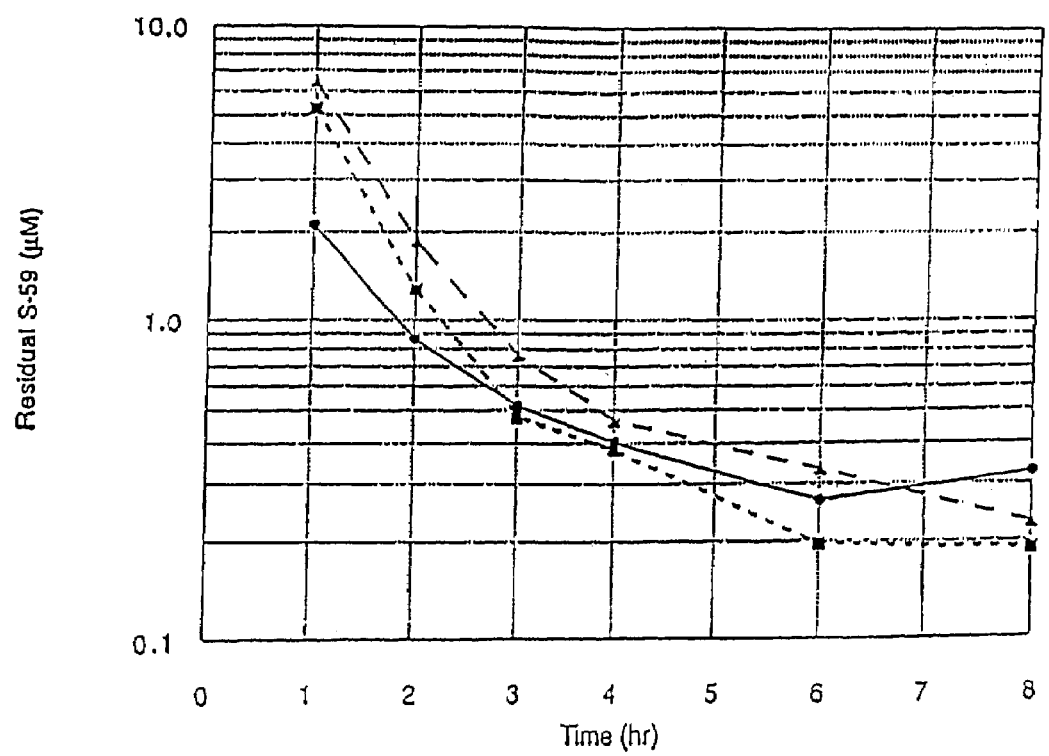
FIG. 6 is a graph showing a comparison of adsorption kinetics for removal of aminopsoralens from platelets with immobilized adsorbent media containing Amberlite® XAD- 16 and immobilized adsorbent media with the two different loadings of activated charcoal. Fiberized XAD-16 data is represented by circles, solid line; fiberized AQF-500-B as squares, short dashes; and, fiberized AQF-375-B as triangle, long dashes.

FIG. 6 compares the adsorption kinetics for removal of 4'-(4-amino-2-oxa)butyl-4,5',8-trimethyl psoralen from platelets in 35% plasma/65% synthetic media (PAS III) with fiberized resin containing XAD-16 and fiberized resin with the two different loadings of activated charcoal. Specifically, the data indicated by the circles represents 4'-(4-amino-2-oxa)butyl-4,5',8-trimethyl psoralen removal with fiberized XAD-16 beads; the data indicated by the squares represents removal with fiberized AQF-500-B; and the data indicated by the triangles represents removal with fiberized AQF-375-B. As the data in FIG. 6 indicate, the kinetics of 4'-(4-amino-2-oxa)butyl-4,5',8-trimethyl psoralen adsorption are very comparable for the different fiberized resin, and the fiberized resin all showed very good kinetics of removal (<0.5 µM residual 4'-(4-amino-2-oxa)butyl-4,5',8-trimethyl psoralen after 4 hours).

Platelet yield and in vitro platelet function for each of the fiberized resin were also evaluated and the data are summarized in Table 2.

TABLE 2

| Sample | pH | $pO_2$ | $pCO_2$ | Platelet Count ($10^{11}$/ 300 mL) | Shape Change | Aggregation |
|---|---|---|---|---|---|---|
| Control Day 0 | 7.07 | 59 | 23 | 3.34 ± 0.13 | 1.17 ± 0.07 | 90 ± 5 |
| Control Day 5 | 6.88 | 112 | 21 | 3.09 ± 0.22 | 0.52 ± 0.02 | 72 ± 8 |
| Fiberized Resin with XAD-16 | 6.93 | 117 | 20 | 2.55 ± 0.16 (−17%) | 0.39 ± 0.13 | 69 ± 6 |
| Fiberized Resin with AQF-500-B | 7.07 | 100 | 20 | 2.83 ± 0.04 (−8%) | 0.74 ± 0.05 | 61 ± 0 |
| Fiberized Resin with AQF-375-B | 6.99 | 107 | 20 | 2.82 ± 0.16 (−9%) | 0.46 ± 0.06 | 65 ± 2 |

Referring to Table 2, the charcoal-based fiberized resin gave good platelet yields with losses of less than 10%; as in the studies of the preceding example, the fiberized resin containing XAD-16 had a slightly higher platelet loss (about 17%). Regarding $pO_2$, the day 5 values for the charcoal fiberized resin are comparable to the control. Though an understanding of why the charcoal fiberized resin had slightly elevated pH values is not required to practice the present invention, it may be an artifact caused by residual extractables (e.g., phosphate) from the activation process; the rapid rise in pH (pH=7.3-7.4) observed after 8 hours of storage of the PC with the charcoal-based fiberized resin supports that idea. The use of USP charcoals, which are associated with fewer extractables, may eliminate the observed initial rise in pH.

The charcoal-based fiberized resin provided good results in both the shape change and aggregation assays. Although the shape change result for the AQF-500-B fiberized resin is better than that of the control, the platelets associated with AQF-500-B performed slightly poorer in the aggregation assay.

Example 3

Effect of pHEMA Coating on Adsorbent Hemocompatibility

This example compares the kinetics of removal of 4'-(4-amino-2-oxa)butyl-4,5',8-trimethyl psoralen from platelets and platelet function and morphology for both Dowex® XUS-43493 and fiberized resin containing Amberlite® XAD-16 coated with pHEMA.

Preparation of pHEMA-Coated Adsorbent Beads and Fiberized Resin

Dowex® XUS-43493 (commercially known as Optipore® L493) containing approximately 50% water by weight was obtained from Dow, and polymerized HEMA with a viscosity average molecular weight of 300 kD was obtained from Scientific Polymer Products. Prior to coating, the adsorbent beads were dried to a water content of <5%. A stock solution of pHEMA was prepared by dissolving the polymer in 95% denatured ethanol/5% water to achieve a pHEMA concentration of 50 mg/ml.

The coating process was performed by International Processing Corp. in a 9-inch Wurster fluidized bed coater with a charge of approximately 4 kg (dry) of adsorbent. The coating process involved a pHEMA flow rate of 60-70 g/min, an inlet temperature of 50° C., and an air flow rate of approximately 200 ft$^3$/min. Samples (50 g) of coated adsorbent were removed during the coating process so that coating levels ranging from 3-18% (w/w) pHEMA were obtained; adsorbent beads coated with 3.7%, 7.3%, and 10.9% pHEMA (w/w) were used in the studies described below.

A device containing non-immobilized dry (uncoated) Dowex® XUS-43493 (2.5 g) and pHEMA-coated Dowex® XUS-43493 (3.0 g or 5.0 g) were prepared by placing the desired mass of adsorbent into a square 30 µm polyester mesh pouch (7 cm×7 cm). The adsorbent-filled pouches were inserted into separate sterile, 1-liter PL 2410 Plastic containers (Baxter) and heat sealed with an impulse sealer. Thereafter, the adsorbent-filled pouches containing PL-2410 Plastic containers were sterilized by either E-beam (NIS) or gamma irradiation (SteriGenics) to 2.5 MRad; as previously alluded to, E-beam sterilization is generally preferred.

Hoechst Celanese prepared fiberized resin containing Amberlite® XAD-16 according to the method described in Example 1. The fiberized resin was cut into squares (14 cm×14 cm); the resulting sections contained approximately 2.5 g of dry Amberlites XAD-16. The Amberlite® XAD-16 of the fiberized resin was simultaneously wet and coated with pHEMA by soaking in a solution containing 50 mg/mL pHEMA in 95% ethanol/5% distilled water. Residual ethanol was removed by rinsing twice in saline for 10 minutes. This procedure resulted in a coating of approximately 6% (w/w) pHEMA. The fiberized resin was then sterilized by autoclaving on "wet" cycle for 45 minutes at 121° C. Thereafter, the fiberized resin was inserted into separate sterile, 1-liter PL 2410 Plastic containers (Baxter) and heat sealed in a laminar flow hood, using sterile scissors, hemostats, and an impulse sealer.

Contacting pHEMA-Coated Adsorbent Beads and Fiberized Resin With Psoralen-Containing PC Pools of platelet concentrate were prepared by combining units of single donor apheresis platelets in 35% autologous plasma/65% synthetic media (PAS III). 4'-(4-amino-2-oxa)butyl-4,5',8-trimethyl psoralen was added in an amount to achieve a final concentration of 150 µM 4'-(4-amino-2-oxa)butyl-4,5',8-trimethyl psoralen. The resulting PC solution was then divided into 300 mL units, and the units were placed in PL 2410 Plastic containers (Baxter) and illuminated with 3 J/cm$^2$ of UVA. Following illumination, the treated PCs were transferred into the PL 2410 Plastic containers containing the devices as indicated in the following result sections. Control samples without an adsorption device were also prepared.

The PL 2410 Plastic containers were then placed on a Helmer platelet incubator at 22° C. and agitated at approximately 70 cycles/minute.

Samples of each PC were removed at 1-hour intervals during the first 8 hours of storage for analysis of residual 4'-(4-amino-2-oxa)butyl-4,5',8-trimethyl psoralen by HPLC. Each sample of PC was diluted 5-fold with sample diluent (final concentration=35% methanol, 25 mM $KH_2PO_4$, pH=3.5) containing trimethylpsoralen (TMP) as the internal standard. Proteins and other macromolecules were precipitated by incubating the samples at 4° C. for 30 minutes. The samples were then centrifuged and the supernatant was filtered (0.2µ meter) and analyzed on a C-18 reversed phase column (YMC ODS-AM 4.6 mm×250 mm) by running a linear gradient from 65% solvent A (25 mM $KH_2PO_4$, pH=3.5), 35% B (methanol) to 80% in 20 minutes.

Platelet yield after a 5-day storage period with the fiberized resin or the device containing non-immobilized adsorbent was determined by counting platelets on a Baker System 9118 CP. Blood gases and pH were evaluated using a Ciba-Corning 238 pH/Blood Gas Analyzer. In vitro platelet function following 5 days of contact with the fiberized resin or the control device containing non-immobilized adsorbent was evaluated using assays for morphology, shape change, hypotonic shock response, aggregation, and GMP-140 (p-selectin) expression. Shape change, aggregation, and hypotonic shock response were evaluated using a Chrono-Log Lumi-Aggregometer, while GMP-140 was determined by flow cytometry using a Becton-Dickinson FACScan Fluorescence Analyzer.

Effect of pHEMA Coating on Psoralen Removal

Figure 7:
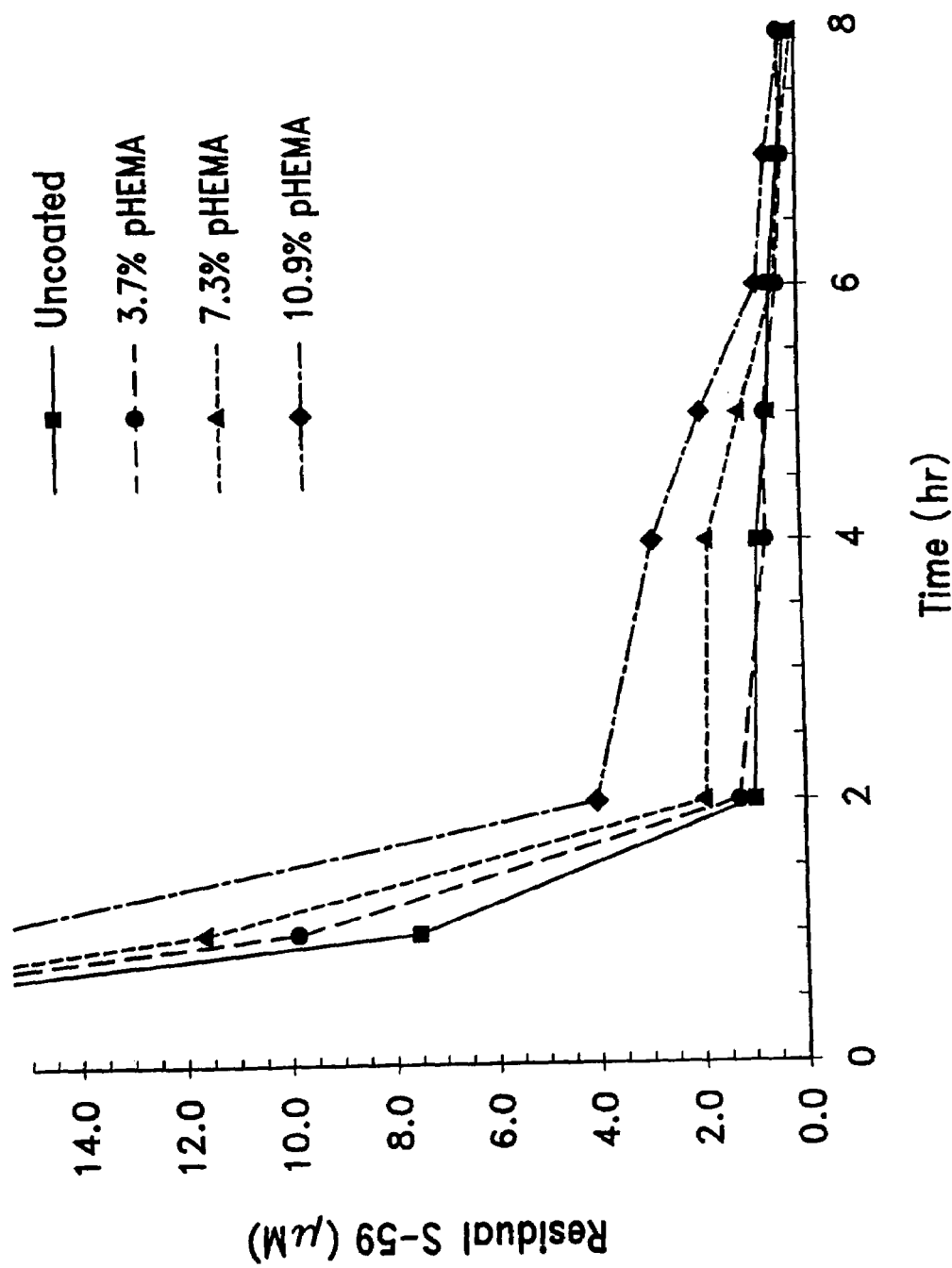
FIG. 7 is a graph showing a comparison of the adsorption kinetics for removal of aminopsoralens from platelets with p(HEMA)-coated and uncoated Dowex® XUS-43493 beads.

FIG. 7 compares the adsorption kinetics for removal of 4'-(4-amino-2-oxa)butyl-4,5',8-trimethyl psoralen from platelets in 35% plasma/65% synthetic media (PAS III) with pHEMA-coated and uncoated Dowex® XUS-43493 beads.

Specifically, 4'-(4-amino-2-oxa)butyl-4,5',8-trimethyl psoralen removal with 3.0 g Dowex® XUS-43493 coated with 3.7% (w/w) pHEMA is represented by the circles, with 7.3% (w/w) pHEMA is represented by the triangles, and with 10.9% (w/w) pHEMA is represented by the diamonds; the squares represent 4'-(4-amino-2-oxa)butyl-4,5',8-trimethyl psoralen removal with 2.5 g (dry) uncoated Dowex® XUS-43493. As the data in FIG. 7 indicate, the kinetics of 4'-(4-amino-2-oxa)butyl-4,5',8-trimethyl psoralen adsorption decreased as the level of pHEMA coating was increased. While the mechanism need not be understood in order to practice the invention, this decrease is believed to be due to an increase in resistance to diffusion of 4'-(4-amino-2-oxa)butyl-4,5',8-trimethyl psoralen to the interior of the adsorbent particles.

The adsorption kinetics of 4'-(4-amino-2-oxa)butyl-4,5',8-trimethyl psoralen removal were also determined with 5.0 g Dowex® XUS-43493 coated with 3.7%, 7.3%, and 10.9% (w/w) pHEMA. The results (not shown) indicated that the removal kinetics for the beads coated with 10.9% pHEMA were comparable to that with the uncoated (control) beads.

Effect of pHEMA Coating on Platelet Yield

The effect of pHEMA on platelet yield was determined in two studies using different amounts of adsorbent (3.0 and 5.0 g) but the same levels of pHEMA coating (3.7%, 7.3%, and 10.9% [w/w]) in each. Platelet yields were calculated relative to the platelet count on day 5 for treated PC which was not contacted with a device containing non-immobilized adsorbents. As the results in Table 3 indicate, when 3.0 g of XUS-43493 were tested, there was a nominal dose response on day 5 platelet yield with increasing pHEMA coating levels; those results suggest that a low level of pHEMA coating may be most effective since it has a smaller effect on 4'-(4-amino-2-oxa)butyl-4,5',8-trimethyl psoralen removal kinetics while still inhibiting platelet adhesion to the adsorbent surface. In contrast to the nominal effect seen with 3.0 g of XUS-43493, a dose response was observed when 5.0 g were tested—increasing pHEMA coating levels did increase the day 5 platelet yield. However, yields were still lower than those observed when 3.0 g of adsorbent beads were used.

TABLE 3

| Polymer Coating | Coating Level (%) | Adsorbent Mass (g) | Platelet Yield, Day 5 (%)* |
|---|---|---|---|
| None | 0 | 2.5 | 73.1 |
| pHEMA | 3.7 | 3.0 | 91.4 |
| pHEMA | 7.3 | 3.0 | 87.7 |
| pHEMA | 10.9 | 3.0 | 89.0 |
| pHEMA | 3.7 | 5.0 | 71.8 |
| pHEMA | 7.3 | 5.0 | 80.2 |
| pHEMA | 10.9 | 5.0 | 86.6 |

The results presented in Table 3 suggest that the use of a lower mass of adsorbent (e.g., 2.5 -3.0 g) along with a low level of pHEMA coating (e.g., ≦3.0% w/w) will provide the best platelet yield. As previously indicated, the optimum level of pHEMA coating is the minimum coating at which a protective effect on platelet yield and in vitro platelet function is observed.

Effect of pHEMA Coating and Sterilization on Platelet Function

It was previously indicated that methods of sterilization may have a substantial effect on adsorbent function since the pHEMA coating can be crosslinked or cleaved by the radiation. In order to evaluate this effect, a study was performed with devices containing non-immobilized pHEMA-coated (3.7% w/w) and uncoated XUS-43493 sterilized with either 2.5 MRad E-beam or 2.5 MRad gamma irradiation. Each device contained 2.5 g (dry) of non-immobilized coated or uncoated XUS-43493 housed in a square 30 µm polyester mesh pouch (7 cm×7 cm); the control comprised treated PC stored in a PL 2410 Plastic container alone. The results are summarized in Table 4.

TABLE 4

| Sample | pH | $pO_2$ | Platelet Count ($10^{11}$/300 L) | Shape Change | Aggregation | HSR | Morphology | GM-140 Activation (%) |
|---|---|---|---|---|---|---|---|---|
| Control Day 0 | 7.03 | 67 | 4.94 ± 0.24 | — | — | — | — | — |

TABLE 4-continued

| Sample | pH | pO$_2$ | Platelet Count (10$^{11}$/300 L) | Shape Change | Aggregation | HSR | Morphology | GM-140 Activation (%) |
|---|---|---|---|---|---|---|---|---|
| Control Day 5 | 6.87 | 84 | 4.58 ± 0.08 (−0%) | 0.96 ± 0.05 | 76 ± 2 | 0.35 ± 0.03 | 295 | 70.0 |
| Uncoated XUS-43493 | 6.95 | 128 | 3.49 ± 0.08 (−23.8%) | 0.38 ± 0.00 | 44 ± 0 | 0.47 ± 0.12 | 260 | 58.3 |
| 3.7% pHEMA XUS-43493 Gamma | 6.93 | 108 | 4.19 ± 0.09 (−8.5%) | 0.59 ± 0.03 | 59 ± 5 | 0.32 ± 0.04 | 240 | 58.5 |
| 3.7% pHEMA XUS-43493 E-beam | 6.88 | 92 | 4.35 ± 0.11 (−5.0%) | 0.71 ± 0.06 | 69 ± 9 | 0.40 ± 0.04 | 264 | 54.8 |

Referring to Table 4, the day-5 pH values appear to be very stable compared to the control. The pO$_2$ value measured with the device containing non-immobilized uncoated adsorbent is slightly elevated, suggesting a mild decrease in metabolism; coating with pHEMA appeared to reduce this effect, with the results for the E-beam sterilized device containing non-immobilized adsorbent closer to the control than those for the gamma sterilized device.

Platelet yields were very good for both of the pHEMA-coated samples, the E-beam sterilized sample performing slightly better. Shape change and aggregation exhibited a pattern similar to that for yield, with the device containing non-immobilized uncoated adsorbent giving the lowest values and the pHEMA-coated/E-beam sterilized sample providing higher values similar to the control. The samples treated with a device containing non-immobilized adsorbents performed as well as or better than the control in the hypotonic shock response (HSR) assay. Samples that were treated with the devices containing non-immobilized adsorbents gave lower morphology scores than the control, but showed lower levels of activation as indicated by the GMP-140 assay.

Another hemocompatibility study was performed comparing a device containing non-immobilized uncoated XUS-43493 (2.5 g beads; 30 μm polyester mesh pouch; 7 cm×7 cm), uncoated fiberized resin (14 cm×14 cm) containing Amberlite® XAD-16, and fiberized resin containing pHEMA-coated Amberlite® XAD-16. The favorable effect of pHEMA on the fiberized resin is indicated by the results presented in Table 5

TABLE 5

| Sample | pH | pO$_2$ | Platelet Count (10$^{11}$/300 L) | Shape Change | Aggregation | HSR | Morphology | GM-140 Activation (%) |
|---|---|---|---|---|---|---|---|---|
| Control Day 0 | 7.11 | 50 | 3.01 ± 0.10 | — | — | — | — | — |
| Control Day 5 | 6.91 | 122 | 2.85 ± 0.16 (−0%) | 0.60 ± 0.09 | 78 ± 4 | 0.31 ± 0.01 | 302 | 72.5 |
| Uncoated XUS-43493 | 7.00 | 151 | 2.11 ± 0.07 (−26.0%) | 0.35 ± 0.03 | 55 ± 4 | 0.57 ± 0.03 | 267 | 68.7 |
| Uncoated Fiberized Resin with XAD-16 | 6.94 | 126 | 2.23 ± 0.13 (−21.8%) | 0.52 ± 0.03 | 82 ± 4 | 0.45 ± 0.01 | 297 | 65.3 |
| pHEMA-Fiberized Resin with XAD-16 | 6.95 | 120 | 2.44 ± 0.11 (−14.4%) | 0.59 ± 0.01 | 86 ± 5 | 0.46 ± 0.02 | 305 | 63.0 |

As indicated by the data regarding in vitro platelet function and platelet yield in Table 5, coating with pHEMA brought the pO$_2$ values for the fiberized resin closer to that observed for the control. The pHEMA-coated fiberized resin also exhibited higher platelet yield than the uncoated fiberized resin. The results indicate that the pHEMA-coated fiberized resin performed better than the uncoated XUS-43493 beads in all in vitro platelet function assays. Moreover, the uncoated fiberized resin performed better than the uncoated XUS-43493 beads in most in vitro platelet function assays.

Example 4

Effect of Glycerol and Polyethylene Glycol on Adsorbent Capacity

This example examines the effect of glycerol and polyethylene glycol as stabilizing agents on adsorbent capacity and kinetics of removal of aminopsoralens from plasma. Free (i.e., not fiberized) Amberlite® XAD-16 and Dowex® XUS-43493 adsorbent beads were used in the experiments of this example.

Methodology

Amberlite® XAD-16 HP (Rohm & Haas (Philadelphia, Pa.)) and Dowex® XUS-43493 (Supelco, Bellefonte, Pa.) were dried to <5% water in a 80° C. oven. Known masses of adsorbent were soaked in ethanol solutions containing 0-50% glycerol, 50% PEG-200 or 50% PEG-400 (glycerol, PEG-200, and PEG-400 from Sigma). Following a 15 minute incubation period at room temperature, the excess solvent was removed and the samples were dried overnight in a 80° C. oven; drying the adsorbent at temperatures >120° C. was avoided since changes in adsorbent properties (e.g., pore melting) were previously observed at higher temperatures. After drying, adsorbent samples were weighed to determine the mass of stabilizing agent per mass of adsorbent.

Several individual studies were performed. Control samples of "non-wet" adsorbent and "optimally wet" adsorbent were included in the studies as described below. The non-wet samples of adsorbent were dried adsorbent which was not subjected to any pre-treatment, while the optimally wet samples of adsorbent were prepared by wetting the adsorbent with 30% ethanol/70% $dH_2O$. The optimally-wet adsorbent was rinsed with $dH_2O$ to remove residual ethanol. The adsorbent was prepared just prior to the adsorption study to assure that drying did not occur.

Each of the adsorption studies was performed using 100% human plasma containing 150 μM 4'-(4-amino-2-oxa)butyl-4,5',8-trimethyl psoralen spiked with $^3H$-4'-(4-amino-2-oxa)butyl-4,5',8-trimethyl psoralen. Plasma (6.0 mL) was added to vials containing adsorbent treated with different stabilizing agents. Masses of adsorbent were corrected for glycerol or PEG content to give 0.2 g of adsorbent. The vials were placed on a rotator and agitated at room temperature. Plasma samples were removed at various times and levels of residual $^3H$-4'-(4-amino-2-oxa)butyl-4,5',8-trimethyl psoralen were determined. Samples (200 μL) were diluted in 5.0 mL of Optiphase HiSafe Liquid Scintillation Cocktail (Wallac) and were counted on a Wallac 1409 Liquid Scintillation Counter (Wallac).

Figure 8:
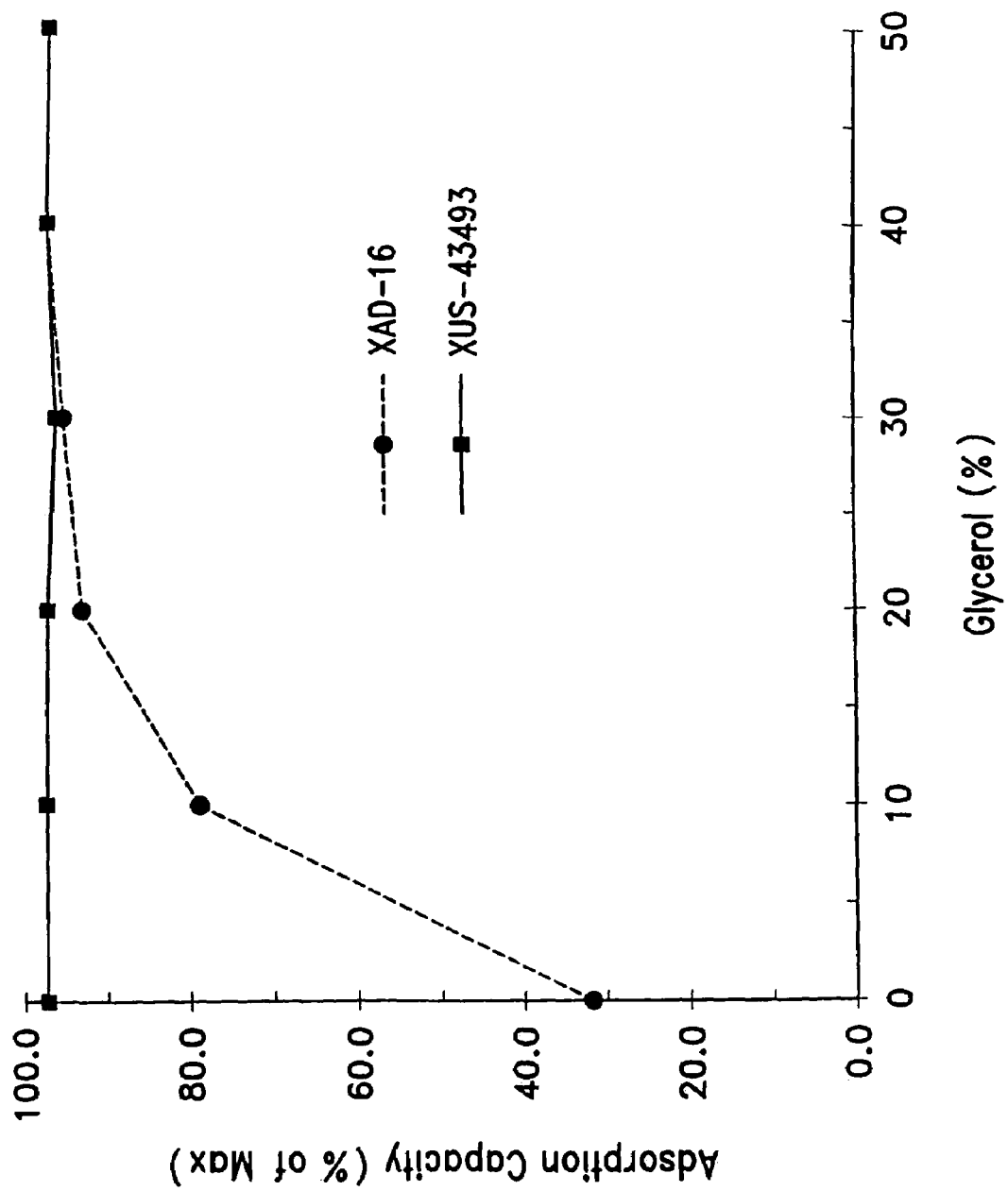
FIG. 8 is a graph showing a comparison of the effect of pre-treatment with solutions containing glycerol on the relative adsorption capacity of Amberlite® XAD-16 and Dowex® XUS-43493 for aminopsoralens.

Adsorption Capacities of Amberlite® XAD-16 and Dowex® XUS-43493 Treated with Glycerol FIG. 8 compares the effect of pre-treatment with ethanol solutions containing various levels of glycerol on relative 4'-(4-amino-2-oxa)butyl-4,5',8-trimethyl psoralen adsorption capacity in 100% plasma for Amberlite® XAD-16 and Dowex® XUS-43493. Adsorbent samples were wet in the ethanol/glycerol solutions for 15 minutes prior to drying for 48 hours at 80° C. Single measurements of adsorption capacity were made after 4 hours of contact. Referring to FIG. 8, glycerol content shown on the x-axis is weight/volume percent of glycerol in ethanol. Adsorption capacities shown on the y-axis are percentages relative to the adsorption capacity of the optimally wet adsorbent sample. The adsorption capacity of XUS-43493 is represented by the squares, while that of XAD-16 is represented by the circles.

As the data in FIG. 8 indicate, the capacity of XAD-16 increased from about 30% in the dry sample to over 90% in the sample wet in a 20% glycerol solution. These results indicate that very low levels of glycerol are required for maintaining high adsorbent capacity after drying. Control samples that were wet in 50% ethanol/50% $dH_2O$ (no glycerol) prior to drying demonstrated adsorption capacities which were similar to untreated samples that were dried. In contrast, the XUS-43493 samples did not show any effect of glycerol on adsorption capacity; adsorption capacity approached 100% at all levels of glycerol. While not critical to the practice of the present invention, this observation supports the hypothesis that glycerol acts to prevent the adsorbent pores from collapsing during drying; because XUS-43493 has a highly crosslinked structure, it is not subject to pore collapse upon drying.

Samples that were treated with glycerol appeared to be very stable to drying. No changes were observed in adsorption capacity for samples that were stored for 7 days in a laminar flow hood (data not shown).

In a preferred embodiment of the present invention, 2.5 g dry of adsorbent are used for the removal of psoralen and psoralen photoproducts from each unit of platelets. Soaking the adsorbent in 30% glycerol/70% ethanol, followed by drying, results in adsorbent which contains approximately 50% glycerol. A 5.0 g sample of adsorbent would therefore contain 2.5 g dry adsorbent and 2.5 g of glycerol. Thus, a typical 300 mL unit of platelets would contain 0.8% glycerol, a level thought to be acceptable for transfusion.

Figure 9:
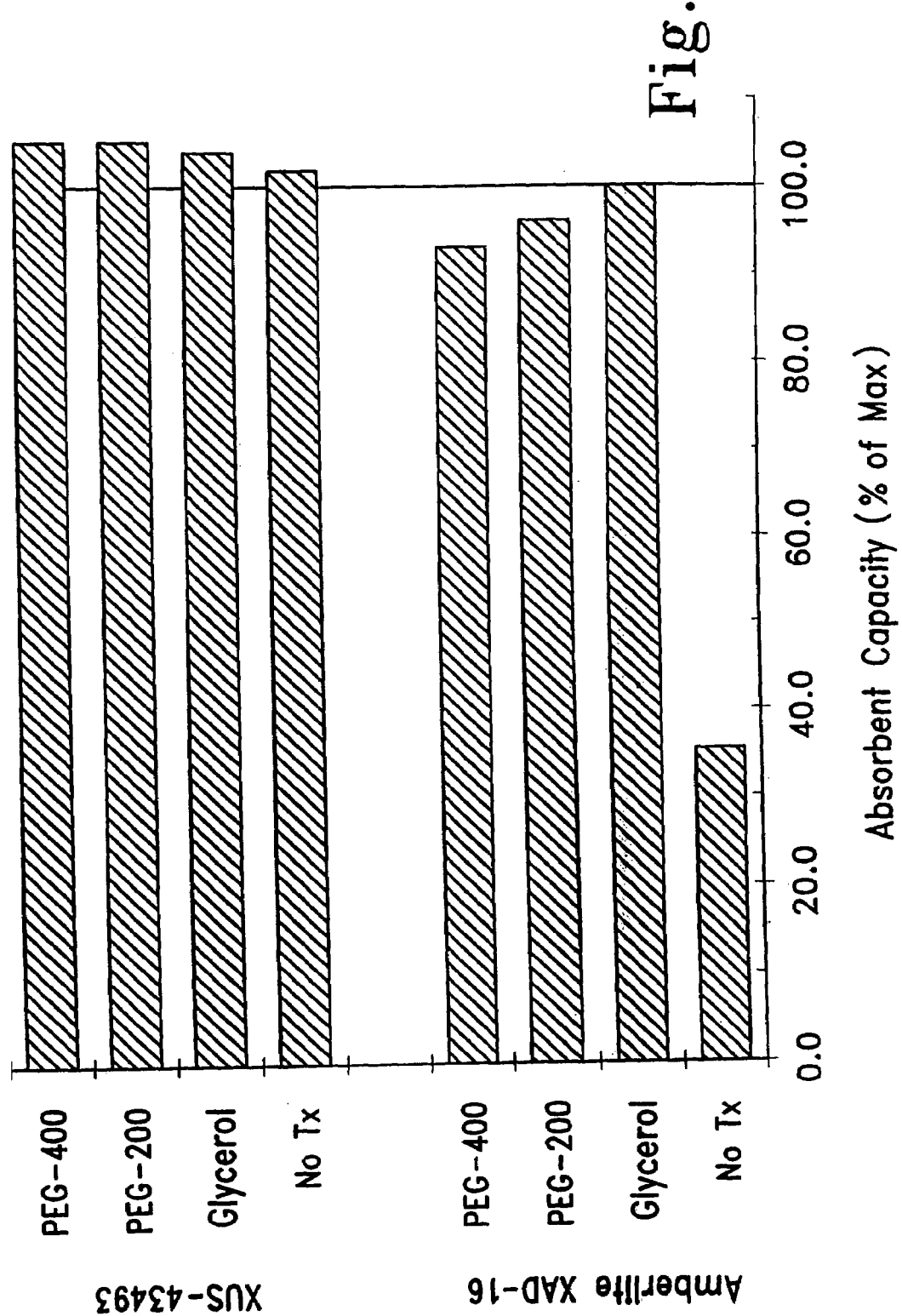
FIG. 9 is a graph showing a comparison of the effect of wetting solution on 4'-(4-amino-2-oxa)butyl-4,5',8-trimethyl psoralen adsorption capacities for dried adsorbent in 100% plasma for Amberlite® XAD-16 (bottom) and Dowex® XUS-43493 (top); the samples that were not wet in an ethanol solution are labeled "No Tx". Adsorption capacities are reported as percentages relative to the capacity of optimally wet adsorbent.

Adsorption Capacities of Amberlite® XAD-16 and Dowex® XUS-43493 Treated With Glycerol or PEG Additional studies were performed with the low molecular weight polyethylene glycols PEG-200 and PEG-400, low-toxicity agents that are nonvolatile and are soluble in ethanol and water. Samples of adsorbent were treated for 15 minutes in 50% solutions of PEG-400, PEG-200 or glycerol in ethanol. FIG. 9 compares the effect of the stabilizing agents on 4'-(4-amino-2-oxa)butyl-4,5',8-trimethyl psoralen adsorption capacities with dried adsorbent in 100% plasma for Amberlite® XAD-16 (bottom) and Dowex® XUS-43493 (top); the samples that were not wet are labeled "No Tx". Adsorbent capacities are reported as percentages relative to the capacity of optimally wet adsorbent.

As indicated by the data in FIG. 9 and predictable based on the its "macronet" structure, the capacity of Dowex® XUS-43493 was not affected by drying ("No Tx" sample). Conversely, the Amberlite® XAD-16 had approximately 35% of the maximum capacity when dried. Treating XAD-16 with glycerol, PEG-200, and PEG-400 all improved the capacity of the dried adsorbent; the adsorbent capacities with each were all greater than 90%, with glycerol>PEG-200>PEG-400. Though an understanding of the precise mechanism of action is not required to practice the present invention, differences in capacity between the glycerol and the two PEG solutions may be caused by decreasing penetration of the stabilizing agent with increasing molecular weight. That is, during the 15 minute application procedure, the glycerol (MW=92.1) may be able to penetrate the adsorbent pores more completely than either PEG-200 (MW=190-210) or PEG-400 (MW=380-420), which diffuse more slowly because of their larger size.

Adsorption Kinetics of Amberlite® XAD-16 Treated with Glycerol or PEG

Figure 10:
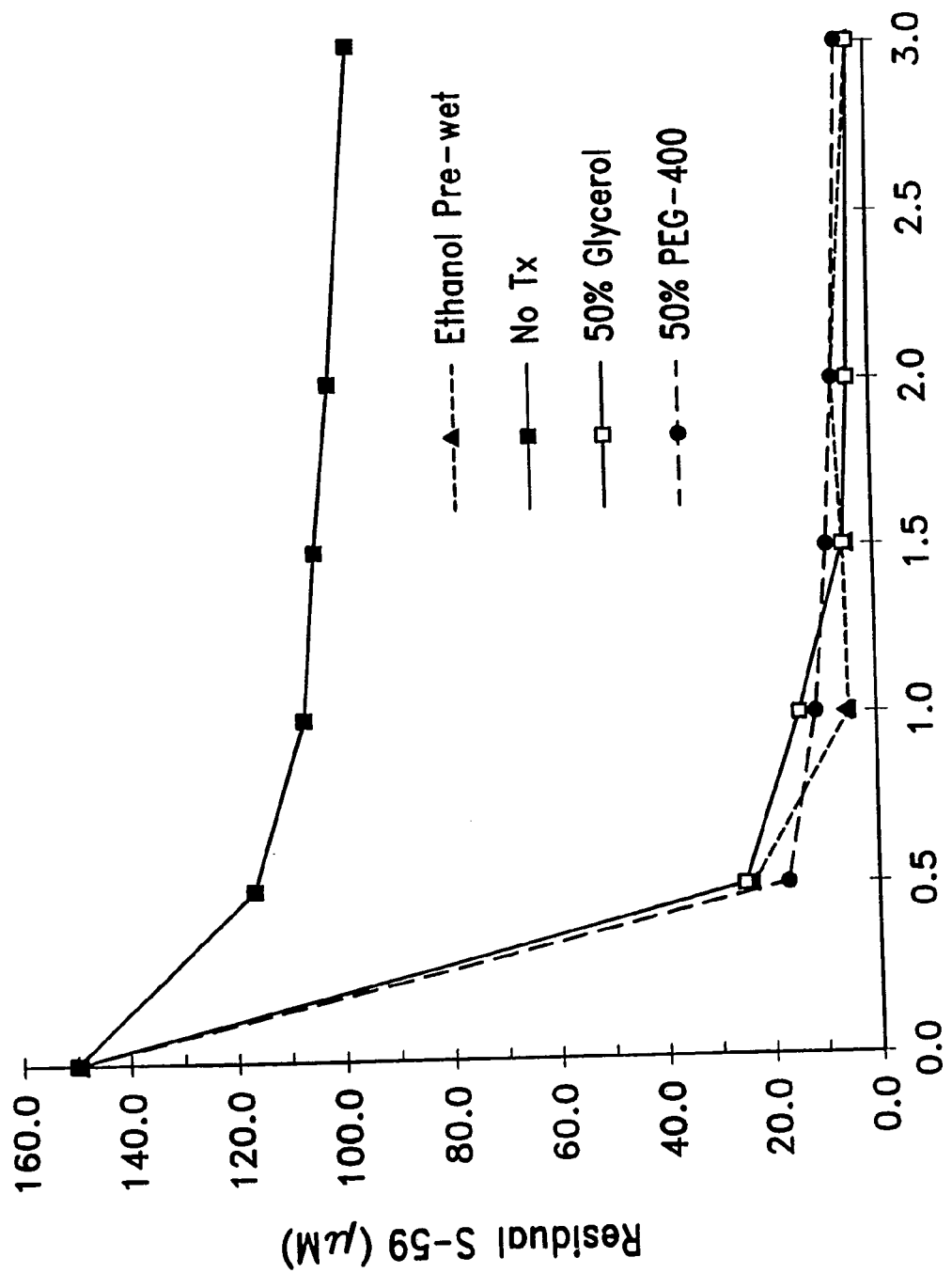
FIG. 10 is a graph showing a comparison of adsorption of aminopsoralens over a 3-hour period from plasma using Amberlite® XAD-16 wet in several different solutions.

A study was also performed to determine whether filling the pores of the adsorbent with glycerol or PEG results in reduced adsorption kinetics. FIG. 10 compares adsorption of 4'-(4-amino-2-oxa)butyl-4,5',8-trimethyl psoralen over a 3-hour period from 100% plasma using Amberlite® XAD-16 wet in several different solutions. Specifically, the data in FIG. 10 represents XAD-16 i) wet prior to drying with a 50% solution of glycerol (open squares connected by solid lines), ii) wet prior to drying with a 50% solution of PEG-400 (shaded circles connected with dashed lines), iii) pre-wet, i.e., just prior to initiating the study, with 50% ethanol/50% dH$_2$O (shaded triangles connected by dashes), and iv) not subjected to any treatment (shaded squares connected by solid lines; "No Tx"). The data in FIG. 10 demonstrate that Amberlite® XAD-16 samples that were wet in 50% glycerol/50% ethanol or 50% PEG-400/50% ethanol solutions had adsorption kinetics which were very close to the sample that was optimally wet in ethanol (i.e., the sample pre-wet with ethanol). The XAD-16 sample that was dried but not treated (No Tx) achieved only about 30% removal by 3 hours.

The data presented in this example indicate that treating Amberlite® XAD-16 with stabilizing agents in the form of solutions containing 50% ethanol and 50% glycerol, PEG-200, or PEG-400 can prevent loss of adsorption capacity associated with drying. The results obtained with these stabilizing agents suggest that low molecular weight wetting agents represent viable methods for enhancing adsorbent function.

Example 5

Removal of Methylene Blue from FFP

This example is directed at the ability of a variety of different polymeric adsorbent materials to remove methylene blue from fresh frozen plasma.

The experiments of this example evaluated "free" adsorbent resin (i.e., not incorporated into device containing non-immobilized adsorbents) and fiberized resin. The free adsorbent resins tested were Amberlite® XAD-16 HP (Rohm and Haas), MN-200 (Purolite), and Dowex® XUS-43493 (Dow Chemical Co.). The XAD-16 HP came in a hydrated state so that no pre-treatment (i.e., no wetting) was necessary, and the MN-200 was also supplied in a fully hydrated state; the XUS-43493 was dry.

Fiberized resin containing XAD-16 was prepared as generally described in Example 1. Briefly, a 2 cm×7 cm (i.e., 14 cm$^2$) strip of fiberized resin containing 130 g/m$^2$ XAD-16 was first wet in 70% ethanol and then rinsed exhaustively in distilled water.

A stock solution of methylene blue (10 mM) was prepared by dissolving U.S.P. methylene blue (Spectrum) in distilled water. The stock solution of methylene blue was added to a sample of 100% plasma to give a final concentration of 10 µM. Samples of the "free" adsorbent resin (i.e., XAD-16 HP, MN-200, and XUS-43493) were weighed into 50 mL polypropylene tubes for adsorption studies. The water content of each adsorbent was determined by measuring mass loss upon drying. The mass of each adsorbent was corrected for water content so that the equivalent of 0.25 g dry adsorbent was used for each.

A 30 mL sample of the 100% plasma containing 10 µM methylene blue was added to each vial. The vials were placed on a rotator at room temperature. Samples (200 µL) were removed from each vial at 15 minute intervals and assayed for residual methylene blue by HPLC. Each sample of plasma was diluted 5-fold with sample diluent (final concentration=35% methanol, 25 mM KH$_2$PO$_4$, pH=3.5). Proteins and other macromolecules were precipitated by incubating the samples at 4° C. for 30 minutes. Samples were centrifuged and the supernatant was filtered (0.2 µm) and analyzed on a C-18 reversed phase column (YMC ODS-AM, 4.6 mm×250 mm) by running a linear gradient from 65% solvent A (25 mM KH$_2$PO$_4$, pH=3.5), 35% B (Methanol) to 80% B in 20 minutes. The limit of detection for the HPLC assay was approximately 0.5 µm methylene blue.

Figure 11:
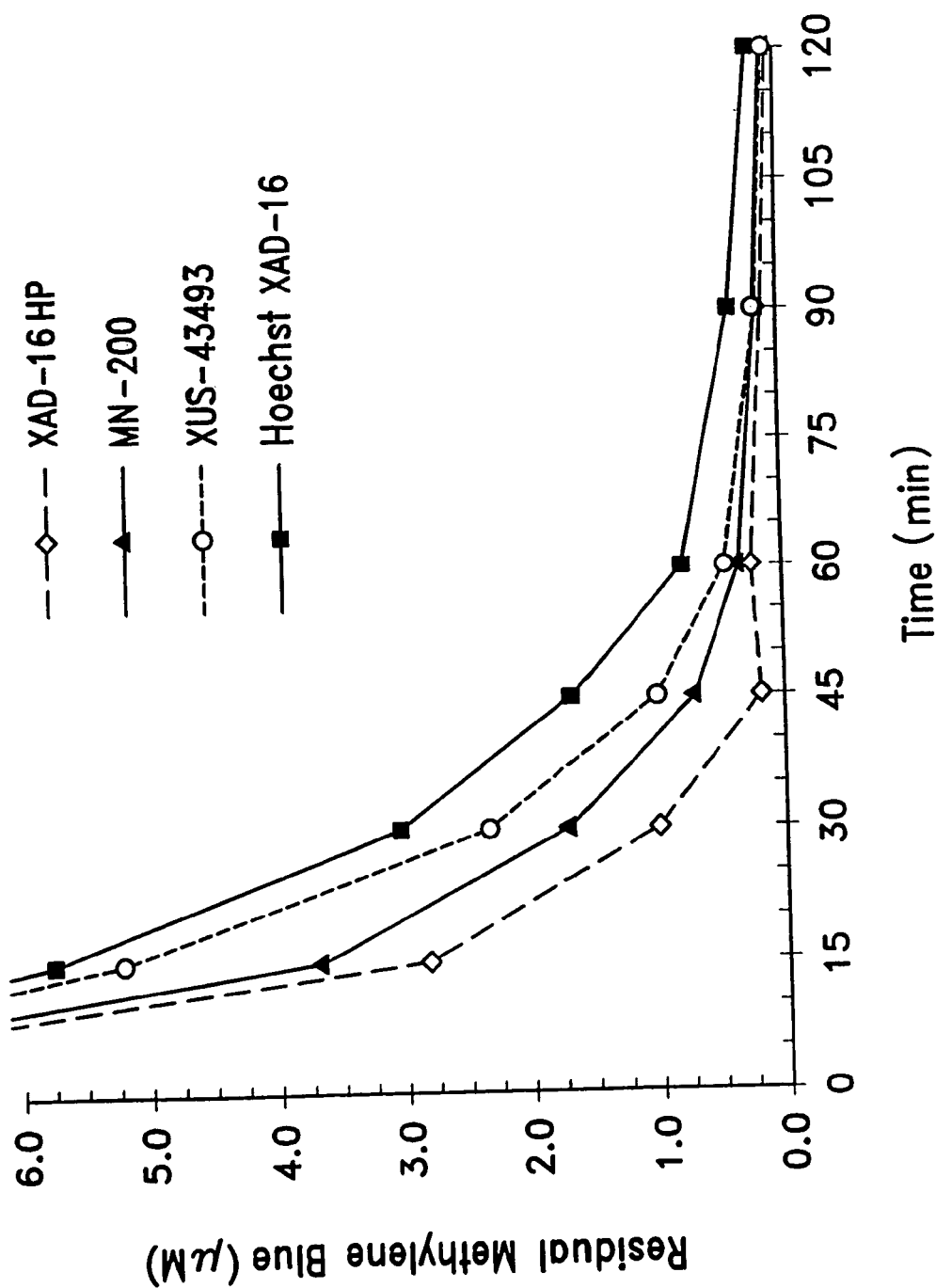
FIG. 11 is a graph showing a comparison of the kinetics of adsorption of methylene blue over a 2-hour period from plasma.

FIG. 11 compares the kinetics of adsorption of methylene blue over a 2-hour period from 100% plasma. Referring to FIG. 11, XAD-16 HP data is represented by open diamonds connected by dashed lines, the MN-200 data is represented by shaded triangles connected by solid lines, the XUS-43493 data is represented by open circles connected by dashed lines, and the fiberized resin containing XAD-16 is represented by shaded squares connected by solid lines. As the data indicate, the XAD-16 HP and MN-200 gave the fastest adsorption kinetics, followed by XUS-43493. The slightly slower kinetics of the XUS-43493 may be a result of slower wetting, as it was used in the dry state. Finally, the fiberized resin containing XAD-16 had the slowest adsorption kinetics. This may have resulted from poor contacting between the fiberized resin and plasma during the batch incubation, as a portion of the 14 cm$^2$ strip of fiberized resin was not completely submersed in the plasma throughout the adsorption study, thereby reducing the effective contact area between the adsorbent and plasma.

The data indicate that non-psoralen pathogen-inactivating compounds like the phenothiazine dyes can be removed from blood products using the resins and fiberized resin contemplated for use with the present invention.

Example 6

Removal of Acridine Compounds from Packed Red Blood Cells

This example is directed at the ability of a variety of different resin materials to remove acridine compounds from packed red blood cells (PRBCs). More specifically, the experiments of this example evaluate the removal of the acridine compound, 5-[(β-carboxyethyl)amino]acridine, from PRBCs.

The chemical structures of several acridines are depicted in FIG. 12. As indicated in FIG. 12, 9-amino acridine and 5-[(β-carboxyethyl)amino]acridine are aminoacridines.

Resin Selectivity

Equilibrium adsorption of compound 5-[(β-carboxyethyl) amino]acridine was studied with several types of resins. The polymeric adsorbent resins evaluated were Amberlite® XAD-2, XAD-4, XAD-7, and XAD-16 HP (Rohm and Haas); Purolite® MN-150, MN-170, MN-200, MN-300, MN-400, MN-500, and MN-600; and Dowex® XUS-43493 and XUS-40285 (Dow Chemical Co.). In addition, several Amberlite® anion exchange resins (IRA-958, IRA-900, IRA-35, IRA-410 and IRA-120; Rohm and Haas) and an Amberlite® weak cation exchange resin (DP-1; Rohm and Haas) were tested. Moreover, several charcoals were evaluated, including Hemosorba® AC (Asahi), PICA G277 and Norit A Supra (both commercially available from American Norit). Finally, Porapak® RDx (Waters), a styrene vinyl pyrrolidone copolymer which has affinity for nitro aromatic compounds, was also tested.

Initially, an equilibrium adsorption study was performed with samples of each resin to evaluate capacity for 5-[(β-carboxyethyl)amino]acridine and adenine (6-aminopurine). Approximately 0.1 g of resin was weighed and transferred into a 6 mL polypropylene tube. A 5.0 mL aliquot of 25% plasma/75% Adsol® (Baxter) containing 100 µM of 5-[(β-carboxyethyl)amino]acridine in distilled water was then added to each tube. Cellular products such as red blood cells are typically stored in a medium containing a low percentage of plasma (10-35%) with a balance of synthetic media;

Adsol® is one example of a synthetic media that consists of adenine, dextrose, and mannitol in a saline solution. Of course, the present invention contemplates the use of concentrations of acridines other than 100 μM in mixtures of plasma and other synthetic media. Next, the tubes were placed on a tumbling agitator and incubated for 3 hours at room temperature.

Following incubation, aliquots of each sample were removed for analysis of residual 5-[(β-carboxyethyl)amino]acridine and adenine by HPLC.

For the HPLC procedure, each sample was diluted 2-fold with sample diluent (50% methanol, 25 mM $KH_2PO_4$, pH=3.5), and proteins and other macromolecules were precipitated by incubating the samples at 4° C. for 30 minutes. The samples were then centrifuged and the supernatant was filtered (0.2 pmeter) and analyzed on a C-18 reversed phase column (YMC ODS-AM 4.6 mm×250 mm) by running a linear gradient from 75% solvent A (25 mM $KH_2PO_4$, pH=3.5), 25% B (methanol) to 80% B in 20 minutes. For 5-[(β-carboxyethyl)amino]acridine removal, estimated capacities (μmole/g) at $C_f$=1 μM were determined from single adsorption measurements with $C_o$=100 μm; the results are set forth in the second column of Table 6 (ND=not detectable). For adenine removal, estimated capacities (mmole/g) at $C_f$=1 mM were estimated from single adsorption measurements with $C_o$=1.5 mM. The results are set forth in the third column of Table 6 (ND=not detectable).

TABLE 6

| Resin | Estimated 5-[(β-carboxyethyl)amino]acridine Capacity (μmole/g) at $C_f$ = 1 μM | Adenine Capacity (mmole/g) at $C_f$ = 1 mM |
|---|---|---|
| XAD-2 | 0.1 | 0.00 |
| XAD-4 | 3.2 | 0.02 |
| XAD-7 | 0.1 | 0.01 |
| XAD-16HP | 4.3 | 0.03 |
| XUS-43493 | 17.5 | 0.46 |
| XUS-40285 | 6.8 | 0.27 |
| MN-150 | 1.6 | 0.24 |
| MN-170 | 4.2 | 0.43 |
| MN-200 | 8.9 | 0.46 |
| MN-300 | 5.1 | 0.33 |
| MN-400 | 4.4 | 0.22 |
| MN-500 | 8.0 | 1.17 |
| MN-600 | 5.8 | 0.36 |
| IRA-958 | 0.0 | 0.00 |
| IRA-900 | 0.0 | 0.01 |
| DP-1 | 0.0 | 0.00 |
| IRA-35 | 0.0 | 0.01 |
| IRA-120 | 4.7 | 0.41 |
| Hemosorba AC | ND | ND |
| PICA G277 | 5.0 | ND |
| Norit A Supra | ND | ND |
| Porapak RDx | 0.1 | 0.01 |
| IRA-410-D | 0.0 | 0.00 |

Figure 13:
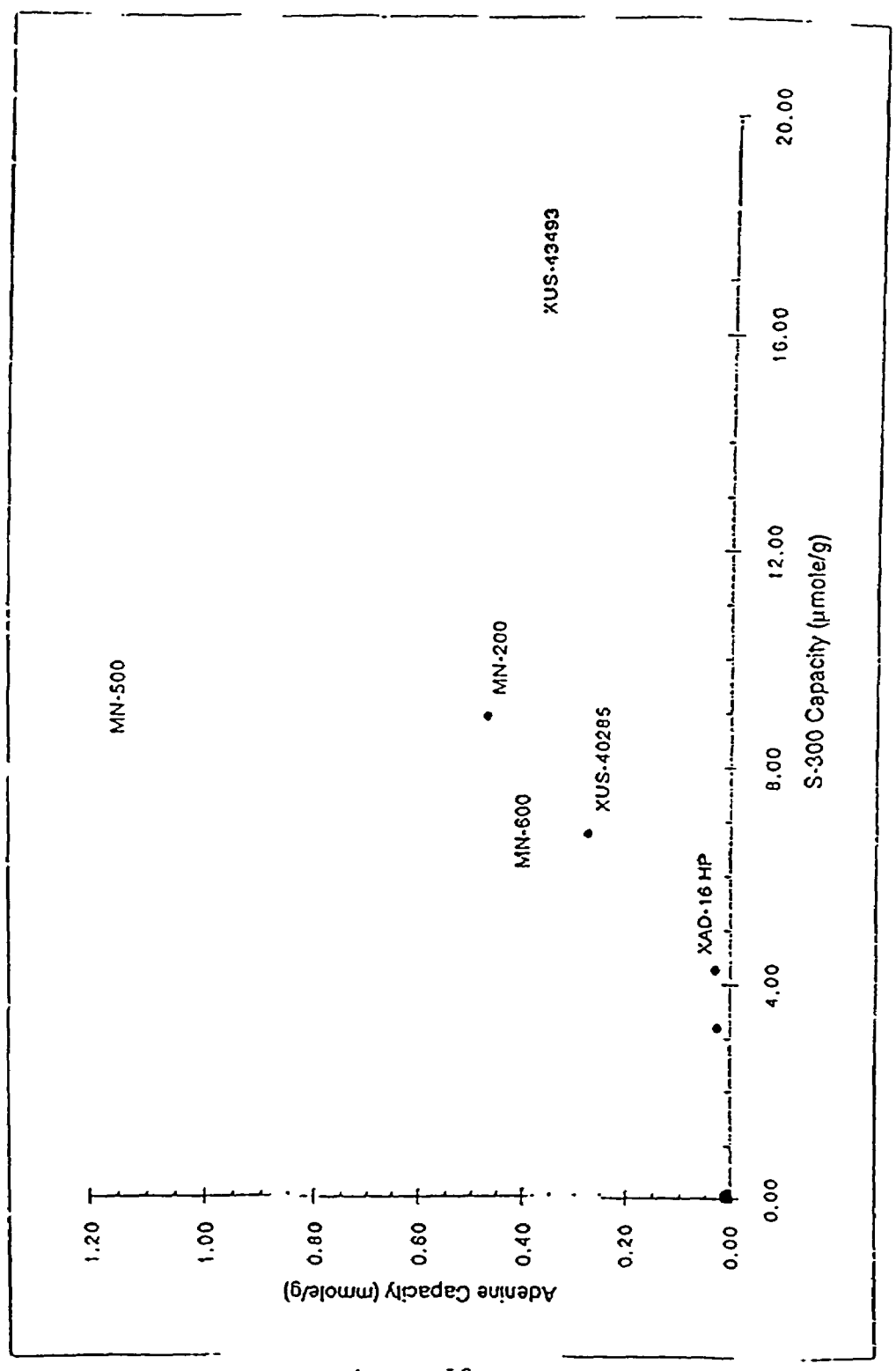
FIG. 13 is a graph showing plots the data for adenine capacity (y-axis) and 5-[(β-carboxyethyl)amino]acridine capacity (x-axis) for various resins.

While the use of any resin capable of adsorbing acridine compounds is contemplated, preferred resins selectively adsorb 5-[(β-carboxyethyl)amino]acridine over adenine and exhibit low hemolysis. FIG. 13 plots the data for adenine capacity (y-axis) and 5-[(β-carboxyethyl)amino]acridine capacity (x-axis) for various resins. As indicated by the data in Table 6 and FIG. 13, the Dowex® XUS-43493 and Purolite® MN-200 resins had the highest 5-[(β-carboxyethyl)amino]acridine capacity; moreover, when both high 5-[(β-carboxyethyl)amino]acridine capacity and low adenine capacity were considered, the Amberlite®9 XAD-16 HP performed well.

The results from the in vitro experiments described in this example suggest that Dowex® XUS-43493 and the related resin Purolite® MN-200 are preferred resins for the removal of acridine compounds from PRBCs.

Example 7

Removal of Acridine Compounds from Packed Red Blood Cells With Styrene-divinylbenzene Adsorbents This example is directed at the ability of a variety of different styrene-divinylbenzene (styrene-DVB) adsorbents to remove aminoacridine compounds from blood preparations. More specifically, the experiments of this example evaluate the removal of acridine orange and 9-amino acridine (depicted in FIG. 12) from a plasma/Adsolo solution.

A. Experimental Procedures

For the experiments of this example, stock solutions (10 mM) of 5-[(β-carboxyethyl)amino]acridine (Cerus) and acridine orange (Aldrich) were prepared in distilled water, and a stock solution (10 mM) of 9-amino acridine (Aldrich) was prepared in ethanol. The 5-[(β-carboxyethyl)amino]acridine was added to a solution containing 25% plasma/75% saline to achieve a final concentration of 100 μM, while the acridine orange and the 9-amino acridine compounds were added to solutions containing 25% plasma/75% Adsol® (Baxter) Red Cell Preservation Solution to achieve a final acridine concentration of 100 μM.

The adsorbents utilized were Amberlite® XAD-16 HP (Rohm and Haas); Purolite® MN-200, and Dowex® XUS-43493 (Supelco). The water content of each adsorbent was determined by measuring the mass loss upon drying; the water content was corrected for so that the equivalent of 0.25 g dry of each adsorbent was used. Adsorbents were accurately weighed into 50 mL Falcon tubes. Thirty (30) mL of the 25% plasma/75% Adsol® solution containing 100 μM acridine was added to each tube containing adsorbent. The tubes were then placed on a rotator at room temperature, and 500 μL samples of solution were removed at various times and stored for later analysis.

Samples were analyzed by HPLC for levels of residual acridine. Each sample was diluted 2-fold with sample diluent (50% methanol, 25 mM $KH_2PO_4$, pH=3.5), and proteins and other macromolecules were precipitated by incubating the samples at 4° C. for 30 minutes. The samples were then centrifuged and the supernatant was filtered (0.2 μmeter) and analyzed on a C-18 reversed phase column (YMC ODS-AM 4.6 mm×250 mm) by running a linear gradient from 75% solvent A (25 mM $KH_2PO_4$, pH=3.5), 25% B (methanol) to 80% B in 20 minutes. Detection was by visible absorbance using a diode array detector set at 400 nm for 9-amino acridine, 490 nm for acridine orange, and 410 nm for 5-[(β-carboxyethyl)amino]acridine.

B. Adsorption Kinetics

Figure 14A:
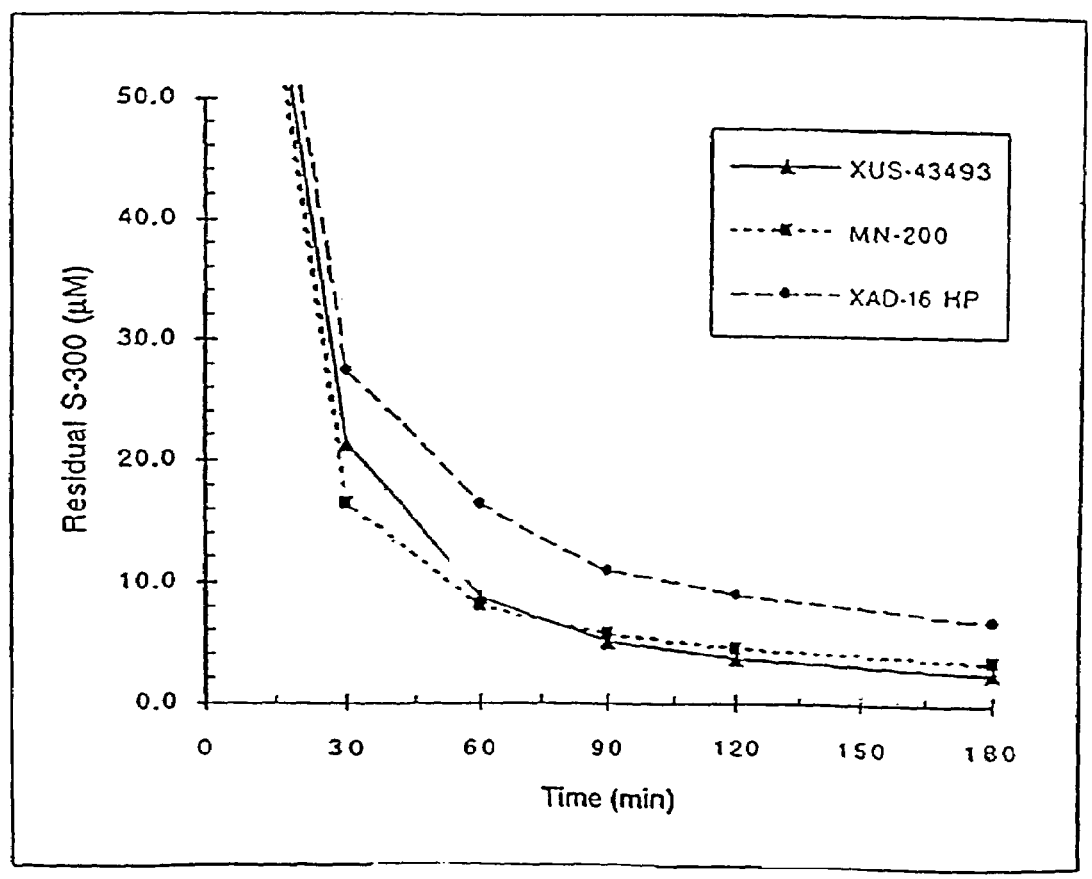
FIGS. 14A and 14B is a graph showing a comparison of the adsorption kinetics for removal of 5-[(β-carboxyethyl)amino]acridine with Dowex® XUS-43493 and Purolite® MN-200 and Amberlite® XAD-16 HP.
Figure 14B:
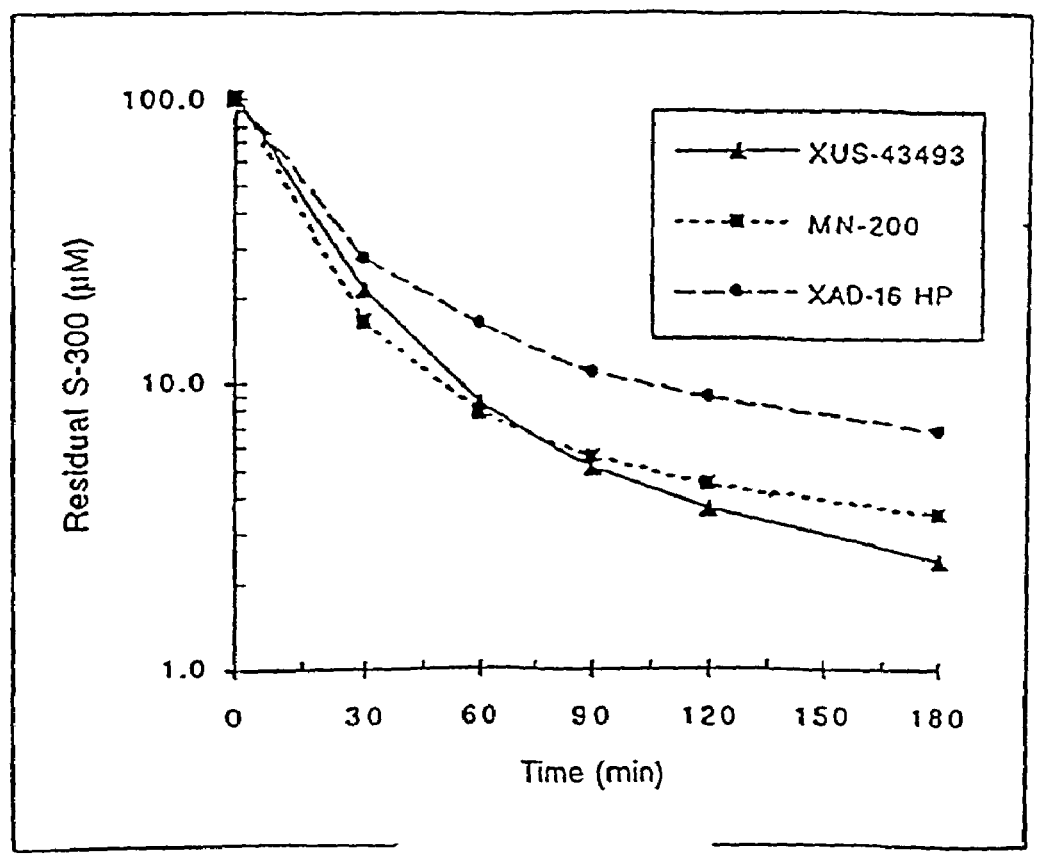

The kinetics of adsorption of 5-[(β-carboxyethyl)amino]acridine over a 3-hour period from 25% plasma/75% saline were compared for Dowex® XUS-43493, Purolite® MN-200, and Amberlite® XAD-16 HP. FIG. 14A and FIG. 14B both represent residual 5-[(β-carboxyethyl)amino]acridine as a function of time, FIG. 14B presenting the data on a logarithmic scale. In FIG. 14A and FIG. 14B, the XAD-16 HP data is represented by shaded circles connected by dashed lines, the MN-200 data is represented by shaded squares connected by dashed lines, and the XUS-43493 data is represented by shaded triangles connected by solid lines. As the data indicate, the XUS-43493 and MN-200 gave the fastest adsorption kinetics and were nearly equivalent. The XAD-16 HP appears to have a lower capacity for 5-[(β-carboxyethyl)amino]acridine.

Figure 15:
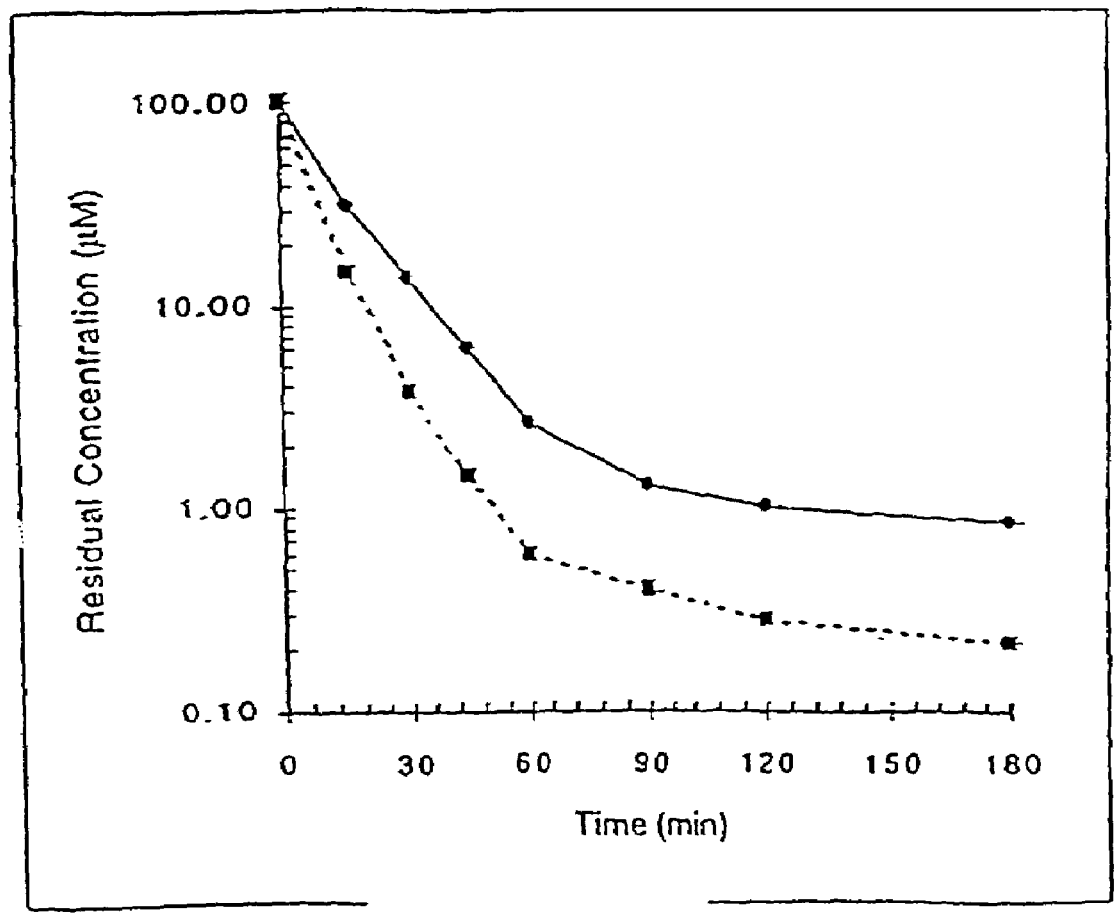
FIG. 15 is a graph showing a comparison of the adsorption kinetics for removal of 9-amino acridine and acridine orange with Dowex® XUS-43493.

FIG. 15 compares the adsorption kinetics for removal of 9-amino acridine and acridine orange from 25% plasma/75% Adsol® with Dowex® XUS-43493. Referring to FIG. 15, the shaded squares with the dashed lines represent 9-amino acridine, and the shaded circles with the solid lines represent acridine orange. As the data indicate, levels of 9-amino acridine were undetectable beyond 3 hours. By comparison, the capacity of the Dowex® XUS-43493 for acridine orange was lower, which may be related to the presence of two tertiary amino groups on acridine orange.

Example 8

Preparation of PRBCs Treated With a 5-[(β-carboxyethyl)amino]acridine derivative and Glutathione. Pools of PRBC were prepared from fresh ABO-matched whole blood. The units of whole blood were centrifuged at 3800 rpm for 5 minutes using a Beckman Sorvall RC3B centrifuge. The plasma was expressed into another clean bag using an expresser. The units of PRBC were pooled into a 3.0 L size Clintec Viaflex bag if more than one unit was needed. For each unit of PRBC, 94 mL of Erythrosol was added. The percentage of Hematocrit (HCT) was measured by filling a capillary tubing with the blood sample and spinning it for 5 minutes. The hematocrit was determined to ensure that it did not decrease below 55%. For each 100 mL of PRBC, 3.3,mL of 12% glucose was added. The final percentage hematocrit was determined. PRBC (300 mL) was refilled into plastic containers PL146 (Baxter Healthcare). To the blood bags was added 6.0 mL of 150 mM glutathione to reach a 3.0 mM final concentration and 3.0 mL of 30 mM a 5-[(β-carboxyethyl)amino]acridine derivative for a final concentration of 300 μM. The PRBC mixture was agitated for 1 minute using a wrist action shaker (manufacturer). The 5-[(β-carboxyethyl)amino]acridine derivative and glutathione treated PRBCs were allowed to incubate at room temperature overnight to allow break down of the 5-[(β-carboxyethyl)amino]acridine derivative into 5-[(β-carboxyethyl)amino]acridine.

Example 9

HPLC Assay for 5-[(β-carboxyethyl)amino]acridine in PRBC and PRBC Supernatant. The sample (100 μL) was diluted with 100 μL of saline and the resulting mixture was vortexed. To the solution was added 300 μL of 20 mM $H_3PO_4$ in CH3CN, and the mixture was vortexed for 15 sec. The sample was centrifuged at 13,200 rpm for 5 minutes. The supernatant (200 μL) was diluted into 800 μL of cold 0.1 M HCl and vortexed. The sample was filtered into an autosampler vial using a 0.2 μm Gelman Acrodisc filter. The HPLC conditions were as follows: (Manufacturer and part no. for column and general column.) Column=Zorbax SB-CN, 4.6 mm×150 mm, 3.5 μm particles; guard column=(4.6 mm×12.5 mm, 5 μm particles (Mac Mod Analytical, Inc. (Chadds Ford, Pa.)); the mobile phase for A was 10 mM $H_3PO_4$ in HPLC water; the mobile phase for C was 10 mM $H_3PO_4$ in acetonitrile; temperature was 20° C.; sample volume was 100 μL; gradient conditions were as follows:

| Time | A (%) | C (%) | Flow Rate (mL/min) |
|---|---|---|---|
| 0.00 | 90.0 | 10.0 | 1.0 |
| 5.28 | 77.0 | 23.0 | 1.0 |
| 10.00 | 40.0 | 60.0 | 1.0 |
| 11.00 | 90.0 | 10.0 | 1.0 |
| 16.00 | STOP | STOP | STOP | the DAD settings were as follows:

| Signal | Detection Wavelength | Detection Bandwidth | Reference Wavelength | Reference Bandwidth |
|---|---|---|---|---|
| A | 410 | 5 | 580 | 20 |
| B | 260 | 5 | 580 | 20 |

Example 10

HPLC Assay for Glutathione in PRBC and PRBC Supernatant. The sample was prepared as for the HPLC assay described above. The HPLC conditions were as follows: analytical column=YMC ODS-AM-303, 250 mm×4.6 mm, 5 μm particle; guard column=Brownlee, 15×3.2 mm, 7 μm particle; the mobile phase for A was 10 mM $H_3PO_4$ in HPLC water; the mobile phase for C was 10 mM $H_3PO_4$ in acetonitrile; the temperature was 15° C.; the sample volume was 75 μL; the gradient conditions were as follows:

| Time | A (%) | C (%) | Flow Rate (mL/min) |
|---|---|---|---|
| 0.00 | 95.0 | 5.0 | 0.5 |
| 6.00 | 95.0 | 5.0 | 0.5 |
| 8.00 | 10.0 | 90.0 | 1.0 |
| 9.00 | 95.0 | 5.0 | 1.0 |
| 20.00 | STOP | STOP | STOP | the DAD settings were as follows:

| Signal | Detection Wavelength | Detection Bandwidth | Reference Wavelength | Reference Bandwidth |
|---|---|---|---|---|
| A | 205 | 10 | 600 | 100 |

Example 11

Method of Screening Adsorbents. A test solution containing 25% plasma and 75% Erythrosol was used to represent the supernatant from PRBCs. Erythrosol was prepared as two separate stock solution parts (solution C and solution D) that were sterilized separately. The final solutions were prepared by mixing equal volumes of solution C and solution D.

| Solution C | Solution D |
|---|---|
| 3.2 mM Adenine | 53.2 mM Na citrate $2H_2O$ |
| 85 mM mannitol | 5.4 mM $NaH_2PO_4 2H_2O$ |

-continued

| Solution C | Solution D |
|---|---|
| 100 mM glucose 6.2 mM HCl | 38 mM $Na_2HPO_4 2H_2O$ |

The plasma-Erythrosol solution was spiked with 5-[(β-carboxyethyl)amino]acridine to a final concentration of 300 μM. Glutathione (reduced form, Sigma Chemical Co.) was added to the mixture to obtain a final concentration of 3 mM. Samples of adsorbents (0.2-0.8 g) were accurately weighed (±0.001 g) into tared 7 mL polypropylene vials with screw tops. Samples of adsorbent that required pre-wetting were suspended in 70% ethanol. The adsorbent was allowed to settle and the supernatant was removed. Residual ethanol was removed by resuspending the adsorbent in distilled water, allowing the adsorbent to settle, and decanting the supernatant. Adsorbent masses were corrected for water content when adsorption capacities were calculated. A 5.0 mL aliquot of plasma/Erythrosol was added to each tube. The tubes were placed on a rotator and tumbled at room temperature for 24 hours. The vials were removed from the rotator and the adsorbent was allowed to settle. A sample of the supernatant was removed from each tube. Samples were centrifuged to remove residual adsorbent. Samples were analyzed by HPLC to determine residual levels of 5-[(β-carboxyethyl)-amino] acridine. The reversed phase assay described above was used to determine residual levels of glutathione. The results from the adsorbent screen are shown in Tables 7 and 8.

TABLE 7

Adsorbent Screen - Removal of 5-[(β-carboxyethyl)amino]acridine from 25% Plasma/75% Erythrosol. ("LOD" is limit of detection.)

| Adsorbent | Chemistry | Corrected Mass (g) | Wetting Required? | Final Acridine C, (μM) | Capacity (μmole/g) | Estimated K (L/g) |
|---|---|---|---|---|---|---|
| Purolite MN-150 | Weak base, PS-DVB | 0.108 | No | 1.4 | 13.5 | 9.7 |
| Purolite MN-170 | Weak base, PS-DVB | 0.105 | No | 0.4 | 14.0 | 38.4 |
| Purolite MN-200 | Nonfunctional, PS-DVB | 0.077 | No | 0.9 | 19.1 | 21.5 |
| Purolite MN-300 | Weak Base, PS-DVB | 0.111 | No | 1.0 | 13.2 | 13.4 |
| Purolite MN-400 | Strong base, PS-DVB | 0.102 | No | 1.1 | 14.3 | 13.0 |
| Purolite MN-500 | Strong acid, PS-DVB | 0.098 | No | 0.6 | 15.0 | 24.2 |
| Purolite MN-600 | Weak acid, PS-DVB | 0.112 | No | 0.8 | 13.1 | 16.7 |
| Dowex Optipore L-493 | Nonfunctional PS-DVB 46 A, 1100 $m^2/g$ | 0.189 | No | 0.3 | 7.8 | 22.5 |
| Dowex Optipore L-285 | Weak base, PS-DVB 25 A, 800 $m^2/g$ | 0.245 | No | 0.5 | 6.0 | 11.2 |
| Amberlite XAD-2 | Nonfunctional PS-DVB 90 A, 300 $m^2/g$ | 0.190 | Yes | 117.5 | 4.7 | 0.0 |
| Amberlite XAD-4 | Nonfunctional PS-DVB 40 A, 725 $m^2/g$ | 0.118 | Yes | 1.6 | 12.4 | 7.7 |
| Amberlite XAD-7 | Polyacrylic ester 90 A, 450 $m^2/g$ | 0.097 | Yes | 117.4 | 9.1 | 0.1 |
| Amberlite XAD-16 | Nonfunct. polystyrene 100 A, 800 $m^2/g$ | 0.101 | Yes | 44.1 | 12.4 | 0.3 |
| Hemosorba AC | Activated charcoal pHEMA-coated | 0.149 | No | LOD | >9.8 | >196.8 |
| Duolite GT-73 | Thiol-containing macroreticular | 0.144 | No | 1.0 | 10.2 | 10.2 |
| Kieselguhr | Diatomaceous earth | 0.131 | No | 317.7 | −0.9 | 0.0 |
| Graver GL-711 | Ground XUS-43493 attached to fiber | 0.134 | No | 1.9 | 10.9 | 5.8 |
| Amberlite IRA 900 | Quat. Am. macroreticular PS, Cl-form | 0.067 | No | 239.1 | 4.1 | 0.0 |
| Amberlite IRA 35 | Weak base modified PS | 0.076 | No | 223.7 | 4.6 | 0.0 |
| Amberlite IRA 410 D | Strong base gel PS Cl-form | 0.086 | No | 127.2 | 9.7 | 0.1 |

TABLE 7-continued

Adsorbent Screen - Removal of 5-[(β-carboxyethyl)amino]acridine from 25% Plasma/75% Erythrosol. ("LOD" is limit of detection.)

| Adsorbent | Chemistry | Corrected Mass (g) | Wetting Required? | Final Acridine C, (μM) | Capacity (μmole/g) | Estimated K (L/g) |
|---|---|---|---|---|---|---|
| Amberlite IRA 958 | Quat. Am. macroreticular Polystyrene, Cl-form | 0.084 | No | 304.9 | −0.6 | 0.0 |
| Amberlite DP-1 | Carboxylic macroreticular PS | 0.066 | No | 292.8 | 0.1 | 0.0 |
| Amberlite IR-120 | Sulfonic acid gel PS H-form | 0.079 | No | 1.4 | 18.6 | 13.1 |
| Diaion HPA 75 | Quat. alkyl amine highly porous PS | 0.091 | No | 97.2 | 10.8 | 0.1 |
| Duolite S-761 | Phenol-formaldehyde modified PS | 0.093 | No | 1.8 | 15.8 | 8.6 |
| Duolite A-7 | Polyamine macroreticular PS, free base | 0.079 | No | 189.0 | 6.6 | 0.0 |
| Amberlite IRA-68 | Polyamine gel PS | 0.083 | No | 203.4 | 5.5 | 0.0 |
| Amberlite IRA-458 | Quat. Am. gel PS, Cl-form | 0.148 | No | 292.8 | 0.0 | 0.0 |
| Amberlite IRA-958 | Quat. Am. macroreticular PS, Cl-form | 0.139 | No | 296.3 | −0.1 | 0.0 |
| Ambersorb 563 | Synthetic AC, 550 m$^2$/g, high hydrophobicity | 0.228 | No | 0.4 | 6.4 | 17.5 |
| Ambersorb 572 | Synthetic AC, 1100 m$^2$/g, low hydrophobicity | 0.267 | No | LOD | >5.5 | >55.0 |
| Ambersorb 575 | Synthetic AC, 800 m$^2$/g, mid hydrophobicity | 0.258 | No | LOD | >5.7 | >56.9 |
| PICA G277 AC | Activated charcoal | 0.283 | No | LOD | >5.2 | >51.9 |
| PICA NC506 AC | Activated charcoal | 0.266 | No | LOD | >5.5 | >55.3 |
| PICAtif Med. AC | Activated charcoal | 0.280 | No | LOD | >5.3 | >52.5 |
| West VACO CX-S | Activated charcoal | 0.228 | No | LOD | >6.4 | >64.4 |
| Norit ASupra | Activated charcoal | 0.268 | No | LOD | >5.5 | >54.8 |
| Norti B Supra | Activated charcoal | 0.258 | No | LOD | >5.7 | >56.9 |
| Norit Supra E | Activated charcoal | 0.266 | No | LOD | >5.5 | >55.2 |
| Norit S51 AC | Activated charcoal | 0.237 | No | LOD | >6.2 | >61.9 |
| Norit SX Ultra | Activated charcoal | 0.203 | No | LOD | >7.2 | >72.2 |
| Chemviron | Activated charcoal | 0.233 | No | LOD | >6.3 | >63.1 |
| Norit CN1 | Activated charcoal | 0.261 | No | LOD | >5.6 | >56.4 |
| Norit G60 | Activated charcoal | 0.230 | No | LOD | >6.4 | >64.0 |
| Norit ROX, O, 8 | Activated charcoal | 0.246 | No | LOD | >6.0 | >59.8 |
| Norti Darco (20 × 50) | Activated charcoal | 0.219 | No | LOD | >6.7 | >67.3 |
| PICAtif Medicinal | Activated charcoal | 0.129 | No | LOD | >11.4 | >113.8 |
| Davison Silica Grade 15 | Unmodified silica | 0.245 | No | 77.0 | 4.4 | 0.1 |
| Davison Silica Grade 636 | Unmodified silica | 0.255 | No | 140.1 | 3.0 | 0.0 |
| BioRad AG501-X8(D) | Mixed bed ion exchange | 0.083 | No | 119.4 | 10.5 | 0.1 |
| Amberlite 200 | Sulfonic acid macroret. PS, Na-form | 0.080 | No | 46.5 | 15.5 | 0.3 |
| MP-3 (C-18) SPE media | Sulfonated C-18 resin | 0.239 | Yes | 1.7 | 6.1 | 3.7 |
| Alltech C-18 SPE | C-18 modified silica | 0.234 | Yes | 64.4 | 4.9 | 0.1 |
| BioRad t-Butyl HIC | C-4 modified polymethacrylate | 0.213 | Yes | 163.9 | 3.1 | 0.0 |
| Baker C-18 SPE | C-18 modified silica | 0.263 | Yes | 94.9 | 3.8 | 0.0 |
| Waters Sep Pak C-18 | C-18 modified silica | 0.190 | Yes | 81.3 | 5.6 | 0.1 |
| Baker C-4 SPE | C-4 modified silica | 0.232 | Yes | 178.3 | 2.5 | 0.0 |
| Waters Bondapak C-8 | C-8 modified silica | 0.213 | Yes | 156.9 | 3.2 | 0.0 |
| Waters Bondapak | C-4 modified | 0.228 | Yes | 251.0 | 0.9 | 0.0 |

TABLE 7-continued

Adsorbent Screen - Removal of 5-[(β-carboxyethyl)amino]acridine from 25% Plasma/75% Erythrosol. ("LOD" is limit of detection.)

| Adsorbent | Chemistry | Corrected Mass (g) | Wetting Required? | Final Acridine C, (μM) | Capacity (μmole/g) | Estimated K (L/g) |
|---|---|---|---|---|---|---|
| C-4 | silica | | | | | |
| Amberchrom cg-161 xcd | Polystyrene 150 A, 900 m$^2$/g | 0.192 | Yes | 79.3 | 5.6 | 0.1 |
| Amberchrom cg-1000 sd | Polystyrene 1000 A, 250 m$^2$/g | 0.176 | Yes | 243.7 | 1.4 | 0.0 |
| Amberchrom cg-300 md | Polystyrene 300 A, 700 m$^2$/g | 0.135 | Yes | 172.1 | 4.5 | 0.0 |
| Amberchrom cg-71 md | Polymethacrylate 250 A, 500 m$^2$/g | 0.189 | Yes | 156.4 | 3.6 | 0.0 |
| Waters Porapak RDx | PS-vinyl pyrrolidone porous adsorbent | 0.125 | Yes | 307.8 | −0.6 | 0.0 |
| CUNO Delipid Media | Resin-modified cellulose | 0.663 | No | 245.8 | 0.4 | 0.0 |
| CUNO DEAE media | Weak base modified cellulose | 0.361 | No | 280.8 | 0.2 | 0.0 |
| Sigma DE | Diatomaceous earth | 0.179 | No | 317.6 | −0.7 | 0.0 |
| Diaion SP-850 | Polystyrene 38 A, 1000 m$^2$/g | 0.236 | Yes | 1.4 | 6.2 | 4.4 |
| Diaion SP-207 | Brominated PS 105 A, 650 m$^2$/g | 0.191 | No | 211.1 | 2.2 | 0.0 |
| Diaion HP-2MG | Polymethacrylate 170 A, 500 m$^2$/g | 0.258 | Yes | 182.6 | 2.2 | 0.0 |
| Diaion HP-20 | Polystyrene 260 A, 500 m$^2$/g | 0.175 | Yes | 107.4 | 5.3 | 0.0 |
| Amberlite 1180 | Polystyrene-DVB 300 A, 600 m$^2$/g | 0.094 | Yes | 9.9 | 15.1 | 1.5 |
| Amberlite 1600 | Polystyrene-DVB | 0.208 | Yes | 73.0 | 5.3 | 0.1 |
| Amberlite XAD-2000 | Polystyrene-DVB 42 A, 580 m$^2$/g | 0.172 | Yes | 61.0 | 6.8 | 0.1 |
| Amberlite XAD-2010 | Polystyrene-DVB 280 A, 660 m$^2$/g | 0.203 | Yes | 173.0 | 3.0 | 0.0 |
| Dowex XUS-40323 | Polystyrene-DVB 100 A, 650 m$^2$/g | 0.213 | Yes | 102.6 | 4.5 | 0.0 |
| Whatman DE-52 | Weak base modified cellulose | 0.284 | No | 177.5 | 2.0 | 0.0 |
| Whatman CM-32 | Weak acid modified cellulose | 0.294 | No | 268.7 | 0.4 | 0.0 |
| Whatman QA-52 | Strong base modified cellulose | 0.264 | No | 285.2 | 0.2 | 0.0 |
| Whatman SE-53 | Strong acid modified cellulose | 0.238 | No | 294.3 | 0.0 | 0.0 |
| Pharmacia Q Seph FF | Strong base modified agarose | 0.111 | No | 267.8 | 1.2 | 0.0 |
| Pharmacia S Seph FF | Strong acid modified agarose | 0.112 | No | 267.0 | 1.2 | 0.0 |
| Toyopearl QAE-550 C | Wead base modified agarose | 0.118 | No | 266.8 | 1.2 | 0.0 |
| Toyopearl Butyl 650-M | Hydrophobic (C-4) modified methacrylate | 0.112 | Yes | 232.8 | 2.7 | 0.0 |
| Toyopearl SP-550C | Strong acid modified methacrylate | 0.111 | No | 230.2 | 2.9 | 0.0 |
| Toyopearl CM-650M | Weak acid modified methacrylate | 0.118 | No | 249.0 | 1.9 | 0.0 |
| Toyopearl DEAE-650M | Weak base modified methacrylate | 0.112 | No | 260.4 | 1.5 | 0.0 |
| Toyopearl Super Q 650C | Strong base modified methacrylate | 0.111 | No | 263.2 | 1.4 | 0.0 |

TABLE 8

Adsorbent Screen - Removal of Glutathione from 25% Plasma/75% Erythrosol

| Absorbent | GSH HPLC Area (mAU * sec) | Final GSH Conc. (μM) | Estimated Capacity at $C_f$ (μmole/g) | Estimated Capacity at $C_f$ = 30 μM (μmole/g) |
|---|---|---|---|---|
| Purolite MN-150 | 336.1 | 2375 | 28.9 | 0.4 |
| Purolite MN-170 | 386.7 | 2732 | 12.8 | 0.1 |
| Purolite MN-200 | 445.5 | 3147 | −9.6 | −0.1 |
| Purolite MN-300 | 356.7 | 2520 | 21.7 | 0.3 |
| Purolite MN-400 | 297.0 | 2099 | 44.1 | 0.6 |
| Purolite MN-500 | 392.8 | 2775 | 11.5 | 0.1 |
| Purolite MN-600 | 392.4 | 2773 | 10.1 | 0.1 |
| Dowex XUS-43493 | 428.5 | 3027 | −0.7 | 0.0 |
| Dowex XUS-40285 | 251.6 | 1778 | 24.9 | 0.4 |
| Amberlite XAD-2 | 420.8 | 2973 | 0.7 | 0.0 |
| Amberlite XAD-4 | 449.0 | 3172 | −7.3 | −0.1 |
| Amberlite XAD-7 | 448.0 | 3165 | −8.5 | −0.1 |
| Amberlite XAD-16 | 412.2 | 2912 | 4.4 | 0.0 |
| Hemosorba AC | 7.9 | 56 | 98.6 | 53.3 |
| Duolite GT-73 | 379.3 | 2680 | 11.2 | 0.1 |
| Kieselguhr | 471.3 | 3330 | −12.6 | −0.1 |
| Graver GL-711 | 466.2 | 3294 | −11.0 | −0.1 |
| Amberlite IRA 900 | 441.1 | 3116 | −8.6 | −0.1 |
| Amberlite IRA 35 | 434.4 | 3069 | −4.5 | 0.0 |
| Amberlite IRA 410 D | 413.0 | 2918 | 4.8 | 0.0 |
| Amberlite IRA 958 | 446.2 | 3152 | −9.1 | −0.1 |
| Amberlite DP-1 | 433.3 | 3061 | −4.6 | 0.0 |
| Amberlite IRA-120 | 388.6 | 2745 | 16.2 | 0.2 |
| Diaion HPA 75 | 447.3 | 3160 | −8.8 | −0.1 |
| Duolite S-761 | 312.9 | 2211 | 42.6 | 0.6 |
| MP-3 | 428.0 | 3024 | −0.5 | 0.0 |
| Alltech C-18 SPE | 411.3 | 2906 | 2.0 | 0.0 |
| Duolite A-7 | 444.2 | 3138 | −8.7 | −0.1 |
| Amb IRA-68 | 443.5 | 3133 | −8.1 | −0.1 |
| Amb IRA-458 | 460.6 | 3254 | −8.6 | −0.1 |
| Amb IRA-958 | 426.3 | 3012 | −0.4 | 0.0 |
| Ambersorb 563 | 435.2 | 3075 | −1.6 | 0.0 |
| Ambersorb 572 | 0.0 | LOD | >56.1 | >167.9 |
| Ambersorb 575 | 0.0 | LOD | >58.1 | >173.8 |
| PICA G277 AC | 0.0 | LOD | >53.0 | >158.4 |
| PICA NC506 AC | 0.0 | LOD | >56.4 | >168.7 |
| PICAtif Med. AC | 0.0 | LOD | >53.6 | >160.4 |
| West VACO CX-S | 0.0 | LOD | >65.7 | >196.5 |
| Norit A Supra | 0.0 | LOD | >55.9 | >167.2 |
| Norti B Supra | 0.0 | LOD | >58.1 | >173.7 |
| Norit Supra E | 0.0 | LOD | >56.3 | >168.5 |
| Norit S51 AC | 0.0 | LOD | >63.2 | >189.0 |
| Norit SX Ultra | 0.0 | LOD | >73.7 | >220.5 |
| Chemviron | 0.0 | LOD | >64.4 | >192.6 |
| Norit CN1 | 0.0 | LOD | >57.5 | >172.1 |
| Norit G60 | 0.0 | LOD | >65.3 | >195.4 |
| Norit ROX, O, 8 | 0.0 | LOD | >61.0 | >182.4 |
| Norti Darco (20 × 50) | 0.0 | LOD | >68.6 | >205.3 |
| PICAtif Medicinal | 0.0 | LOD | >116.2 | >347.4 |
| Whatman 150A Silica | 448.8 | 3171 | −3.6 | 0.0 |
| Davison Silica Grade 15 | 443.5 | 3133 | −2.7 | 0.0 |
| Davison Silica Grade 636 | 423.9 | 2995 | 0.1 | 0.0 |
| BioRad AG501-X8(D) | 445.6 | 3148 | −8.9 | −0.1 |
| Amberlite 200 | 458.1 | 3237 | −14.8 | −0.1 |
| BioRad t-Butyl HIC | 484.0 | 3419 | −9.8 | −0.1 |
| Baker C-18 SPE | 427.7 | 3022 | −0.4 | 0.0 |
| Waters Sep Pak C-18 | 422.2 | 2983 | 0.4 | 0.0 |
| Baker C-4 SPE | 429.8 | 3036 | −0.8 | 0.0 |
| Waters Bondapak C-8 | 405.5 | 2865 | 3.2 | 0.0 |
| Waters Bondapak C-4 | 390.8 | 2761 | 5.2 | 0.1 |
| Amberchrom cg-161 xcd | 414.8 | 2931 | 1.8 | 0.0 |
| Amberchrom cg-1000 sd | 373.5 | 2639 | 10.2 | 0.1 |
| Amberchrom cg-300 md | 396.2 | 2799 | 7.4 | 0.1 |
| Amberchrom cg-71 md | 396.4 | 2800 | 5.3 | 0.1 |
| Waters Porapak RDx | 449.9 | 3179 | −7.1 | −0.1 |
| CUNO Delipid Media | 452.5 | 3197 | −1.5 | 0.0 |
| CUNO DEAE media | 213.7 | 1510 | 20.6 | 0.4 |

TABLE 8-continued

Adsorbent Screen - Removal of Glutathione from 25% Plasma/75% Erythrosol

| Absorbent | GSH HPLC Area (mAU * sec) | Final GSH Conc. (µM) | Estimated Capacity at $C_f$ (µmole/g) | Estimated Capacity at $C_f$ = 30 µM (µmole/g) |
|---|---|---|---|---|
| Sigma Diatomaceous Earth | 473.9 | 3348 | −9.7 | −0.1 |
| Diaion SP-850 | 424.1 | 2996 | 0.1 | 0.0 |
| Diaion SP-207 | 471.6 | 3332 | −8.7 | −0.1 |
| Diaion HP-2MG | 429.7 | 3036 | −0.7 | 0.0 |
| Diaion HP-20 | 422.3 | 2984 | 0.5 | 0.0 |
| Amb 1180 | 441.7 | 3120 | −6.4 | −0.1 |
| Amberilte 1600 | 426.6 | 3014 | −0.3 | 0.0 |
| Amberlite XAD-2000 | 407.4 | 2879 | 3.5 | 0.0 |
| Amberlite XAD-2010 | 423.0 | 2988 | 0.3 | 0.0 |
| Dowex XUS-40323 | 372.7 | 2633 | 8.6 | 0.1 |
| Whatman DE-52 | 384.7 | 2718 | 5.0 | 0.1 |
| Whatman CM-32 | 514.8 | 3637 | −10.8 | −0.1 |
| Whatman QA-52 | 398.1 | 2813 | 3.5 | 0.0 |
| Whatman SE-53 | 458.0 | 3236 | −4.9 | 0.0 |
| Pharmacia Q Seph FF | 377.6 | 2668 | 15.0 | 0.2 |
| Pharmacia S Seph FF | 390.5 | 2759 | 10.8 | 0.1 |
| Toyopearl QAE-550 C | 395.1 | 2792 | 8.8 | 0.1 |
| Toyopearl Butyl 650-M | 372.9 | 2635 | 16.2 | 0.2 |
| Toyopearl SP-550C | 404.2 | 2856 | 6.5 | 0.1 |
| Toyopearl CM-650M | 394.0 | 2784 | 9.2 | 0.1 |
| Toyopearl DEAE-650M | 392.3 | 2772 | 10.2 | 0.1 |
| Toyopearl Super Q 650C | 384.6 | 2717 | 12.8 | 0.1 |

Example 12

Figure 17:
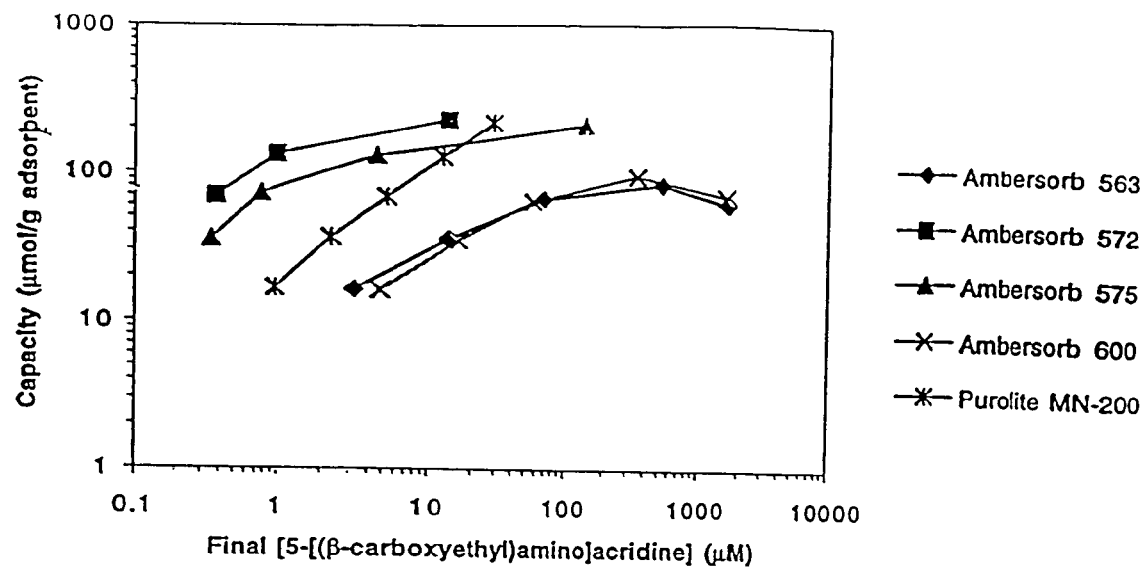
FIG. 17 is a graph showing a comparison of the adsorption isotherms for various Ambersorbs as compared to Purolite MN-200.

Adsorption Capacities for Adsorbents. Adsorption isotherm experiments were carried out to determine the adsorptive capacities (µmole 5-[(β-carboxyethyl)-amino]acridine/g adsorbent) for various types of adsorbents. FIG. 17 shows adsorption isotherms obtained for several Ambersorbs as compared to the adsorption isotherm for Purolite MN-200. Adsorption studies were performed in 25% plasma/75% Erythrosol solutions containing 0.2-3 mM 5-[(β-carboxyethyl)amino]acridine and 0.6-10 mM GSH. Samples were agitated for 24 hours at room temperature. Calculations using the adsorption capacity from Table 7 (22µ mole/g) determined that approximately 4 g of Purolite MN-200 would be required to reduce the level of 5-[(β-carboxyethyl)-amino] acridine in a 300 mL unit of PRBC from 300 µM to a final level of 1 µM. Less than 1 g of Ambersorb 572 (130 µmole/g) would be required to achieve comparable removal. A similar calculation estimated that less than 1 g of Ambersorb 572 would be required to reduce the level of GSH in a 300 µL unit of PRBC from 6 mM to a final level of 500 µM in the 150 µL of supernatant (50% HCT).

Example 13

Long Tern Removal of Breakdown Products.

This experiment examined 5-[(β-carboxyethyl)-amino] acridine and GSH levels in PRBCs from which a fiberized PICA G-277 activated carbon device (AQF, 7.3g, 500 m²/g) was removed after 24 hours of exposure. This study was conducted in parallel with studies where the PRBCs had continued device exposure. FIG. 18 shows that the concentrations of 5-[(β-carboxyethyl)-amino]acridine and GSH in the supernatant samples were considerably higher in the absence of a device over storage times of 1 to 4 weeks.

The concentration of 5-[(β-carboxyethyl)-amino]acridine was reduced to 5 µM in initially shaken PRBCs after 35 days of storage in the presence of a removal device (MN-200). This indicates that 5-[(β-carboxyethyl)-amino]acridine removal does occur in static storage conditions at 4° C.

Example 14

Effect of Enclosure Material (Membrane, Woven, Nonwoven) on an IAD

Figure 19:
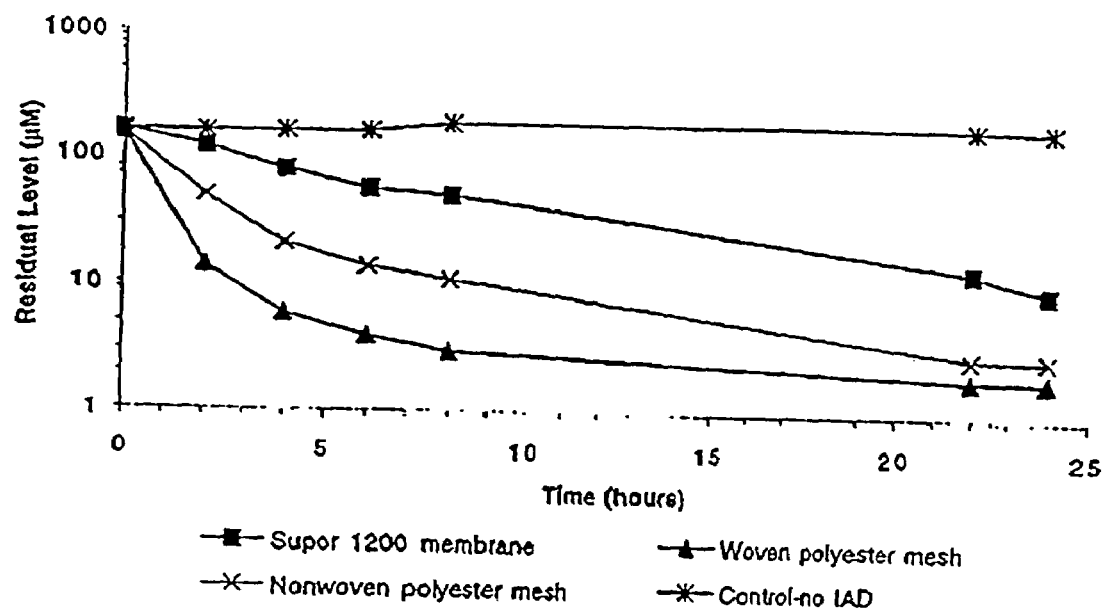
FIG. 19 is a graph showing the effect of enclosure material on adsorption kinetics for 5-[(β-carboxyethyl)amino]acridine in PRBCs.

The use of an enclosure material surrounding the adsorbent media was investigated for the primary purpose of particle retention. The primary purpose is particle retention. However, membranes can enhance hemocompatibility of the devices by preventing contact between the RBCs and membranes. Membranes can easily be modified with hydrophilic polymers (PEO, PEG, HPL) to enhance hemocompatibility without altering function. Approximately 10 g of fiberized Pica G277 activated carbon media (AQF 500 g/m²) was surrounded by a heat-sealed membrane, woven polyester, or non-woven polyester material. PRBC units (300 mL) were dosed with 300 µM of a degradable 5-[(β-carboxyethyl)amino]acridine derivative and 3 mM GSH, held at room temperature for 20 hours on a platelet shaker, and then transferred to IADs. Concentration of 5-[(β-carboxyethyl)-amino]acridine was monitored over 24 hours. FIG. 19 shows 5-[(β-carboxyethyl)-amino]acridine levels in the supernatant of 300 mL PRBC units exposed to LADs consisting of fiberized Pica G277 activated carbon (500 g/m²) and enclosed by a membrane, woven, or non-woven material. PRBCs (Erythrosol, glucose, 62% HCT) were dosed with 300 µM of a degradable 5-[(β-carboxyethyl) amino]acridine derivative and 3 mM GSH, and agitated on a platelet shaker at room temperature prior to transfer to the IADs. PRBC-containing LADs were agitated at room temperature for 24 hours.

These studies indicate that the Tetko woven enclosure shows the fastest removal kinetics for 5-[(β-carboxyethyl)-amino]acridine over 24 hours. Final levels achieved for all enclosure materials after 2 weeks were similar, with 5-[(β- carboxyethyl)-amino]acridine concentrations decreasing to approximately 2 μM after 1 day, but rising back to 10 μM near day 8.

Example 15

Effect of the Compound Adsorption Device on Red Blood Cell Function.

Figure 20:
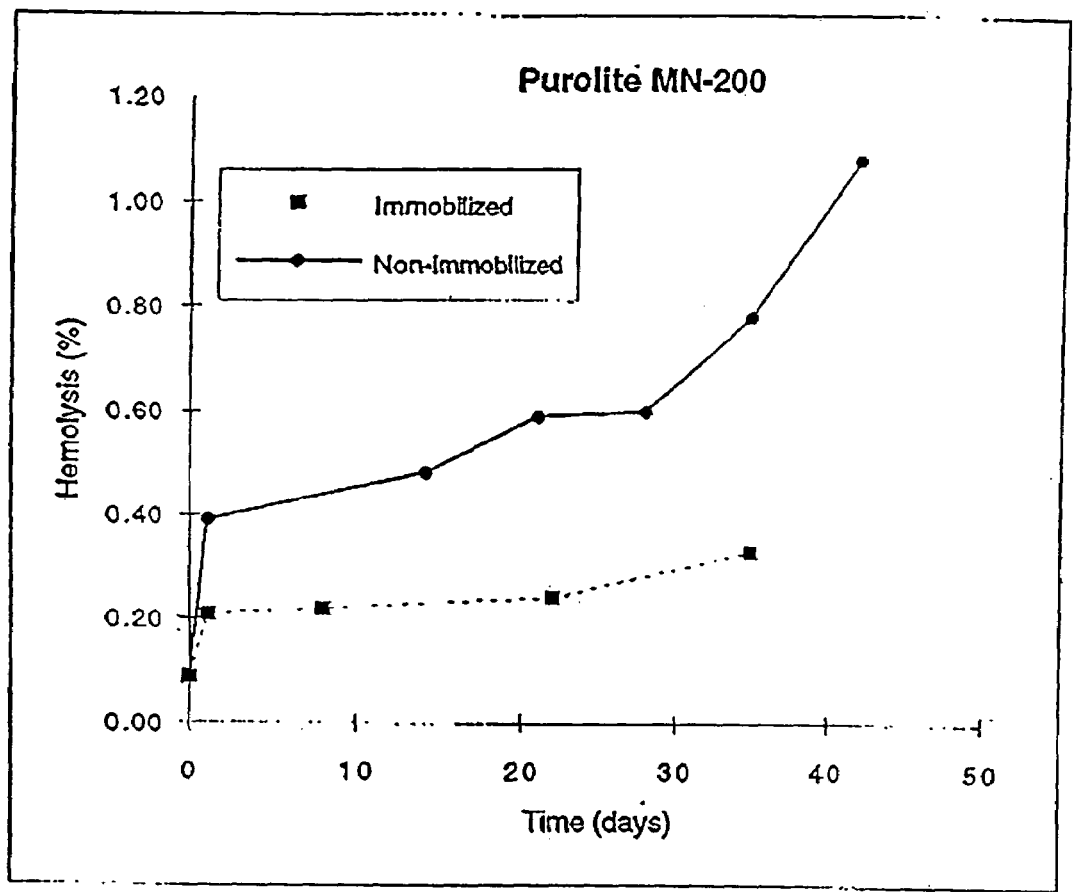
FIG. 20 is a graph showing a comparison of percent hemolysis for the adsorbent devices containing non-immobilized and immobilized adsorbent particle Purolite MN-200.
Figure 21:
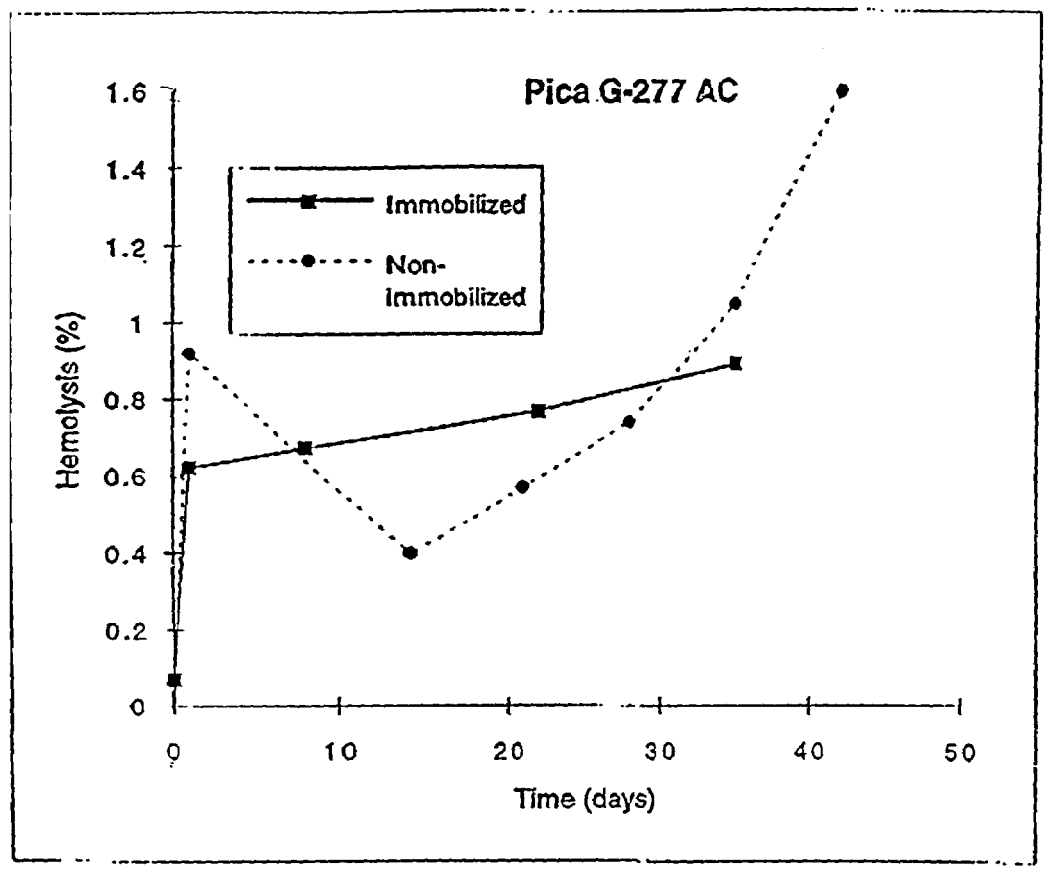
FIG. 21 is a graph showing a comparison of percent hemolysis for the non-immobilized and immobilized adsorbent particle Pica G-277 activated carbon.

Indicators of red blood cell function were monitored over the course of 5-[(β-carboxyethyl)-amino]acridine and GSH removal experiments for various device configurations. Parameters measured included percentage lysis, ATP and $K^+$ concentration. Table 9 shows that ATP concentrations were generally not affected by the presence of a compound removal device: The decrease in ATP concentrations was approximately the same for Control (no IAD) as for the MN-200 or Pica G277 devices. Levels of $K^+$ in PRBCs were found to increase with time. The temperature at which removal occurred did not influence $K^+$ levels in PRBC units exposed to compound removal devices over 20 days. Where the time period of exposure was extended to 35 days, however, the rate of increase of $K^+$ in PRBCs varied with the type of adsorbent, with final levels achieved of 40 and 45 mmol/L for MN-200 and PICA G-277 devices, respectively, compared to the no device control at 39 mmol/L. The percentage of red blood cells lysed in device-exposed and no-device control PRBC units has generally been found to be between 0.1 and 1% after 24 hours. As shown in Table 10 and Table 11 and graphed in FIGS. 20 and 21, the % lysis varied significantly with the type of adsorbent used. Table 10 shows lysis values obtained for PRBCs exposed to two types of immobilized adsorption devices over 35 days. Table 11 shows lysis values obtained for PRBCs exposed to loose adsorbent particles enclosed in a woven polyester mesh over 42 days. A wrist action shaker was used in dosing all PRBC units for 1 minute, after which the PRBCs were in a static condition for 4 hours at room temperature. The devices were held at room temperature for 24 hours on a platelet shaker, after which they were in a static condition at 4° C. for the duration of the study. The immobilization MN-200 showed lower hemolysis levels than immobilized PICA G-277, while the Ambersorb synthetic carbonaceous adsorbent showed one of the lowest hemolysis levels upon comparison of the loose particle adsorbents. The MN-200 LAD showed lower hemolysis than the same non-immobilized adsorbent. Similar observations have been observed for other IADs as compared to the same non-immobilized adsorbent.

TABLE 9

ATP Concentration (μmol/dL) in PRBCs over time

| Time | Control (no IAD) | MN-200 IAD | PICA G277 IAD |
|---|---|---|---|
| 0 hr | 76 | 78 | 79 |
| 4 hr | 80 | 79 | 82 |
| 8 hr | 82 | 82 | 81 |
| 24 hr | 83 | 83 | 86 |
| 8 days | 73 | 70 | 78 |
| 22 days | 50 | 42 | 50 |
| 35 days | 25 | 23 | 28 |

TABLE 10

Percent Lysis in PRBCs (56% HCT) exposed to different IADs over time

| Time | Control (no IAD) | MN-200 IAD | PICA G277 IAD |
|---|---|---|---|
| 0 hr | 0.07 | 0.09 | 0.13 |
| 4 hr | 0.11 | 0.14 | 0.37 |
| 8 hr | 0.12 | 0.18 | 0.53 |
| 24 hr | 0.13 | 0.21 | 0.62 |
| 8 days | 0.18 | 0.22 | 0.67 |
| 22 days | 0.22 | 0.24 | 0.77 |
| 35 days | 0.34 | 0.33 | 0.89 |

TABLE 11

Percent lysis in PRBCs (55% HCT) exposed to different loose particle adsorbents enclosed in woven mesh.

| Time | Control no IAD | Purolite MN-200 | Hemosorba CH-350 | Ambersorb 572 | Darco AC 20 × 50 | Pica G277 |
|---|---|---|---|---|---|---|
| 0 hr | 0.10 | 0.07 | 0.08 | 0.07 | 0.06 | 0.07 |
| 4 hr | 0.07 | 0.09 | 0.38 | 0.10 | 0.08 | 0.13 |
| 8 hr | 0.09 | 0.17 | 0.54 | 0.12 | 0.12 | 0.18 |
| 24 hr | 0.11 | 0.39 | 1.06 | 0.16 | 0.13 | 0.92 |
| Day 14 | 0.12 | 0.48 | 1.11 | 0.22 | 0.13 | 0.40 |
| Day 21 | 0.15 | 0.59 | 1.24 | 0.29 | 0.17 | 0.57 |
| Day 28 | 0.22 | 0.60 | 1.52 | 0.40 | 0.26 | 0.74 |
| Day 35 | 0.30 | 0.78 | 1.85 | 0.55 | 0.41 | 1.05 |
| Day 42 | 0.53 | 1.08 | 2.72 | 0.86 | 0.79 | 1.60 |

The critical nature of the adsorbent particle with respect to the maintenance of red blood cell function is illustrated. A comparative study of the effects of five different adsorbents on red blood cell hemolysis is presented. Ambersorb 572 produced only 0.16% lysis in PRBCs (55%) after a 24 hour exposure, while Darco AC (Norit Americas, Inc. (Atlanta, Ga.) produced 0.13% lysis. Those adsorbents were significantly better at minimizing hemolysis of red blood cells than the Purolite MN-200, Hemosorba CH-350 and Pica G277 adsorbents.

Table 12 shows a comparative study where supernatants from red blood cell samples containing glutathione and 5-[(β-carboxyethyl)amino]acridine were contacted with a number of different adsorbents. Activated carbon adsorbents were the only type of adsorbent that was capable of substantially reducing the concentrations of both 5-[(β-carboxyethyl)-amino]acridine and glutathione. Both natural activated carbons (Norit and PICA) and synthetic activated carbons (Ambersorb) proved to be effective at compound reduction.

TABLE 12

Properties of Several Different Adsorbents

| Adsorbent | Manufacturer | Description@ | GSH Cap^ (µmole/g) $C_f$ = 500 µM | Acridine Cap^ (µmole/g) $C_f$ = 1 µM |
|---|---|---|---|---|
| MN-200 | Purolite | Hypercrosslinked macroreticular PS-DVB, 200-1200 µm particles 1100 m²/g | 0.0* | 17+ |
| Optipore L-493 | Dow Chemical | Hypercrosslinked macroreticular PS-DVB, 300-840 µm particles 1100 m²/g, 46 Å avg. pore diameter | 0.0* | 22* |
| Duolite GT-73 | Rohm & Haas | Macroporous adsorbent with thiol functional groups | 1.7* | 10* |
| Norit A Supra | Norit Americas, Inc. | Steam lignite AC, 2000 m²/g, 97% <150 µm particles | >2790* | 560+ |
| Picatiff Med. | PICA | Powdered AC from coconut husk, 2000 m²/g, 8-35 µm particles | >2670* | >53* |
| Norit ROX 0.8 | Norit | Steam-activate peat AC, extruded 900 m²/g, 840-1000 µm cylinders | >3040* | >60* |
| Ambersorb 572 | Rohm & Haas | Synthetic AC from sulfonated PS, 1100 m²/g, 300-840 µm particles Microporous (ca. 50% pores <20 Å) | >2800* | 134+ |
| G-277 | PICA | Granular activated carbon from coconut husk, | >2640* | >52* |

@PS-DVB = polystyrene-divinyl benzene, AC = activated carbon
^Values listed as ">" were single measurements with residual levels below the assay LOD
*Estimated from single-point adsorption studies in 25% plasma, 75% Erythrosol.
+Estimated from multi-point adsorption isotherms in 25% plasma, 75% Erythrosol.

Example 16

Fiberized media consisting of Dowex Optipore L-493 attached to a nonwoven polyester fiber matrix (Hoechst-L493) has been manufactured by the AQF division of Hoechst Celanese (Charlotte, N.C.). The performance of this adsorbent media in a batch removal device for platelets was evaluated.

Platelet Preparation

Single donor apheresis platelet units containing 3.5-4.5× $10^{11}$ platelets in 300 mL of 35% autologous plasma, 65% PAS III were obtained from the Sacramento Blood Bank Center. 4'-(4-Amino-2-oxa)butyl-4,5',8-trimethyl psoralen (Baxter Healthcare) was added to each platelet unit to achieve a final concentration of 150 µM. Platelet units (4-5) were pooled in a single PL-2410 plastic container and thoroughly mixed. The platelet pool was evenly divided into 4-5 1 L PL2410 plastic containers each containing approximately 300 mL of the platelet mixture. Units were photochemically treated with 3.0 J/cm UV-A and transferred into the appropriate removal device for the study. All experiments included a control platelet unit which was photochemically treated (150 µM psoralen, 3.0 J/cm² UVA) but was not contacted with a removal device.

Device Preparation

Standard removal devices containing 2.5 g of Dowex XUS 43493 were prepared by Baxter Healthcare Corporation (Lot FX1032 D96F20042R). Experimental IADs were prepared with Hoechst-L493 media (Hoechst Celanese Corp.) that was supplied as roll stock. Media was measured and cut to give the appropriate adsorbent mass for each IAD (5.0 g, and 7.5 g). The cut media was placed in pouches constructed by impulse welding 30 µm polyester mesh (Tetko). Mesh pouches containing the media were autoclaved (121° C., 20 min) and placed in sterile PL 2410 plastic containers. Alternatively, mesh pouches were placed in PL 2410 containers, the containers were sealed, and the entire assembly was sterilized by gamma-irradiation to 2.5 MRad (SteriGenics). Excess air was manually evacuated from devices using a syringe prior to transfer of the photochemically treated platelets.

Adsorption Kinetics

Following photochemical treatment with 4'-(4-amino-2-oxa)butyl-4,5',8-trimethyl psoralen+WVA, the platelet mixtures were transferred to PL2410 plastic containers with removal devices. The devices were placed on a standard platelet incubator (Helmer) and agitated at 70 cycles/min at 22° C. Samples of the platelet mixture were removed at 1 hour intervals for the first 8 hours of storage. These samples were stored at 4° C. and later analyzed for residual 4'-(4-amino-2-oxa)butyl-4,5',8-trimethyl psoralen by HPLC analysis. The assay involves an initial sample preparation which lyses the platelets and solubilizes the 4'-(4-amino-2-oxa)butyl-4,5',8-trimethyl psoralen and free photoproducts. The supernatant from the sample preparation is analyzed on a C-18 reverse phase column with a gradient of increasing methanol in $KH_2PO_4$ buffer.

In Vitro Platelet Function

Platelet mixtures were agitated in contact with the removal devices for 7 days. In one study, the platelet mixture was contacted with the IAD for 24 hours and transferred to sterile 1 L PL2410 plastic containers using a sterile tubing welder (Terumo SCD 312). Platelets were placed back in the platelet incubator and stored for the remainder of the 7 day storage period.

Following 5 or 7 days of storage, the platelet count and pH were determined for each platelet unit. The pH and pO2/pCO2 was measured using a CIBA-Corning model 238 Blood Gas Analyzer. The platelet count of each sample was determined using a Baker 9118+Hematology analyzer.

Several assays were performed to evaluate in vitro platelet function. The shape change of platelet samples was monitored using a Chrono-Log model 500 VS whole blood aggregometer. Shape change was quantified as the ratio of maximum change in light transmission following addition of ADP relative to the change in light transmission following addition of EDTA.

The response of platelets to hypotonic stress was evaluated by the Hypotonic Shock Response (HSR) assay. The change in light transmission following addition of a hypotonic solution was measured using a Chrono-Log model 500 VS whole blood aggregometer. Data is reported as percent recovery from the hypotonic stress two minutes after absorbance reached its minimum value.

The ability of platelets to aggregate in response to ADP/collagen agonist was indicated by change in optical transmission as measured by a Chrono-Log model 500 VS whole blood aggregometer.

The status of the platelets was evaluated by scoring the platelet. Samples were blinded and morphology scores of 100 platelets were totaled for each sample. The highest possible score is 400 (Disc=4, intermediate=3, sphere=2, dendrite=1, balloon=0).

Platelet activation as indicated by expression of p-selectin (Granular Membrane Protein, GMP-140) was measured. CD62 antibody was used for the test sample, mouse control IgG1 was used for the negative control, and CD62 antibody with phorbal myristate acetate (PMA) was used for the positive control. Samples were analyzed on a FACScan (Becton Dickinson). The percent of activation that is reported is relative to the positive control and is the difference between the test value and negative control value.

Adsorption Kinetics

Figure 22:
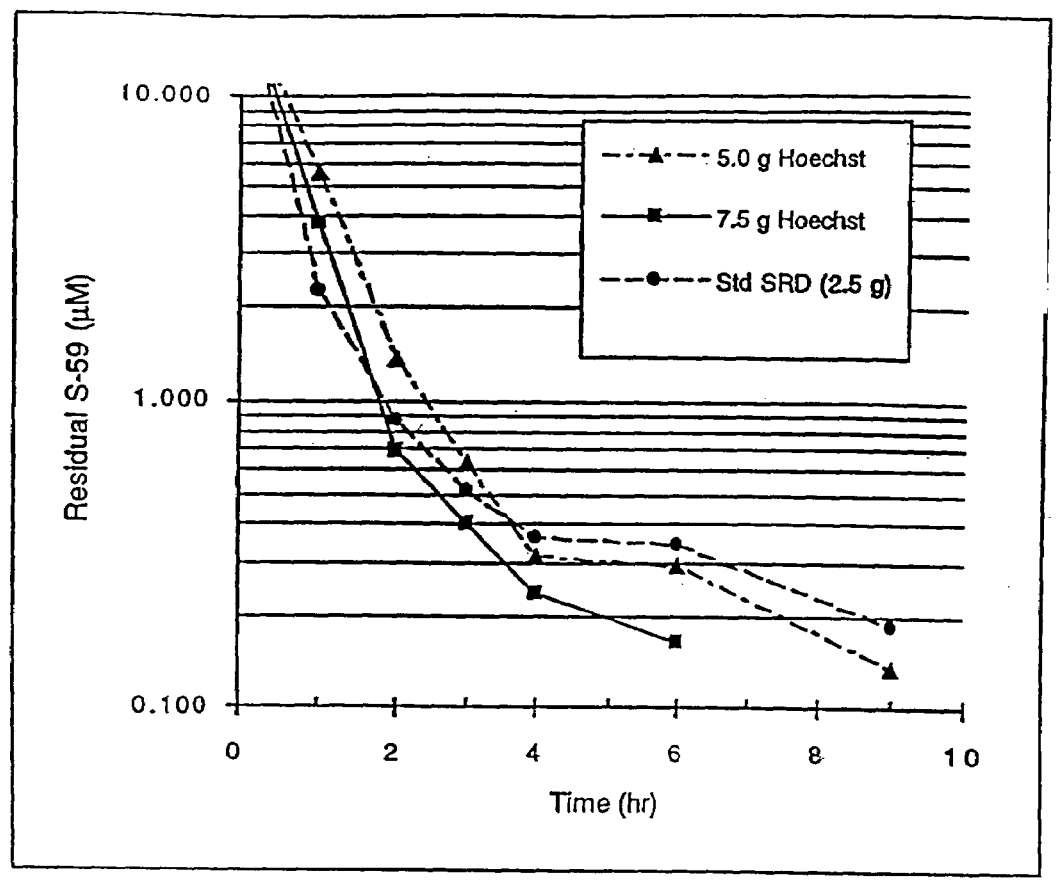
FIG. 22 is a graph showing kinetics for removal 4'-(4-amino-2-oxa)butyl-4,5',8 trimethylpsoralen from platelet concentrates.

The impact of incorporating the adsorbent beads into a fiber matrix was investigated. Platelet units containing $4.0 \times 10^{11}$ platelets in 300 mL of 35% plasma, 65% PAS III were treated with 150 µM 4'-(4-amino-2-oxa)butyl-4,5',8-trimethyl psoralen+3.0 J/cm$^2$ WVA. IADs were prepared from Hoechst-L493 with an adsorbent loading of 450 g/m$^2$. The IADs were sterilized by gamma irradiation. Following treatment with psoralen+UVA, the platelets were transferred to the removal devices. Samples were removed at 1 hour intervals and analyzed for residual 4'-(4-amino-2-oxa)butyl-4,5', 8-trimethyl psoralen by HPLC. FIG. 22 compares the kinetics for removal of 4'-(4-amino-2-oxa)butyl-4,5',8-trimethyl psoralen for IADs containing 5.0 g and 7.5 g Hoechst-L493 media to that of a standard removal device containing 2.5 g of loose beads. IADs contained either 5.0 g Hoechst-L493 (triangles), 7.5 g of Hoechst-L493 media (squares), or 2.5 g of loose Dowex L493 adsorbent beads (circles). The Hoechst-L493 media contained adsorbent beads at a loading of 450 g/m$^2$.

The kinetics of 4'-(4-amino-2-oxa)butyl-4,5',8-trimethyl psoralen adsorption were slower for the Hoechst media when compared to an equal mass of loose adsorbent beads. The removal device containing 2.5 g of loose beads achieved the lowest levels of residual 4'-(4-amino-2-oxa)butyl-4,5',8-trimethyl psoralen at short times (1 hr). However, at longer times, the IADs containing 7.5 g and 5.0 g of Hoechst-L493 media performed better. In this study the adsorption kinetics were relatively rapid with all three removal devices achieving the target of <0.5 µM residual 4'-(4-amino-2-oxa)butyl-4,5', 8-trimethyl psoralen in under 4 hours of contact.

Note that at long times (6-8 hr) the Hoechst-L493 IADs which contained a higher mass of adsorbent achieved lower levels of residual 4'-(4-amino-2-oxa)butyl-4,5',8-trimethyl psoralen. This observation suggests that the slower adsorption kinetics for the Hoechst-LA93 IADs is a result of mass transport limitations (fluid flow vs. diffusion) and is not a result of loss of functional adsorption area due to fiber attachment. Additional studies indicate that Hoechst-L493 media with lower levels of adsorbent loading (200-300 g/m$^2$) allows fluid to penetrate the media more readily resulting in faster kinetics of adsorption.

Previous studies (data not shown) with Hoechst media containing Amberlite XAD-16 adsorbent at a loading of 160 g/m$^2$ indicated that adsorption kinetics were not affected by incorporation into a fiber matrix at a low level of loading.

Platelet Yield and In Vitro Platelet Function

Data from two separate studies are presented in this section. The platelet units within each study were derived from a single pool so that the effect of the IAD media format, adsorbent mass, and contact time could be clearly evaluated.

The first study evaluated the effect of fiberization (Hoechst media) on yield and function of the platelets following extended contact (5 and 7 days). A total of four platelet units that were derived from a single pool were used in this study. The no-IAD control unit was treated with psoralen+UVA. Two of the platelet units were contacted with 5.0 g Hoechst-L493. One unit was contacted with the IAD for 24 hours before being transferred to an empty PL 2410 storage container. The other unit remained in contact with the IAD for the duration of the study. The Hoechst-L493 IADs were sterilized with steam (120° C., 20 min). The standard removal device (2.5 g loose Dowex XUS-43493), which was obtained from Baxter, was sterilized by gamma-irradiation. Note that the platelets were not transferred away from the standard removal device following 8-16 hour contact as is typically the practice with the device that utilizes loose adsorbent particles. Results from platelet counts and in vitro function following 5 and 7 days of storage are summarized in Table 13A and Table 13B respectively.

TABLE 13A (Day 5)
Comparison of Hoechst-L493 Fiberized Media to Standard Removal Device
Platelet Yield and In Vitro Function following 5-Day Storage

| Sample | Platelet Count ($\times 10^{11}$/300 mL) | Yield (%) | pH | pCO$_2$ | pO$_2$ |
|---|---|---|---|---|---|
| Control (+PCT - RD) | 3.50 ± 0.11 | 100 | 6.91 | 18 | 120 |
| 5.0 g Hoechst/L-493 Transfer at 24 hr | 3.41 ± 0.06 | 97 ± 4 | 6.95 | 21 | 95 |

TABLE 13A-continued (Day 5)
Comparison of Hoechst-L493 Fiberized Media to Standard Removal Device
Platelet Yield and In Vitro Function following 5-Day Storage

| | | | | | |
|---|---|---|---|---|---|
| 5.0 g Hoechst/L-493 No Transfer | 3.33 ± 0.08 | 95 ± 4 | 6.93 | 24 | 87 |
| 2.5 g Dowex Optipore L-493 Baxter Lot FX1032 D96F20042R No Transfer | 2.60 ± 0.07 | 74 ± 3 | 7.04 | 13 | 146 |

| Sample | Shape Change | HSR | Aggregation | Morphology | GMP-140 |
|---|---|---|---|---|---|
| Control (+PCT - IAD) | 0.83 ± 0.26 | 0.31 ± 0.08 | 69 ± 4 | 273 | 67.2 |
| 5.0 g Hoechst/L-493 Transfer at 24 hr | 0.90 ± 0.02 | 0.43 ± 0.04 | 83 ± 0 | 268 | 61.5 |
| 5.0 g Hoechst/L-493 No Transfer | 0.83 ± 0.12 | 0.40 ± 0.01 | 80 ± 2 | 280 | 58.9 |
| 2.5 g Dowex Optipore L-493 Baxter Lot FX1032 D96F20042R No Transfer | 0.24 ± 0.04 | 0.38 ± 0.02 | 47 ± 3 | 240 | 71.3 |

TABLE 13B (Day 7)
Comparison of Hoechst-L493 Fiberized Media to Standard Removal Device
Platelet Yield and In Vitro Function following 7-Day Storage

| Sample | Platelet Count ($\times 10^{11}$/300 mL) | Yield (%) | pH | $pCO_2$ | $pO_2$ |
|---|---|---|---|---|---|
| Control (+PCT - IAD) | 3.45 ± 0.06 | 100 | 6.97 | 13 | 126 |
| 5.0 g Hoechst/L-493 Transfer at 24 hr | 3.28 ± 0.22 | 95 ± 7 | 6.90 | 18 | 105 |
| 5.0 g Hoechst/L-493 No Transferred | 3.11 ± 0.15 | 90 ± 5 | 6.88 | 21 | 100 |
| 2.5 g Dowex Optipore L-493 Baxter Lot FX1032 D96F20042R No Transfer | 2.29 ± 0.07 | 66 ± 2 | 7.04 | 9 | 161 |

| Sample | Shape Change | HSR | Aggregation | Morphology | GMP-140 |
|---|---|---|---|---|---|
| Control (+PCT - IAD) | 0.54 ± 0.05 | 0.25 ± 0.03 | 48 ± 0 | 284 | 80.1 |
| 5.0 g Hoechst/L-493 Transfer at 24 hr | 0.76 ± 0.02 | 0.64 ± 0.16 | 86 ± 11 | 267 | 72.7 |
| 5.0 g Hoechst/L-493 No Transfer | 0.67 ± 0.00 | 0.29 ± 0.04 | 79 ± 7 | 280 | 66.1 |
| 2.5 g Dowex Optipore L-493 Baxter Lot FX1032 D96F20042R No Transfer | 0.31 ± 0.09 | 0.28 ± 0.06 | 29 ± 11 | 261 | 77.1 |

The platelet yields for the Hoechst-L493 LADs (5.0 g) were substantially better than the yield for the standard removal device (2.5 g). Losses of <10% were achieved for 7 days of storage in continuous contact with the Hoechst-L493 IAD (5.0 g). Both platelet units that were treated with the Hoechst-L493 IADs displayed better performance in the shape change, aggregation, and GMP-140 assays than the no-IAD control. The platelets that remained in contact with the Hoechst-L493 IAD (5.0 g) for the entire 5 days showed comparable in vitro function to the platelets that were transferred after 24 hours of contact. Interestingly, the platelets that remained in contact with the Hoechst-L493 IAD performed better in the GMP-140 assay. The difference in performance between the two was even larger after 7 days. This observation suggests that contact with the IAD decreases the rate of p-selectin expression by platelets during storage.

The second study looked at IADs containing 5.0 g and 7.5 g of Hoechst-L493 media to determine if there was a significant decrease in platelet yield or in vitro function with a higher mass of media. In this study, the Hoechst-L493 IADs were sterilized by gamma irradiation. A standard removal device (2.5 g Dowex XUS-43493) was included in the study. Platelets remained in contact with the removal devices for the entire duration of the study. Results from platelet counts and in vitro function following 5 and 7 days of storage are summarized in Table 14A and Table 14B respectively.

The results that are summarized in Tables 14A and 14B are similar to the results that were observed in the first study. Platelets that were contacted with the Hoechst-L493 IAD had significantly higher yields than platelets that were contacted with the standard removal device. Platelet yield was slightly lower for the 7.5 g Hoechst-L493 IAD relative to the 5.0 g IAD. Platelets that were treated with the Hoechst-L493 IADs performed comparably to the control platelets in all in vitro assays. Platelets that were contacted with the Hoechst-L493

TABLE 14A (Day 5)
Evaluation of Gamma Sterilized Hoechst-L493 Fiberized Media
Platelet Yield and In Vitro Function following 5-Day Storage (No Transfer)

| Sample | Platelet Count ($\times 10^{11}$/300 mL) | Yield (%) | pH | $pCO_2$ | $pO_2$ |
| --- | --- | --- | --- | --- | --- |
| Control (+PCT - IAD) | 3.96 ± 0.19 | 100 | 6.89 | 25 | 88 |
| 5.0 g Hoechst/L-493 | 3.68 ± 0.16 | 93 ± 6 | 6.89 | 27 | 70 |
| 7.5 g Hoechst/L-493 | 3.44 ± 0.11 | 87 ± 5 | 6.87 | 26 | 84 |
| 2.5 g Dowex Optipore L-493 Baxter Lot FX1032 D96F20042R | 2.85 ± 0.13 | 72 ± 5 | 7.04 | 13 | 145 |

| Sample | Shape Change | HSR | Aggregation | Morphology | GMP-140 |
| --- | --- | --- | --- | --- | --- |
| Control (+PCT - IAD) | 0.56 ± 0.12 | 0.26 ± 0.04 | 73 ± 1 | 289 | 65.1 |
| 5.0 g Hoechst/L-493 | 0.45 ± 0.04 | 0.40 ± 0.00 | 76 ± 2 | 278 | 54.5 |
| 7.5 g Hoechst/L-493 | 0.48 ± 0.06 | 0.25 ± 0.01 | 73 ± 2 | 290 | 55.4 |
| 2.5 g Dowex Optipore L-493 Baxter Lot FX1032 D96F20042R | 0.04 ± 0.06 | 0.30 ± 0.01 | 38 ± 3 | 232 | 62.8 |

TABLE 14B (Day 7)
Evaluation of Gamma Sterilized Hoechst-L493 Fiberized Media
Platelet Yield and In Vitro Function following 7-Day Storage (No Transfer)

| Sample | Platelet Count ($\times 10^{11}$/300 mL) | Yield (%) | pH | $pCO_2$ | $pO_2$ |
| --- | --- | --- | --- | --- | --- |
| Control (+PCT - IAD) | 3.88 ± 0.18 | 100 | 6.99 | 18 | 93 |
| 5.0 g Hoechst/L-493 | 3.67 ± 0.08 | 95 ± 5 | 6.92 | 22 | 81 |
| 7.5 g Hoechst/L-493 | 3.48 ± 0.07 | 90 ± 4 | 6.91 | 20 | 91 |
| 2.5 g Dowex Optipore L-493 Baxter Lot FX1032 D96F20042R | 2.65 ± 0.22 | 68 ± 6 | 7.04 | 9 | 159 |

| Sample | Shape Change | HSR | Aggregation | Morphology |
| --- | --- | --- | --- | --- |
| Control | 0.53 ± 0.12 | 0.23 ± 0.02 | 65 ± 5 | 260 |
| 5.0 g Hoechst/L-493 | 0.54 ± 0.00 | 0.30 ± 0.01 | 83 ± 8 | 266 |
| 7.5 g Hoechst/L-493 | 0.53 ± 0.09 | 0.29 ± 0.01 | 81 ± 13 | 280 |
| 2.5 g Dowex Optipore L-493 Baxter Lot FX1032 D96F20042R | 0.23 ± 0.04 | 0.25 ± 0.03 | 33 ± 9 | 228 |

IADs showed improved performance in the aggregation assay relative to the no-IAD control on day 7. The GMP-140 assay was not performed on day 7.

IADs that were prepared with Hoechst-L493 media (5.0, 7.0 g) resulted in superior in vitro function when compared to standard removal devices (2.5 g loose XUS-43493) stored in contact with the platelets for 5 days. Moreover, platelets that were treated with 150 μM 4'-(4-amino-2-oxa)butyl-4,5',8-trimethyl psoralen+3.0 J/cm$^2$ UVA showed improved in vitro function as indicated by shape change, aggregation, and GMP-140 assays when contacted with Hoechst-L493 IADs (5.0 g) for 5 and 7 days. An additional study that compared 5-7 day storage for platelets (no psoralen/UVA) with and without IAD (50.g Hoechst-L493) demonstrated that storage with an IAD may improve platelet performance as indicated by in vitro function assays.

Example 17

Comparison of AQF Fiberized Beads vs. Free Beads in PRBCs. This study compared the removal of S-300 (N-(9-acridinyl)-β-alanine) and glutathione from PRBC using AQF fiberized vs. free beads of Ambersorb 572.

PRBCs were prepared by centrifuging whole blood at 2100 rpm for 5 minutes and expressing off the plasma, then adding 84 mL of Erythrosol per unit. Six ABO matched units were pooled into a 3.0 L Clintec Viaflex bag. Approximately 300 mL was transferred back to each original PL 146 bag and dosed with 6.0 mL of 150 mM glutathione for a final concentration of 3.0 mM and 3.0 mL of 30 mM S-300 derivative for a final concentration of 300 μM. This was mixed manually and allowed to incubate at room temperature for 4 hours.

The PRBCs were transferred to 1 liter PL 1813 bags containing one of two adsorption devices consisting of either 4.8 g of Ambersorb beads in AQF fiberized media (400 g/m²) or 4.8 g of loose Ambersorb beads. The fiberized media or loose beads are enclosed in a Tekto woven mesh pouch. Duplicates were run for each adsorption device and a unit in a PL 1813 bag without an adsorption device was used as a control. These were stored on a platelet shaker at room temperature for 24 hours, then transferred to storage under static conditions at 4° C. Units were sampled prior to dosing with the S-300 derivative and glutathione, after treatment but prior to transfer to the adsorption devices, and at 2, 4, 6, 8, 20, and 24 hours and 1, 2 and 5 weeks after transfer to the adsorption devices. These samples were prepared for HPLC analysis of S-300 and glutathione and results are shown in table 15. Samples were also analyzed for percentage hemolysis, ATP concentration, $K^+$ concentration, and pH (see table 16).

The results of this experiment suggest that the fiberized resin is preferred over the free beads. The fiberized resin shows equivalent removal of S-300 and glutathione with the benefit of improved red cell function as compared to the free beads. Table 15 shows that the removal of S-300 is similar for the two compound adsorption devices. The removal kinetics for glutathione appear to be slightly better for the fiberized beads but is at acceptable levels for either device after 24 hours. Table 16 shows that for red cell functional assays the fiberized resin treated samples are comparable to the control unit. Comparing the two devices, the ATP and pH are essentially the same. The % hemolysis and $K^+$ levels are much higher after 24 hours for the free beads, indicating substantial loss or red blood cell function.

TABLE 15

Removal of S-300 and glutathione from PRBC using Ambersorb 572 beads in a fiberized media vs. free beads. Residual concentration of compounds in PRBC (S-300) or supernatant (glutathione) after treatment.

| | Time | Ambersorb 572 beads in AQF fiberized media | | Ambersorb 572 free beads | | Control |
|---|---|---|---|---|---|---|
| | | Exp. 1 | Exp. 2 | Exp. 1 | Exp. 2 | |
| Residual S-300 μM | 0 | 33.5 | 33.7 | 31.1 | 32.1 | 32.9 |
| | 2 hr | 4.3 | 6.5 | 5.5 | 6.9 | 42.6 |
| | 4 hr | 2.4 | 2.8 | 3.1 | 2.5 | 54.6 |
| | 6 hr | 1.9 | 1.9 | 2.2 | 2.0 | 66.8 |
| | 8 hr | 2.0 | 2.2 | 2.1 | 1.8 | 74.3 |
| | 20 hr | 2.4 | 2.5 | 2.4 | 2.1 | 113.8 |
| | 24 hr | 2.4 | 2.4 | 2.0 | 2.0 | 120.9 |
| | 1 week | 13.5 | 13.9 | 14.8 | 15.5 | 150.6 |
| | 2 weeks | 17.3 | 18.7 | 17.1 | 17.4 | 174.7 |
| | 5 weeks | 16.7 | 19 | 12.5 | 15.4 | 171.2 |
| Residual glutathione mM | 0 | 6.55 | 6.59 | 6.40 | 6.50 | 6.40 |
| | 2 hr | 0.59 | 0.87 | 1.03 | 1.50 | 6.35 |
| | 4 hr | 0.11 | 0.16 | 0.54 | 0.67 | 6.46 |
| | 6 hr | 0.04 | 0.22 | 0.21 | 0.53 | 6.60 |
| | 8 hr | 0.33 | 0.33 | 0.27 | 0.29 | 6.40 |
| | 20 hr | 0.31 | 0.09 | 0.28 | 0.44 | 6.60 |
| | 24 hr | 0.09 | 0.21 | 0.35 | 0.49 | 6.40 |

TABLE 16

% Hemolysis, K+, ATP, and pH comparison of PRBC treated with Ambersorb 572 as beads in a fiberized media vs. free beads.

| | Time | Ambersorb 572 beads in AQF fiberized media | | Ambersorb 572 free beads | | Control |
|---|---|---|---|---|---|---|
| | | Exp. 1 | Exp. 2 | Exp. 1 | Exp. 2 | |
| % Hemolysis | 0 | 0.13 | 0.14 | 0.13 | 0.11 | 0.15 |
| | 2 hr | 0.14 | 0.16 | 0.61 | 0.81 | 0.14 |
| | 4 hr | 0.19 | 0.13 | 0.98 | 1.73 | 0.11 |
| | 6 hr | 0.24 | 0.17 | 1.49 | 2.73 | 0.12 |
| | 8 hr | 0.29 | 0.19 | 2.18 | 3.37 | 0.12 |
| | 20 hr | 0.29 | 0.28 | 6.66 | 9.56 | 0.14 |
| | 24 hr | 0.37 | 0.35 | 9.57 | 14.67 | 0.20 |
| | 1 week | 0.47 | 0.36 | 9.39 | 13.79 | 0.14 |
| | 2 weeks | 0.45 | 0.39 | 9.94 | 15.55 | 0.25 |
| | 5 weeks | 0.47 | 0.36 | 10.19 | 19.30 | 0.28 |
| $K^+$ mmol/L | 0 | 3.51 | 3.52 | 3.52 | 3.49 | 3.57 |
| | 4 hr | 3.50 | 3.44 | 4.59 | 5.52 | 3.89 |
| | 8 hr | 3.88 | 3.76 | 6.43 | 7.83 | 4.27 |
| | 20 hr | 4.94 | 4.88 | 12.68 | 16.14 | 5.54 |
| | 24 hr | 5.29 | 5.23 | 15.36 | 19.22 | 5.96 |
| | 1 week | 11.36 | 11.14 | 19.38 | 22.47 | 12.46 |
| | 2 weeks | 17.70 | 17.76 | 23.92 | 26.52 | 19.35 |
| | 5 weeks | 32.68 | 31.96 | 34.28 | 35.16 | 35.12 |
| ATP μmol/dL | 0 | 71.37 | 71.18 | 71.18 | 70.40 | 68.84 |
| | 1 week | 63.38 | 62.40 | 60.45 | 58.11 | 69.81 |
| | 2 weeks | 50.90 | 51.48 | 50.27 | 47.00 | 56.55 |
| | 5 weeks | 24.77 | 23.79 | 23.01 | 24.18 | 23.40 |
| pH | 0 | 6.74 | 6.74 | 6.74 | 6.75 | 6.75 |
| | 4 hr | 6.82 | 6.81 | 6.81 | 6.80 | 6.73 |
| | 8 hr | 6.80 | 6.80 | 6.81 | 6.80 | 6.71 |
| | 20 hr | 6.74 | 6.74 | 6.76 | 6.76 | 6.64 |
| | 24 hr | 6.73 | 6.72 | 6.75 | 6.76 | 6.62 |
| | 2 weeks | 6.53 | 6.52 | 6.57 | 6.59 | 6.44 |
| | 5 weeks | 6.40 | 6.39 | 6.46 | 6.48 | 6.26 |

Example 18

Effect of Mode of Agitation on the Removal of S-300 and glutathione and on Red Blood Cell Function using Fiberized Ambersorb 572. This study looked at the effect of the mode of agitation used during IAD treatment on removal of S-300 (N-(9-acridinyl)-β-alanine) and glutathione and on percentage hematocrit, percentage hemolysis, ATP concentration, $K^+$ concentration, and pH.

PRBCs were prepared as one pool and treated as per Example 17. After treatment at room temperature for 4 hours, six units were transferred to LkDs consisting of 4.8 g of Ambersorb 572 (AQF manufactured, 400 g/m²) enclosed in a Tekto woven mesh pouch. The IADs were contained in 1 liter PL1813 bags. A control unit was transferred to a PL 1813 bag without an IAD. These were then treated as follows:

| Test Article | Agitation Type during first 24 hours at room temperature | 4° C. Storage Condition |
|---|---|---|
| 1 | platelet shaker (72 cycles/min) | static |
| 2 | platelet shaker (72 cycles/min) | orbital shaker (intermittent) |
| 3 | orbital shaker (72 cycles/min) | static |
| 4 | platelet rotator (6 cycles/min) | static |
| 5 | Nutator (3-D rotation, 24 cycles/min) | static |
| 6 | static (no agitation) | static |
| 7(control) | platelet shaker (no media or enclosure) | static |

Units were sampled similarly to Example 17. The results indicate that some method of agitation is preferable for the removal of S-300 and glutathione. All modes result in equivalent removal while the orbital shaker shows lower levels of hemolysis than the other methods. Table 17 shows the S-300 and gluthione levels. Table 18 shows the red cell function.

TABLE 17

S-300 and glutathione levels in units treated with various agitiation modes with AQF fiberized Ambersorb 572.

| | | \multicolumn{7}{c}{Test article} | | | | | | |
|---|---|---|---|---|---|---|---|---|
| | | 1 | 2 | 3 | 4 | 5 | 6 | 7 |
| | | \multicolumn{5}{c}{RT agitation mode} | | | |
| | | PS | PS | OS | PR | N | static | Control |
| | | \multicolumn{5}{c}{4° C. condition} | | | |
| | | static | OS | static | static | static | static | static |
| Residual S-300 µM | 0 | 34.7 | 3.8 | 34.3 | 34.2 | 34.7 | 34.8 | 33.9 |
| | 2 hr | 4.4 | 4.7 | 5.0 | 4.0 | 3.6 | 32.5 | 43.9 |
| | 4 hr | 2.9 | 2.5 | 2.2 | 2.7 | 2.1 | 35.9 | 57.4 |
| | 6 hr | 2.3 | 2.1 | 2.3 | 2.1 | 1.8 | 34.7 | 65.1 |
| | 8 hr | 2.5 | 2.0 | 2.0 | 2.0 | 1.7 | 33.6 | 74.4 |
| | 20 hr | 2.0 | 2.0 | 1.9 | 2.0 | 1.8 | 39.0 | 109.2 |
| | 24 hr | 2.9 | 2.5 | 2.6 | 2.6 | 2.5 | 35.5 | 114.6 |
| | 1 week | 13.3 | 8.0 | 15.0 | 15.0 | 16.9 | 26.2 | 141.0 |
| | 2 weeks | 16.3 | 8.6 | 17.7 | 17.1 | 18.0 | 22.6 | 160.6 |
| | 5 weeks | 13.7 | 4.0 | 14 | 12.9 | 14.4 | 14.4 | 166.8 |
| Residual glutathione mM | 0 | 5.97 | 6.02 | 5.98 | 5.96 | 5.92 | 5.92 | 6.93 |
| | 2 hr | 0.52 | 0.71 | 0.84 | 0.65 | 0.55 | 4.39 | 5.99 |
| | 4 hr | 0.74 | 0.82 | 0.73 | 0.67 | 0.64 | 4.33 | 6.93 |
| | 6 hr | 0.59 | 0.67 | 0.59 | 0.6 | 0.55 | 3.79 | 6.41 |
| | 8 hr | 0.55 | 0.62 | 0.61 | 0.58 | 0.55 | 3.38 | 6.56 |
| | 20 hr | 0.10 | 0.10 | 0.10 | 0.10 | 0.10 | 1.82 | 5.70 |
| | 24 hr | 0.10 | 0.10 | 0.10 | 0.10 | 0.10 | 1.15 | 5.03 |

PS = platelet shaker,
OS = orbital shaker,
PR = platelet rotator,
N = Nutator

TABLE 18

% hemolysis, K+, ATP, and pH results with various agitation modes using fiberized AQF Ambersorb 572.

| | | \multicolumn{7}{c}{Test article} | | | | | | |
|---|---|---|---|---|---|---|---|---|
| | | 1 | 2 | 3 | 4 | 5 | 6 | 7 |
| | | \multicolumn{5}{c}{RT agitation mode} | | | |
| | | PS | PS | OS | PR | N | static | Control |
| | | \multicolumn{5}{c}{4° C. condition} | | | |
| | | static | OS | static | static | static | static | static |
| % Hemolysis | 0 | 0.10 | 0.09 | 0.09 | 0.09 | 0.10 | 0.08 | 0.08 |
| | 2 hr | 0.14 | 0.13 | 0.11 | 0.19 | 0.28 | 0.08 | 0.08 |
| | 4 hr | 0.20 | 0.17 | 0.15 | 0.29 | 0.38 | 0.09 | 0.09 |
| | 6 hr | 0.28 | 0.20 | 0.16 | 0.42 | 0.47 | 0.09 | 0.10 |
| | 8 hr | 0.32 | 0.26 | 0.19 | 0.46 | 0.56 | 0.12 | 0.12 |
| | 20 hr | 0.63 | 0.43 | 0.27 | 0.97 | 0.99 | 0.10 | 0.13 |
| | 24 hr | 0.72 | 0.48 | 0.28 | 1.08 | 1.14 | 0.10 | 0.14 |
| | 1 week | 0.73 | 0.53 | 0.30 | 1.11 | 1.16 | 0.15 | 0.15 |
| | 2 weeks | 0.76 | 0.53 | 0.33 | 1.18 | 1.26 | 0.20 | 0.19 |
| | 5 weeks | 1.18 | 0.75 | 0.40 | 1.18 | 1.34 | 0.34 | 0.24 |
| K+ mmol/L | 0 | 3.64 | 3.65 | 3.62 | 3.62 | 3.64 | 3.64 | 3.63 |
| | 4 hr | 3.84 | 3.76 | 3.80 | 4.01 | 4.15 | 3.67 | 4.02 |
| | 8 hr | 4.30 | 4.14 | 4.10 | 4.51 | 4.58 | 3.91 | 4.47 |
| | 20 hr | 5.46 | 5.14 | 4.93 | 5.89 | 5.78 | 4.57 | 5.44 |
| | 24 hr | 5.92 | 5.59 | 5.20 | 6.30 | 6.14 | 4.83 | 5.85 |
| | 1 week | 12.88 | 12.80 | 12.38 | 13.12 | 12.88 | 11.76 | 13.12 |
| | 2 weeks | 18.82 | 19.08 | 18.54 | 19.32 | 19.22 | 18.74 | 20.40 |
| | 5 weeks | 31.65 | 31.50 | 31.40 | 31.25 | 30.65 | 30.65 | 24.80 |
| pH | 0 | 7.35 | 7.32 | 7.35 | 7.35 | 7.34 | 7.35 | 7.35 |
| | 8 hr | 7.47 | 7.44 | 7.44 | 7.43 | 7.46 | 7.39 | 7.32 |
| | 24 hr | 7.41 | 7.41 | 7.45 | 7.44 | 7.40 | 7.39 | 7.29 |
| | 1 week | 7.33 | 7.22 | 7.27 | 7.24 | 7.25 | 7.24 | 7.08 |
| ATP µmol/dL | 0 | 75.08 | 76.83 | 77.22 | 75.86 | 75.86 | 77.22 | 76.25 |
| | 1 week | 62.40 | 62.01 | 65.72 | 63.18 | 62.60 | 66.11 | 66.50 |
| | 2 weeks | 50.31 | 48.36 | 51.29 | 50.12 | 49.14 | 53.43 | 51.29 |
| | 5 weeks | 23.40 | 22.43 | 23.99 | 23.79 | 24.18 | 26.13 | 23.99 |

Example 19

Removal of Activated Complement by fiberized Ambersorb 572 treated PRBCs. This study looked at the formation of complement fragments C3a and SC5b-9 in PRBCs after treatment with an S-300 derivative and glutathione followed by removal using AQF fiberized media.

PRBCs were prepared as one pool and treated as per Example 17. After treatment at room temperature for 4 hours, units were transferred to 1 liter PL 1813 bags containing the following:

| Test Article (PRBC unit #) | Description |
|---|---|
| 1 | no IAD |
| 2 | no IAD-ice incubated |
| 3 | 4.8 g Ambersorb IAD (400 g/m²) (no enclosure) |
| 4 | 7 sheets cellulose acetate membrane (47 mm dia.) |

The cellulose acetate membrane is known to cause complement activation and is used as a positive control. All but unit 2 were treated for 24 hours at room temperature prior to storage under static conditions at 4° C. Unit 2 was stored at 4° C. continuously.

Three 1.5 mL samples were taken from each test article prior to IAD treatment, during treatment after 4, 8, and 24 hours, and 5 days. Each sample was centrifuged at 2000×g for 15 minutes and 450 µL of each supernatant was mixed with 50 µL of cold 200 mM EDTA and vortexed. These were frozen rapidly on dry ice and stored at −70° C.

Enzyme immunoassays (Quidel) were used to detect the formation of complement fragments C3a and SC5b-9. Presence of these fragments are an indication of activation of the complement system. The assay involves binding of the target fragment by a mouse antibody which is conjugated to Horse Radish Peroxidase (HRP) and detection using a chromogenic substrate of the HRP. Sample absorbance was measured against a standard curve to calculate the fragment concentration in the sample. Samples were also assessed for S-300, glutathione and hemolysis similarly to Example 17.

The results indicate that complement activation is reduced in samples treated with the Ambersorb 572 beads in AQF media relative to controls. Table 19 shows that for the controls, complement activation is lower in the sample stored continuously at 4° C. The sample treated with the IAD showed lower levels of C3a and SC5b-9 than the control at 5 days, with C3a near the detection limit after 24 hours. Table 20 indicates that S-300 and glutathione removal was as expected with the AQF media.

TABLE 19

Complement fragment C3a and SC5b-9 levels with various treatments.

| | | Test article | | | |
|---|---|---|---|---|---|
| | | 1 | 2 | 3 | 4 |
| | | | Treatment | | |
| | | no IAD | no IAD 4° C. | AQF no pouch | cellulose acetate |
| C3a | 0 | 411 | 354 | 391 | 388 |
| ng/mL | 24 hr | 609 | 383 | −1 | 701 |
| | 5 days | 665 | 404 | 26 | N/A |
| SC5b-9 | 0 | 38 | 37 | 18 | 25 |
| ng/mL | 24 hr | 120 | 52 | 22 | 87 |
| | 5 days | 226 | N/A | 34 | N/A |

TABLE 20

S-300 concentration (PRBC), glutathione concentration (supernatant), and % hemolysis with various treatments.

| | | Test article | | | |
|---|---|---|---|---|---|
| | | 1 | 2 | 3 | 4 |
| | | | Treatment | | |
| | | no IAD | no IAD 4° C. | AQF no pouch | cellulose acetate |
| Residual | 0 | 30.55 | 30.18 | 29.38 | 29.6 |
| S-300 μM | 24 hr | 121.39 | 61.93 | 2.51 | 118.39 |
| | 5 days | 142.36 | 136.33 | 12.35 | 153.58 |
| glutathione mM | 5 days | 7.15 | 7.26 | 0.72 | 7.07 |
| % | 0 | 0.11 | 0.11 | 0.10 | 0.10 |
| Hemolysis | 24 hr | 0.42 | 0.11 | 0.13 | 0.61 |
| | 5 days | 0.44 | 0.17 | 0.14 | 0.64 |

Example 20

Hemocompatibility enhancement of adsorbent by an inert particulate matrix. This example demonstrates that immobilization of adsorbent particles in an inert particulate matrix enhances the hemocompatibility of the adsorbent without substantially impacting removal of low molecular weight compounds. In addition, this example supports the contention that immobilizing adsorbent particles in an inert matrix (fiber or particulate) is a general method for enhancing the hemocompatibility of the adsorbent. Results for IADs comprised of adsorbent particles immobilized in a fiber matrix and a particulate matrix are presented below.

The media that was studied in this example is comprised of Purolite MN-200 adsorbent particles (200-1200 μm) immobilized in ultra high molecular weight polyethylene (UHMWPE) particulate matrix. Representative media is manufactured by Porex (Fairburn, Ga.). Disks of immobilized adsorbent media were formed by mixing approximately 50% (w/w) Purolite MN-200 (200-1200 μm) with 50% (w/w) UHMWPE particles having a similar particle size. The mixture was placed in a cylindrical cavity and heated under pressure at conditions sufficient to cause the UHMWPE particles to fuse and entrap the adsorbent particles. The resulting disks had a diameter of 3.50 in. and were approximately 0.250 in. thick. The disks weighed approximately 24 g corresponding to approximately 12 g MN-200 in each disk. The IAD was prepared by placing the disk of media in a plastic storage container (PL2410, Baxter Healthcare Corp.) and the entire assembly was sterilized by irradiating with 25-40 kGy of gamma irradiation (Sterigenics, Hayward, Calif.).

The fiber matrix IAD was comprised of Purolite MN-200 immobilized in a non-woven polyester matrix at loading of 300 g adsorbent/m$^2$. Approximately 2.5 g (adsorbent mass) of immobilized Purolite MN-200 was placed in a pouch constructed from 30 μm woven polyester material (Tetko, DePew, N.Y.). The pouch assembly was placed in a plastic storage container (PL2410, Baxter Healthcare Corp.) and the entire assembly was sterilized by irradiating with 25-40 kGy of gamma irradiation (Sterigenics, Hayward, Calif.).

Units of ABO-matched platelet concentrates comprised of platelets (3-5×10$^{11}$ cells) suspended in approximately 300 mL of 35% autologous plasma, 65% platelet additive solution were obtained from Sacramento Blood Bank (Sacramento, Calif.). The platelet units were pooled and divided before dosing each unit with 3 mL of 15 mM aminated psoralen (4'-(4-amino-2-oxa)butyl-4,5',8-trimethyl psoralen). Each unit was subjected to photochemical treatment by illuminating with 3.0 J/cm2 of UVA in a UVA illumination device (Baxter Healthcare Corp.). Two photochemically treated platelet units were transferred to the PL2410 plastic storage containers with the two test SRDs. One treated unit was kept as a control and was not contacted with an IAD. All units were placed on a platelet shaker (Helmer, Noblesville, Ind.) at room temperature (22° C.) for the duration of the experiment.

The kinetics of psoralen adsorption by each of the IAD embodiments was determined. Samples of each platelet unit (ca. 1 mL) were removed at 2 hour intervals during the first 8 hours of storage. These samples were later analyzed for levels of residual psoralen by High Pressure Liquid Chromatography. Following 5 days of storage at room temperature, the platelet counts, pH, and dissolved gases for each of the units was measured. Platelet function was also assessed by performing in vitro tests which included: shape change, aggregation, hypotonic shock response, GMP-140 (p-selectin expression), and morpohology score.

Figure 23:
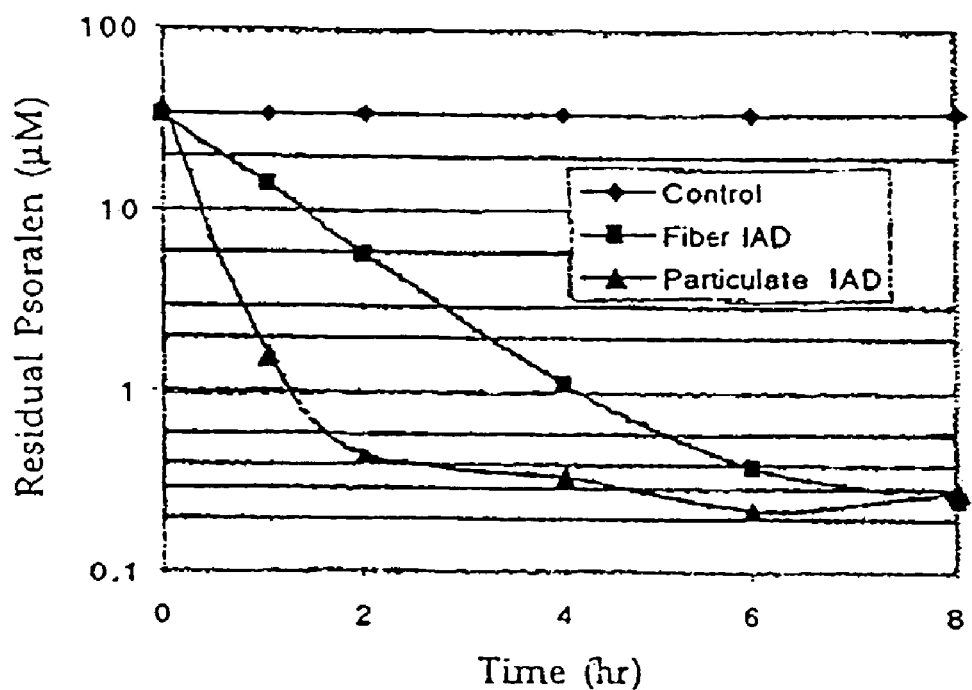
FIG. 23 is a graph showing psoralen adsorption kinetics for fiber matrix IAD (AQF, squares) and particulate matrix IAD (Porex, triangles).

The kinetics for psoralen adsorption are shown in FIG. 23. Both IADs removed the psoralen to the limit of quantitation for the HPLC assay during the eight hour incubation period. The particulate IAD had much faster adsorption kinetics due to the higher mass of adsorbent (about 12 g) relative to the fiber IAD (2.5 g).

The platelet counts, pH measurements, and in vitro platelet function assay results are summarized in Table 21. The fiber and particulate matrix IADs both gave greater than 90% recovery of platelets. This observation is particularly impressive for the particulate IAD considering that it contains about 12 g of MN-200. Note that a removal device that contains 2.5 g of non-immobilized adsorbent particles will typically result in a loss of 25-35% platelets by day 5. A device containing 12 g of non-immobilized particles would therefore by expected to remove >50% of the platelets. It is obvious that immobilizing the adsorbent in the particulate matrix has drastically reduced platelet loss while the kinetics of psoralen removal are still very rapid.

Results from the in vitro platelet function studies are summarized in the second half of Table 21. Once again, both IADs demonstrated satisfactory performance. Hypotonic shock response was slightly higher for the control due to a single high measurement as indicated by the large standard deviation. The IADs did perform better in the aggregation assay with all other assays demostrating essentially identical performance.

TABLE 21

Comparison of Day 5 Platelet Yield and In Vitro Platelet Function for Fiber Matrix and Particulate Matrix IADs

| Sample | Platelet Count ($\times 10^{11}$/300 mL) | % Yield | pH | $pCO_2$ | $pO_2$ | Shape Change | HSR | Aggregation | Morphology | GMP-140 |
|---|---|---|---|---|---|---|---|---|---|---|
| Control | 2.89 ± 0.06 | 100 | 6.95 | 22 | 116 | 1.03 ± 0.33 | 0.71 ± 0.28 | 44 ± 3 | 308 | 67.0 |
| AQF Fiber Matrix IAD (300 g/m² MN-200) | 2.71 ± 0.11 | 94 ± 4 | 6.96 | 23 | 112 | 0.96 ± 0.14 | 0.53 ± 0.06 | 60 ± 0 | 311 | 63.9 |
| Porex Particulate Matrix IAD (50% MN-200) | 2.61 ± 0.10 | 90 ± 4 | 6.90 | 22 | 123 | 1.00 ± 0.05 | 0.42 ± 0.01 | 64 ± 1 | 304 | 66.2 |

The particulate matrix IAD may be further optimized from the present configuration by changing the geometry of the disk to allow more complete penetration of the media disk with liquid. A thinner disk would probably result in equivalent removal kinetics with a lower mass of adsorbent.

In addition to optimizing the geometry of the disk, the wetting of the device and therefore the adsorption kinetics could be further enhanced by increasing the wetting of the media. The inherent hydrophobic nature of the UHMWPE matrix make the device wet slowly during the initial phase of removal. Strategies that could be used to enhance wetting include the use of wetting agents (e.g., glycerol, polyethylene oxide, polyethylene glycol, hydrophilic polymers) or treatment with gas plasma glow discharge. Unlike wetting agents, treatment with glow discharge can be used to directly alter the chemistry of the surface of the UHMWPE binder matrix.

Described above is a batch system. Also described herein is a flow system in accordance with U.S. Ser. No. 10/016,223 filed Dec. 10, 2001, which was incorpoarated by reference in its entirety as if fully put forth below including claims.

The invention claimed is:

1. A pathogen-inactivating compound adsorption system for reducing the concentration of a low molecular weight pathogen-inactivating compound in an aqueous biological composition containing cellular elements, wherein the pathogen-inactivating compound adsorption system comprises a housing compatible with the biological composition containing an adsorption medium comprising porous adsorbent particles immobilized within a sintered matrix formed from polymeric particulate material, wherein the diameter of the adsorbent particles ranges from about 100 μm to about 1500 μm, wherein the adsorbent particles have an affinity for said pathogen-inactivating compound, wherein the system is configured to remove said pathogen-inactivating compound from said biological composition in a batch process, and wherein the system is configured so that the cellular elements in the biological composition treated with the system maintain sufficient biological activity so that said biological composition is suitable for infusion within a human.

2. A system according to claim 1, wherein the porous adsorbent particles have a surface area greater than about 750 m²/g, and the porous adsorbent particles are between 25 and 85 percent of the weight of the adsorption medium.

3. A system according to claim 2, wherein the porous adsorbent particles are between 50 and 80 percent of the weight of the adsorption medium, and the adsorption medium has a particle loading of between 100 and 500 g/m².

4. A system according to claim 3, wherein the adsorption medium has a particle loading of between 250 and 350 g/m².

5. A system according to claim 1, wherein the matrix contains said porous adsorbent particles.

6. A system according to claim 5, wherein the porous adsorbent particles comprise a synthetic polymeric adsorbent having a porous network structure and having a surface area greater than about 750 m²/g.

7. A system according to claim 5, wherein the porous adsorbent particles comprise activated carbon.

8. A system according to claim 6, wherein the porous adsorbent particles comprise a polyaromatic resin.

9. A system according to claim 8, wherein said resin has a pore size between about 25 and 800 Å.

10. A system according to claim 9, wherein said resin has a pore size between about 25 and 150 Å.

11. A system according to claim 10, wherein said resin has a pore size between about 25 and 50 Å.

12. A system according to claim 6, wherein the porous adsorbent particles do not require prewetting before use.

13. A system according to claim 6, wherein the porous adsorbent particles comprise a hypercrosslinked resin.

14. A system according to claim 7, wherein the porous adsorbent particles comprise activated carbon having a surface area between about 1000 and 3000 m²/g.

15. A system according to claim 14, wherein the activated carbon is derived from a synthetic source and at least about 50% of pores of the activated carbon particles have a diameter less than about 20 Å.

16. A system according to claim 6, wherein the diameter of the porous adsorbent particles is between about 300 and 900 μm.

17. A system according to claim 7, wherein the diameter of the porous adsorbent particles is between about 300 and 900 μm.

18. A system according to claim 1 wherein the pathogen inactivating compound comprises a nucleic acid-binding compound.

19. A system according to claim 18, wherein the nucleic acid-binding compound comprises a psoralen derivative.

20. A system according to claim 18, wherein the nucleic acid-binding compound comprises an acridine derivative.

21. A system according to claim 18, wherein the nucleic acid-binding compound comprises a dye.

22. A system according to claim 18, wherein the nucleic acid-binding compound has an electrophilic group or a group capable of forming an electrophilic group.

23. A system according to claim 22, wherein the porous adsorbent particles additionally have an affinity for a quencher.

24. A system according to claim 18, wherein the porous adsorbent particles additionally have an affinity for a degradation product of said nucleic acid-binding compound.

25. A system according to claim 1 or claim 13, wherein the adsorbent particles have an internal surface area between about 300 and 1100 m$^2$/g.

26. A system according to claim 1, or claim 5 wherein the porous adsorbent particles comprise macroreticular adsorbent particles possessing both macropores and micropores.

27. A method for reducing the concentration of a low molecular weight compound in a biological composition containing cellular elements, wherein said low molecular weight compound comprises a nucleic acid-binding compound and wherein said method comprises treating the biological composition with a system of claim 18 for between about 0.5 hour and 5 weeks to adsorb the low molecular weight compound onto the porous adsorbent particles of the system and reduce the concentration of the low molecular weight compound in the biological composition, wherein the cellular elements in the biological composition treated with the system maintain sufficient biological activity so that said biological composition is suitable for infusion within a human.

28. A method according to claim 27, wherein the nucleic acid-binding compound adsorbed onto the porous adsorbent particles of the system comprises an acridine derivative.

29. A method according to claim 27, wherein the nucleic acid-binding compound adsorbed onto the porous adsorbent particles of the system comprises a dye.

30. A method according to claim 27, wherein the biological composition contacts the porous adsorbent particles and the matrix at a temperature of about 22° C. for between about 0.5 hour and seven days.

31. A method according to claim 30, wherein the biological composition comprises platelets.

32. A method according to claim 30, wherein the biological composition contacts the porous adsorbent particles and the matrix at a temperature of about 22° C. for between about 0.5 and about 36 hours.

33. A method according to claim 32, wherein the biological composition is treated with the system at a temperature of about 22° C. for between about 0.5 and about 24 hours.

34. A method according to claim 32, wherein the biological composition is treated with the system at a temperature of about 22° C. for between about 0.5 and about 12 hours.

35. A method according to claim 33 and further comprising subsequently reducing the temperature of the biological composition and the system to 4° C. and contacting the biological composition with the adsorbent particles and the matrix at a temperature of about 4° C.

36. A method according to claim 35, wherein said biological composition contacts the adsorbent particles for at a temperature of about 4° C. for up to 5 weeks.

37. A method according to claim 35, wherein said biological composition comprises red blood cells.

38. A method according to claim 27, wherein the biological composition comprises a blood product.

39. A method according to claim 28, wherein the biological composition comprises a blood product.

40. A method according to claim 29, wherein the biological composition comprises a blood product.

41. A method according to claim 30, wherein the biological composition comprises a blood product.

42. A method according to claim 32, wherein the biological composition comprises a blood product.

43. A method according to claim 33, wherein the biological composition comprises a blood product.

44. A method according to claim 34, wherein the biological composition comprises a blood product.

45. A method according to claim 35, wherein the biological composition comprises a blood product.

46. A method according to claim 36, wherein the biological composition comprises a blood product.

47. A method according to claim 28, wherein the acridine derivative comprises 5-[(β-carboxyethyl)amino]acridine.

48. A method for reducing the concentration of a low molecular weight compound in a biological composition containing cellular elements, wherein said low molecular weight compound comprises a psoralen nucleic acid-binding compound and wherein said method comprises treating the biological composition with a system of claim 18 for between about 0.5 hour and 5 weeks to adsorb the low molecular weight compound onto the porous adsorbent particles of the system and reduce the concentration of the low molecular weight compound in the biological composition, wherein the cellular elements in the biological composition treated with the system maintain sufficient biological activity so that said biological composition is suitable for infusion within a human.

49. A method according to claim 48, wherein no more than about ten percent of an amount of said psoralen nucleic acid-binding compound originally added to said biological composition remains as free psoralen in said biological composition.

50. A method according to claim 48, wherein said psoralen nucleic acid-binding compound is selected from the group consisting of 4'-(4-amino-2-oxa)butyl-4,5',8-trimethyl psoralen, 8-methoxypsoralen, halogenated psoralens, isopsoralens and psoralens linked to quaternary amines, 5'-bromomethyl-4,4 ',8-trimethylpsoralen, 4'-bromomethyl-4,5',8-trimethylpsoralen, 4'-(4-amino-2-aza)butyl-4,5',8-trimethylpsoralen, 4'-(2-aminoethyl)-4,5',8-trimethylpsoralen, 4'-(5-amino-2-oxa)pentyl-4,5',8-trimethylpsoralen, 4'-(5-amino-2-aza)pentyl-4,5',8-trimethylpsoralen, 4'-(6-amino-2-aza)hexyl-4,5',8-trimethylpsoralen, 4'-(7-amino-2,5-oxa)heptyl-4,5',8-trimethylpsoralen, 4'-(12-amino-8-aza-2,5-dioxa)dodecyl-4,5',8-trimethylpsoralen, 4'-(13-amino-2-aza-6,11-dioxa)tridecyl-4,5',8-trimethylpsoralen, 4'-(7-amino-2-aza)heptyl-4,5',8-trimethylpsoralen, 4'-(7-amino-2-aza-5-oxa)heptyl-4,5',8-trimethylpsoralen, 4'-(9-amino-2,6-diaza)nonyl-4,5',8-trimethylpsoralen, 4'-(8-amino-5-aza-2-oxa)octyl-4,5',8-trimethylpsoralen, 4'-(9-amino-5 -aza-2-oxa)nonyl-4,5',8-trimethylpsoralen, 4'-(14-amino-2,6,11-triaza)tetradecyl-4,5',8-trimethylpsoralen, 5'-(4-amino-2-aza)butyl-4,4',8-trimethylpsoralen, 5'-(6-amino-2-aza)hexyl-4,4',8-trimethylpsoralen and 5'-(4-amino-2-oxa)butyl-4,4',8-trimethylpsoralen.

51. A method according to claim 48, wherein the biological composition comprises a blood product.

52. A method according to claim 49, wherein the biological composition comprises a blood product.

53. A method according to claim 50, wherein the biological composition comprises a blood product.

54. A method according to claim 27 or claim 48 wherein the biological composition containing said cellular elements after contacting the porous adsorbent particles has higher yield of cells over a comparable method in which said porous adsorbent particles are not immobilized.

55. A method according to claim 27 or claim 48 wherein the biological composition containing said cellular elements after contacting the porous adsorbent particles has improved performance in an in vitro assay over a comparable method in which said porous adsorbent particles are not immobilized.

56. A pathogen-inactivating compound adsorption system for reducing the concentration of a low molecular weight pathogen-inactivating compound in a biological composition, wherein the pathogen-inactivating compound adsorption system comprises a housing compatible with the biological composition and containing an adsorption medium comprising adsorbent particles having a network pore structure immobilized within a sintered matrix formed from polymeric particulate material, wherein the diameter of the adsorbent particles ranges from about 1 μm to about 200 μm, wherein the adsorbent particles have an affinity for said pathogen-inactivating compound, wherein the system is configured to remove said pathogen-inactivating compound from said biological composition in a flow process, wherein the system is configured so that the biological composition treated with the system maintains sufficient biological activity so that said biological composition is suitable for infusion within a human, the system further comprising a particle retention medium downstream of the adsorption medium, wherein said particle retention medium retains particles shed from said adsorption medium.

* * * * *